(12) United States Patent
Chen et al.

(10) Patent No.: US 7,087,727 B2
(45) Date of Patent: Aug. 8, 2006

(54) PERIOSTIN-BASED DIAGNOSTIC ASSAYS

(75) Inventors: Lan Bo Chen, Lexington, MA (US); Meiru Dai, Malden, MA (US); Hidefumi Sasaki, Nagoya (JP); Daniel Auclair, Asland, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 202 days.

(21) Appl. No.: 10/217,371

(22) Filed: Aug. 13, 2002

(65) Prior Publication Data

US 2003/0073137 A1    Apr. 17, 2003

Related U.S. Application Data

(60) Provisional application No. 60/312,123, filed on Aug. 13, 2001.

(51) Int. Cl.
*C07K 16/18*  (2006.01)
*C07K 16/30*  (2006.01)
*C12N 5/20*   (2006.01)
*C12P 21/08*  (2006.01)
*G01N 33/574* (2006.01)

(52) U.S. Cl. .......... 530/388.85; 435/7.1; 435/70.21; 435/452; 435/332; 435/344; 435/344.1; 436/548; 530/388.2; 530/388.8

(58) Field of Classification Search .......... 435/7.1, 435/7.5, 70.21, 452, 332, 344, 344.1; 436/547, 436/548; 530/388.2, 388.8, 388.85, 389.1, 530/389.7

See application file for complete search history.

(56) References Cited

U.S. PATENT DOCUMENTS 5,756,664 A * 5/1998 Amann et al. ............ 530/326
5,889,159 A * 3/1999 Chen et al. .............. 530/388.8
6,518,063 B1 * 2/2003 Ducy et al. ............... 435/325

FOREIGN PATENT DOCUMENTS

WO    WO 95/11923    5/1995
WO    WO 00/35473    6/2000
WO    WO 01/57062 A1 8/2001

OTHER PUBLICATIONS

Campbell, 1984. Monoclonal Antibody Technology, Elsevier, Amsterdam. pp. 1-4 and 29.*
Harlow et al., 1988. Antibodies. A Laboratory Manual, Cold Spring Harbor Laboratory, Cold Spring Harbor. pp. 72-77.*
Maurer et al., 1980. Proteins and polypeptides as antigens. Meth. Enzymology 70: 49-70.*
Gillan et al., (2002) "Periostin Secreted by Epithelial Ovarian Carcinoma is a Ligand for Integrins and Promotes Cell Motility", Cancer Research, 62:5358-5364.
Sasaki et al., (2001) "Serum Level of the Periostin, a Homologue of an Insect Cell Adhesion Molecule in Thymoma Patients", Cancer Letters, 172:37-42.
Sasaki et al., (2001) "Serum Level of the Periostin, a Homologue of an Insect Cell Adhesion Molecule, as Prognostic Marker in Non-small Cell Lung Carcinomas", Cancer, 92(4):843-848.
Sasaki et al., (2001) "Expression of Periostin, Homologous with an Insect Cell Adhesion Molecules, as a Prognostic Marker in Non-small Cell Lung Cancers", Japanese Journal of Cancer Research, 92:869-873.
Sasaki et al., (2002) "Novel Chemiluminescence Assay for Serum Periostin Levels in Woman With Preeclampsia and in Normotensive Pregnant Woman", Am. J. Obstet. Gynecol., 186(1):103-108.
Wilde et al., (2001) "The Effect of Periostin on Osteoclast Differentiation and Activation", 16(Suppl. 1):S381.
Copy of International Search Report from PCT/US02/25603 mailed Apr. 10, 2003.
Takeshita et al., "Osteoblast-Specific Factor 2: Cloning of a Putative Bone Adhesion Protein With Homology With the Insect Protein Fasciclin I", Biochem. J. (1993) 294:271-278.

* cited by examiner

*Primary Examiner*—Christopher L. Chin
*Assistant Examiner*—James L. Grun
(74) *Attorney, Agent, or Firm*—Fish & Richardson P.C.

(57) ABSTRACT

The invention includes novel human periostin polypeptides and DNAs encoding them. Also embraced by the invention are human periostin specific antibodies, diagnostic assays for metastasis of breast cancer to bone, and preeclempsia.

4 Claims, 9 Drawing Sheets atgattccctttttacccatgttttctctactattgctgcttattgttaaccctataaacgccaacaatcattatgacaagatctt
ggctcatagtcgtatcaggggtcgggaccaaggcccaaatgtctgtgcccttcaacagattttgggcaccaaaaagaa
atacttcagcacttgtaagaactggtataaaaagtccatctgtggacagaaaacgactgttttatatgaatgttgccctggt
tatatgagaatggaaggaatgaaaggctgcccagcagttttgcccattgaccatgtttatggcactctgggcatcgtggg
agccaccacaacgcagcgctattctgacgcctcaaaactgagggaggagatcgagggaaagggatccttcacttactt
tgcaccgagtaatgaggcttgggacaacttggattctgatatccgtagaggtttggagagcaacgtgaatgttgaattac
tgaatgctttacatagtcacatgattaataagagaatgttgaccaaggacttaaaaaatggcatgattattccttcaatgtat
aacaatttggggcttttcattaaccattatcctaatgggggttgtcactgttaattgtgctcgaatcatccatgggaaccagatt
gcaacaaatggtgttgtccatgtcattgaccgtgtgcttacacaaattggtacctcaattcaagacttcattgaagcagaa
gatgacctttcatcttttagagcagctgccatcacatcggacatattggaggcccttggaagagacggtcacttcacact
ctttgctcccaccaatgaggcttttgagaaacttccacgaggtgtcctagaaaggttcatgggagacaaagtggcttccg
aagctcttatgaagtaccacatcttaaatactctccagtgttctgagtctattatgggaggagcagtctttgagacgctgga
aggaaatacaattgagataggatgtgacggtgacagtataacagtaaatggaatcaaaatggtgaacaaaaggatatt
gtgacaaataatggtgtgatccatttgattgatcaggtcctaattcctgattctgccaaacaagttattgagctggctggaa
aacagcaaaccaccttcacggatcttgtggcccaattaggcttggcatctgctctgaggccagatggagaatacactttg
ctggcacctgtgaataatgcattttctgatgatactctcagcatggttcagcgcctccttaaattaattctgcagaatcacat
attgaaagtaaaagttggccttaatgagctttacaacgggcaaatactggaaaccatcggaggcaaacagctcagagt
cttcgtatatcgtacagctgtctgcattgaaaattcatgcatggagaaagggagtaagcaagggagaaacggtgcgatt
cacatattccgcgagatcatcaagccagcagagaaatccctccatgaaaagttaaaacaagataagcgctttagcacct
tcctcagcctacttgaagctgcagacttgaaagagctcctgacacaacctggagactggacattatttgtgccaaccaat
gatgcttttaagggaatgactagtgaagaaaaagaaattctgatacgggacaaaaatgctcttcaaaacatcattctttatc
acctgacaccaggagttttcattggaaaaggatttgaacctggtgttactaacatttttaaagaccacacaaggaagcaaa
atctttctgaaagaagtaaatgatacacttctggtgaatgaattgaaatcaaaagaatctgacatcatgacaacaaatggt
gtaattcatgttgtagataaactcctctatccagcagacacacctgttggaaatgatcaactgctggaaatacttaataaatt
aatcaaatacatccaaattaagtttgttcgtggtagcaccttcaaagaaatccccgtgactgtctatacaactaaaattataa
ccaaagttgtggaaccaaaaattaaagtgattgaaggcagtcttcagcctattatcaaaactgaaggacccacactaac
aaaagtcaaaattgaaggtgaacctgaattcagactgattaaagaaggtgaaacaataactgaagtgatccatggaga
gccaattattaaaaaatacaccaaaatcattgatggagtgcctgtggaaataactgaaaaagagacacgagaagaacg
aatcattacaggtcctgaaataaaatacactaggatttctactggaggtggagaaacagaagaaactctgaagaaattgt
tacaagaagaggtcaccaaggtcaccaaattcattgaaggtggtgatggtcatttatttgaagatgaagaaattaaaaga
ctgcttcagggagacacacccgtgaggaagttgcaagccaacaaaaaagttcaaggttctagaagacgattaagggaa
aggtcgttctcag

Fig. 1A

MIPFLPMFSLLLLLIVNPINANNHYDKILAHSRIRGRDQGPNVCALQQILGT
KKKYFSTCKNWYKKSICGQKTTVLYECCPGYMRMEGMKGCPAVLPIDHV
YGTLGIVGATTTQRYSDASKLREEIEGKGSFTYFAPSNEAWDNLDSDIRRG
LESNVNVELLNALHSHMINKRMLTKDLKNGMIIPSMYNNLGLFINHYPNG
VVTVNCARIIHGNQIATNGVVHVIDRVLTQIGTSIQDFIEAEDDLSSFRAAAI
TSDILEALGRDGHFTLFAPTNEAFEKLPRGVLERFMGDKVASEALMKYHIL
NTLQCSESIMGGAVFETLEGNTIEIGCDGDSITVNGIKMVNKKDIVTNNGVI
HLIDQVLIPDSAKQVIELAGKQQTFTDLVAQLGLASALRPDGEYTLLAPV
NNAFSDDTLSMVQRLLKLILQNHILKVKVGLNELYNGQILETIGGKQLRVF
VYRTAVCIENSCMEKGSKQGRNGAIHIFREIIKPAEKSLHEKLKQDKRFSTF
LSLLEAADLKELLTQPGDWTLFVPTNDAFKGMTSEEKEILIRDKNALQNIIL
YHLTPGVFIGKGFEPGVTNILKTTQGSKIFLKEVNDTLLVNELKSKESDIMT
TNGVIHVVDKLLYPADTPVGNDQLLEILNKLIKYIQIKFVRGSTFKEIPVTV
YTTKIITKVVEPKIKVIEGSLQPIIKTEGPTLTKVKIEGEPEFRLIKEGETITEVI
HGEPIIKKYTKIIDGVPVEITEKETREERIITGPEIKYTRISTGGGETEETLKKL
LQEEVTKVTKFIEGGDGHLFEDEEIKRLLQGDTPVRKLQANKKVQGSRRR
LREGRSQ

Fig. 1B atgattccctttttacccatgttttctctactattgctgcttattgttaaccctataaacgccaacaatcattatgacaagatctt
ggctcatagtcgtatcaggggtcgggaccaaggcccaaatgtctgtgcccttcaacagattttgggcaccaaaaagaa
atacttcagcacttgtaagaactggtataaaaagtccatctgtggacagaaaacgactgttttatatgaatgttgccctggt
tatatgagaatggaaggaatgaaaggctgcccagcagttttgcccattgaccatgtttatggcactctgggcatcgtggg
agccaccacaacgcagcgctattctgacgcctcaaaactgagggaggagatcgagggaaagggatccttcacttactt
tgcaccgagtaatgaggcttgggacaacttggattctgatatccgtagaggtttggagagcaacgtgaatgttgaattac
tgaatgctttacatagtcacatgattaataagagaatgttgaccaaggacttaaaaaatggcatgattattccttcaatgtat
aacaatttggggcttttcattaaccattatcctaatggggttgtcactgttaattgtgctcgaatcatccatgggaaccagatt
gcaacaaatggtgttgtccatgtcattgaccgtgtgcttacacaaattggtacctcaattcaagacttcattgaagcagaa
gatgacctttcatcttttagagcagctgccatcacatcggacatattggaggcccttggaagagacggtcacttcacact
ctttgctcccaccaatgaggcttttgagaaacttccacgaggtgtcctagaaaggttcatgggagacaaagtggcttccg
aagctcttatgaagtaccacatcttaaatactctccagtgttctgagtctattatgggaggagcagtctttgagacgctgga
aggaaatacaattgagataggatgtgacggtgacagtataacagtaaatggaatcaaaatggtgaacaaaaaggatatt
gtgacaaataatggtgtgatccatttgattgatcaggtcctaattcctgattctgccaaacaagttattgagctggctggaa
aacagcaaaccaccttcacggatcttgtggcccaattaggcttggcatctgctctgaggccagatggagaatacactttg
ctggcacctgtgaataatgcattttctgatgatactctcagcatggttcagcgcctccttaaattaattctgcagaatcacat
attgaaagtaaaagttggccttaatgagctttacaacgggcaaatactggaaaccatcggaggcaaacagctcagagt
cttcgtatatcgtacagctgtctgcattgaaaattcatgcatggagaaagggagtaagcaagggagaaacggtgcgatt
cacatattccgcgagatcatcaagccagcagagaaatccctccatgaaaagttaaaacaagataagcgctttagcacct
tcctcagcctacttgaagctgcagacttgaaagagctcctgacacaacctggagactggacattatttgtgccaaccaat
gatgcttttaagggaatgactagtgaagaaaaagaaattctgatacgggacaaaaatgctcttcaaaacatcattctttatc
acctgacaccaggagttttcattggaaaaggatttgaacctggtgttactaacattttaaagaccacacaaggaagcaaa
atctttctgaaagaagtaaatgatacacttctggtgaatgaattgaaatcaaaagaatctgacatcatgacaacaaatggt
gtaattcatgttgtagataaactcctctatccagcagacacacctgttggaaatgatcaactgctggaaatacttaataaatt
aatcaaatacatccaaattaagtttgttcgtggtagcaccttcaaagaaatccccgtgactgtctataagccaattattaaa
aaatacaccaaaatcattgatggagtgcctgtggaaataactgaaaaagagacacgagaagaacgaatcattacaggt
cctgaaataaaatacactaggatttctactggaggtggagaaacagaagaaactctgaagaaattgttacaagaagag
gtcaccaaggggaagttgcaagccaacaaaaaagttcaaggttctagaagacgattaagggaaggtcgttctcag

Fig. 2A

MIPFLPMFSLLLLLIVNPINANNHYDKILAHSRIRGRDQGPNVCALQQILGT
KKKYFSTCKNWYKKSICGQKTTVLYECCPGYMRMEGMKGCPAVLPIDHV
YGTLGIVGATTTQRYSDASKLREEIEGKGSFTYFAPSNEAWDNLDSDIRRG
LESNVNVELLNALHSHMINKRMLTKDLKNGMIIPSMYNNLGLFINHYPNG
VVTVNCARIIHGNQIATNGVVHVIDRVLTQIGTSIQDFIEAEDDLSSFRAAAI
TSDILEALGRDGHFTLFAPTNEAFEKLPRGVLERFMGDKVASEALMKYHIL
NTLQCSESIMGGAVFETLEGNTIEIGCDGDSITVNGIKMVNKKDIVTNNGVI
HLIDQVLIPDSAKQVIELAGKQQTTFTDLVAQLGLASALRPDGEYTLLAPV
NNAFSDDTLSMVQRLLKLILQNHILKVKVGLNELYNGQILETIGGKQLRVF
VYRTAVCIENSCMEKGSKQGRNGAIHIFREIIKPAEKSLHEKLKQDKRFSTF
LSLLEAADLKELLTQPGDWTLFVPTNDAFKGMTSEEKEILIRDKNALQNIIL
YHLTPGVFIGKGFEPGVTNILKTTQGSKIFLKEVNDTLLVNELKSKESDIMT
TNGVIHVVDKLLYPADTPVGNDQLLEILNKLIKYIQIKFVRGSTFKEIPVTV
YKPIIKKYTKIIDGVPVEITEKETREERIITGPEIKYTRISTGGGETEETLKKLL
QEEVTKGKLQANKKVQGSRRRLREGRSQ

Fig. 2B atgattccctttttacccatgttttctctactattgctgcttattgttaaccctataaacgccaacaatcattatgacaagatctt
ggctcatagtcgtatcaggggtcgggaccaaggcccaaatgtctgtgcccttcaacagattttgggcaccaaaaagaa
atacttcagcacttgtaagaactggtataaaaagtccatctgtggacagaaaacgactgttttatatgaatgttgccctggt
tatatgagaatggaaggaatgaaaggctgcccagcagttttgcccattgaccatgtttatggcactctgggcatcgtggg
agccaccacaacgcagcgctattctgacgcctcaaaactgagggaggagatcgagggaaagggatccttcacttactt
tgcaccgagtaatgaggcttgggacaacttggattctgatatccgtagaggtttggagagcaacgtgaatgttgaattac
tgaatgctttacatagtcacatgattaataagagaatgttgaccaaggacttaaaaaatggcatgattattccttcaatgtat
aacaatttggggcttttcattaaccattatcctaatgggggttgtcactgttaattgtgctcgaatcatccatgggaaccagatt
gcaacaaatggtgttgtccatgtcattgaccgtgtgcttacacaaattggtacctcaattcaagacttcattgaagcagaa
gatgacctttcatcttttagagcagctgccatcacatcggacatattggaggcccttggaagagacggtcacttcacact
ctttgctcccaccaatgaggcttttgagaaacttccacgaggtgtcctagaaaaggttcatggggagacaaagtggcttccg
aagctcttatgaagtaccacatcttaaatactctccagtgttctgagtctattatgggaggagcagtctttgagacgctgga
aggaaatacaattgagataggatgtgacggtgacagtataacagtaaatggaatcaaaatggtgaacaaaaaggatatt
gtgacaaataatggtgtgatccatttgattgatcaggtcctaattcctgattctgccaaacaagttattgagctggctggaa
aacagcaaaccaccttcacggatcttgtggcccaattaggcttggcatctgctctgaggccagatggagaatacactttg
ctggcacctgtgaataatgcatttctgatgatactctcagcatggttcagcgcctccttaaattaattctgcagaatcacat
attgaaagtaaaagttggccttaatgagctttacaacgggcaaatactggaaaccatcggaggcaaacagctcagagt
cttcgtatatcgtacagctgtctgcattgaaaattcatgcatggagaaagggagtaagcaagggagaaacggtgcgatt
cacatattccgcgagatcatcaagccagcagagaaatccctccatgaaaagttaaaacaagataagcgctttagcacct
tcctcagcctacttgaagctgcagacttgaaagagctcctgacacaacctggagactggacattatttgtgccaaccaat
gatgcttttaagggaatgactagtgaagaaaaagaaattctgatacgggacaaaaatgctcttcaaaacatcattctttatc
acctgacaccaggagttttcattggaaaaggatttgaacctggtgttactaacattttaaagaccacacaaggaagcaaa
atctttctgaaagaagtaaatgatacacttctggtgaatgaattgaaatcaaaagaatctgacatcatgacaacaaatggt
gtaattcatgttgtagataaactcctctatccagcagacacacctgttggaaatgatcaactgctggaaatacttaataaatt
aatcaaatacatccaaattaagtttgttcgtggtagcaccttcaaagaaatccccgtgactgtctataagccaattattaaa
aaatacaccaaaatcattgatggagtgcctgtggaaataactgaaaaagagacacgagaagaacgaatcattacaggt
cctgaaataaaatacactaggatttctactggaggtggagaaacagaagaaactctgaagaaattgttacaagaagag
gtcaccaaggtcaccaaattcattgaaggtggtgatggtcatttatttgaagatgaagaaattaaaagactgcttcaggga
gacacacccgtgaggaagttgcaagccaacaaaaaagttcaaggttctagaagacgattaagggaaggtcgttctca
g

Fig. 3A

MIPFLPMFSLLLLLIVNPINANNHYDKILAHSRIRGRDQGPNVCALQQILGT
KKKYFSTCKNWYKKSICGQKTTVLYECCPGYMRMEGMKGCPAVLPIDHV
YGTLGIVGATTTQRYSDASKLREEIEGKGSFTYFAPSNEAWDNLDSDIRRG
LESNVNVELLNALHSHMINKRMLTKDLKNGMIIPSMYNNLGLFINHYPNG
VVTVNCARIIHGNQIATNGVVHVIDRVLTQIGTSIQDFIEAEDDLSSFRAAAI
TSDILEALGRDGHFTLFAPTNEAFEKLPRGVLERFMGDKVASEALMKYHIL
NTLQCSESIMGGAVFETLEGNTIEIGCDGDSITVNGIKMVNKKDIVTNNGVI
HLIDQVLIPDSAKQVIELAGKQQTTFTDLVAQLGLASALRPDGEYTLLAPV
NNAFSDDTLSMVQRLLKLILQNHILKVKVGLNELYNGQILETIGGKQLRVF
VYRTAVCIENSCMEKGSKQGRNGAIHIFREIIKPAEKSLHEKLKQDKRFSTF
LSLLEAADLKELLTQPGDWTLFVPTNDAFKGMTSEEKEILIRDKNALQNIIL
YHLTPGVFIGKGFEPGVTNILKTTQGSKIFLKEVNDTLLVNELKSKESDIMT
TNGVIHVVDKLLYPADTPVGNDQLLEILNKLIKYIQIKFVRGSTFKEIPVTV
YKPIIKKYTKIIDGVPVEITEKETREERIITGPEIKYTRISTGGGETEETLKKLL
QEEVTKVTKFIEGGDGHLFEDEEIKRLLQGDTPVRKLQANKKVQGSRRRL
REGRSQ

Fig. 3B atgattccctttttacccatgttttctctactattgctgcttattgttaaccctataaacgccaacaatcattatgacaagatctt
ggctcatagtcgtatcaggggtcgggaccaaggcccaaatgtctgtgcccttcaacagattttgggcaccaaaaagaa
atacttcagcacttgtaagaactggtataaaaagtccatctgtggacagaaaacgactgtgttatatgaatgttgccctggt
tatatgagaatggaaggaatgaaaggctgcccagcagttttgcccattgaccatgtttatggcactctgggcatcgtggg
agccaccacaacgcagcgctattctgacgcctcaaaactgagggaggagatcgagggaaagggatccttcacttactt
tgcaccgagtaatgaggcttgggacaacttggattctgatatccgtagaggtttggagagcaacgtgaatgttgaattac
tgaatgctttacatagtcacatgattaataagagaatgttgaccaaggacttaaaaaatggcatgattattccttcaatgtat
aacaatttggggcttttcattaaccattatcctaatggggttgtcactgttaattgtgctcgaatcatccatgggaaccagatt
gcaacaaatggtgttgtccatgtcattgaccgtgtgcttacacaaattggtacctcaattcaagacttcattgaagcagaa
gatgacctttcatcttttagagcagctgccatcacatcggacatattggaggcccttggaagagacggtcacttcacact
ctttgctcccaccaatgaggcttttgagaaacttccacgaggtgtcctagaaaggatcatgggagacaaagtggcttcc
gaagctcttatgaagtaccacatcttaaatactctccagtgttctgagtctattatgggaggagcagtctttgagacgctgg
aaggaaatacaattgagataggatgtgacggtgacagtataacagtaaatggaatcaaaatggtgaacaaaaaggata
ttgtgacaaataatggtgtgatccatttgattgatcaggtcctaattcctgattctgccaaacaagttattgagctggctgga
aaacagcaaaccaccttcacggatcttgtggcccaattaggcttggcatctgctctgaggccagatggagaatacacttt
gctggcacctgtgaataatgcattttctgatgatactctcagcatggatcagcgcctccttaaattaattctgcagaatcac
atattgaaagtaaaagttggccttaatgagctttacaacgggcaaatactggaaaccatcggaggcaaacagctcaga
gtcttcgtatatcgtacagctgtctgcattgaaaattcatgcatggagaaagggagtaagcaagggagaaacggtgcga
ttcacatattccgcgagatcatcaagccagcagagaaatccctccatgaaaagttaaaacaagataagcgctttacgac
cttcctcagcctacttgaagctgcagacttgaaagagctcctgacacaacctggagactggacattatttgtgccaacca
atgatgcttttaagggaatgactagtgaagaaaaagaaattctgatacgggacaaaaatgctcttcaaaacatcattcttta
tcacctgacaccaggagttttcattggaaaaggatttgaacctggtgttactaacattttaaagaccacacaaggaagca
aaatctttctgaaagaagtaaatgatacacttctggtgaatgaattgaaatcaaaagaatctgacatcatgacaacaaatg
gtgtaattcatgttgtagataaactcctctatccagcagacacacctgttggaaatgatcaactgctggaaatacttaataa
attaatcaaatacatccaaattaagtttgttcgtggtagcaccttcaaagaaatccccgtgactgtctatagacccacacta
acaaaagtcaaaattgaaggtgaacctgaattcagactgattaaagaaggtgaaacaataactgaagtgatccatggag
agccaattattaaaaaatacaccaaaatcattgatggagtgcctgtggaaataactgaaaaagagacacgagaagaac
gaatcattacaggtcctgaaataaaatacactaggatttctactggaggtggagaaacagaagaaactctgaagaaatt
gttacaagaagacacacccgtgaggaagttgcaagccaacaaaaaaagttcaaggatc
</pre>

Fig. 4A

MIPFLPMFSLLLLLIVNPINANNHYDKILAHSRIRGRDQGPNVCALQQILGT
KKKYFSTCKNWYKKSICGQKTTVLYECCPGYMRMEGMKGCPAVLPIDHV
YGTLGIVGATTTQRYSDASKLREEIEGKGSFTYFAPSNEAWDNLDSDIRRG
LESNVNVELLNALHSHMINKRMLTKDLKNGMIIPSMYNNLGLFINHYPNG
VVTVNCARIIHGNQIATNGVVHVIDRVLTQIGTSIQDFIEAEDDLSSFRAAAI
TSDILEALGRDGHFTLFAPTNEAFEKLPRGVLERIMGDKVASEALMKYHIL
NTLQCSESIMGGAVFETLEGNTIEIGCDGDSITVNGIKMVNKKDIVTNNGVI
HLIDQVLIPDSAKQVIELAGKQQTTFTDLVAQLGLASALRPDGEYTLLAPV
NNAFSDDTLSMDQRLLKLILQNHILKVKVGLNELYNGQILETIGGKQLRVF
VYRTAVCIENSCMEKGSKQGRNGAIHIFREIIKPAEKSLHEKLKQDKRFTTF
LSLLEAADLKELLTQPGDWTLFVPTNDAFKGMTSEEKEILIRDKNALQNIIL
YHLTPGVFIGKGFEPGVTNILKTTQGSKIFLKEVNDTLLVNELKSKESDIMT
TNGVIHVVDKLLYPADTPVGNDQLLEILNKLIKYIQIKFVRGSTFKEIPVTV
YRPTLTKVKIEGEPEFRLIKEGETITEVIHGEPIIKKYTKIIDGVPVEITEKETR
EERIITGPEIKYTRISTGGGETEETLKKLLQEDTPVRKLQANKKSSRI

Fig. 4B

PERIOSTIN-BASED DIAGNOSTIC ASSAYS

This application claims priority of U.S. provisional application No. 60/312,123, filed Aug. 13, 2001.

TECHNICAL FIELD

This invention relates to methods of diagnosis, and more particularly to methods of diagnosing metastasis of breast cancer to bone and preeclampsia.

BACKGROUND

Metastatic bone tumors are the most common type of malignant bone lesion seen in adults, and are the most frequent metastatic site after lung and liver [Yoneda et al. (2000) J. Orthop. Sci. 5(1):75–81]. Both osteoblastic and osteolytic bone metastases are major causes of increased morbidity and eventual mortality in breast cancer patients. Approximately 75% of women who die of breast cancer display bone metastases at autopsy [Galasko, Incidence and distribution of skeletal metastases. In: C. S. B. Galasko (ed.) Skeletal Metastases. pp. 14–21, Butterworth, London, 1986; Rubens, The nature of metastatic bone disease. In: Bone Metastases. Diagnosis and Treatment, pp. 1–10, Springer, London, 1991].

Preeclampsia is among the most frequent causes of maternal death and perinatal mortality [Roberts et al. (1993) Lancet 341:1447–1451].

In light of the above considerations, it is important that there be available simple and reliable tests for metastasis of breast cancer to bone and preeclampsia.

SUMMARY

The inventors have identified novel human deletion variants of the protein originally designated osteoblast-specific factor-2 (OSF-2) and now called periostin [Takeshita et al. (1993) Biochem. J. 294:272–278; Horiuchi et al. (1999) J. Bone Miner. Res. 14:1239–1249]. One of the novel periostin variants was isolated from colon cancer cells and is designated TCG1. Text that refers to periostin without specifying a particular variant is pertinent to all the variants disclosed herein. The invention includes these novel periostin polypeptides, DNAs encoding them, vectors containing the DNAs, and cells containing the vectors. The invention also features antibodies, including monoclonal antibodies (mAbs), specific for human periostin and assays using such antibodies for measuring periostin in samples (e.g., blood samples). In addition, the invention embodies methods for diagnosing metastasis of breast cancer to bone and preeclampsia.

More specifically, the invention features a purified antibody that binds specifically to human periostin. The antibody can be a polyclonal antibody or a monoclonal antibody (mAb), e.g., a mAb secreted by the 5H8 hybridoma (ATCC accession no. PTA-4589), the 8H11 hybridoma (ATCC accession no. PTA-4590), the 1B11 hybridoma, the 2C6 hybridoma, the 6B1 hybridoma, the 8E3 hybridoma, the 10A3 hybridoma, or the 7E4 hybridoma. Also embodied by the invention is a hybridoma that secretes a mAb that binds to human periostin, e.g., any of the hybridomas listed above.

Another aspect of the invention is a method of detecting human periostin in a sample. The method involves: (a) contacting the sample with an antibody that binds to human periostin; and (b) determining whether the antibody binds to a component of the sample. Binding of the antibody to a component of the sample indicates the presence of periostin in the sample. The method can further include, prior to contacting the sample with the first antibody that binds to human periostin, contacting the sample with a second antibody that binds to human periostin. An epitope on human periostin to which the first antibody binds is not the same as an epitope to which the second antibody binds. The second antibody can be bound to a solid substrate. The first antibody can be a polyclonal antibody or a mAb. The mAb can be a mAb that is secreted by any of the above-mentioned hybridomas. In addition, the second antibody can be a mAb (such as any of the above-mentioned mAbs) or a polyclonal antibody. The method can comprise, for example, an immunoblot assay or an ELISA assay and the detecting step can involve detecting, for example, chemiluminesence, radioactivity or fluorescence. Alternatively, the detecting step can involve measuring, for example, absorbance of visible or ultraviolet light. The first antibody can be biotinylated and the detecting step involve the use of avidin. Alternatively, the detecting step can involve the use of an antibody that binds to an immunoglobulin molecule.

Also embraced by the invention is a method of diagnosing a metastasis of breast cancer to bone. The method involves: (a) identifying a breast cancer patient suspected of having or being at risk of having a metastasis of breast cancer to bone; and (b) measuring the level of periostin in a sample of a body fluid from the patient. An elevated level of periostin in the sample, compared to a control level of periostin, is an indication that the patient has a metastasis of breast cancer to the bone. The body fluid can be blood or any other body fluid recited herein, e.g., urine.

Another aspect of the invention is a method of diagnosing preeclampsia in a patient. The method involves: (a) identifying a pregnant patient suspected of having or being at risk of having preeclampsia; and (b) measuring the level of periostin in a sample of a body fluid from the patient. An elevated level of periostin in the sample, compared to a control level of periostin, is an indication that the patient has preeclampsia. The body fluid can be blood or any other body fluid recited herein, e.g., urine.

Another aspect of the invention is an isolated DNA that includes a nucleic acid sequence encoding a polypeptide that contains SEQ ID NO:6 or SEQ ID NO:14; the nucleic acid sequence can be SEQ ID NO:5 or SEQ ID NO:13. Alternatively, the isolated DNA can include a nucleic acid sequence encoding a polypeptide containing SEQ ID NO:4 or SEQ ID NO:12; the nucleic acid sequence can be SEQ ID NO:3 or SEQ ID NO:11. The invention also includes a vector containing any of the above DNAs, e.g., a vector in which the nucleic acid sequence is operably linked to a transcriptional regulatory element (TRE). Also included in the invention is a cell containing any of the above vectors.

Also featured by invention is an isolated polypeptide containing SEQ ID NO:4 or SEQ ID NO:6, SEQ ID NO:12 or SEQ ID NO:14. The invention also provides an antigenic fragment of any of the polypeptides. The fragment is shorter than the full-length polypeptide. The fragment can contain, consecutively, residues 725 and 726 of SEQ ID NO:4 or residues 768–771 of SEQ ID NO:12. Also embraced by the invention is a method of making any of the polypeptides of the invention. The method involves: (a) culturing any of the cells of the invention, provided that the vector that the cell contains includes a TRE operably linked to nucleic acid sequence encoding the polypeptide; and (b) isolating the polypeptide from the culture.

"Polypeptide" and "protein" are used interchangeably and mean any peptide-linked chain of amino acids, regardless of length or post-translational modification.

The term "isolated" polypeptide or peptide fragment as used herein refers to a polypeptide or a peptide fragment which either has no naturally-occurring counterpart or has been separated or purified from components which naturally accompany it, e.g., in normal tissues such as lung, kidney, or placenta, tumor tissue such as colon cancer tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated."

An isolated polypeptide (or peptide fragment) of the invention can be obtained, for example, by extraction from a natural source (e.g., from tissues or bodily fluids); by expression of a recombinant nucleic acid encoding the polypeptide; or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

An "isolated DNA" is either (1) a DNA that contains sequence not identical to that of any naturally occurring sequence, or (2) in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as: a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. Also included is a recombinant DNA that includes a portion of SEQ ID NO:3, SEQ ID NO:5, SEQ ID NO:11, or SEQ ID NO:13. The term "isolated DNA" does not include a DNA present within, for example, cDNA or genomic DNA libraries or genomic DNA restriction digests in, for example, a restriction digest reaction mixture or an electrophoretic gel slice.

As used herein, an "antigenic fragment" of a periostin polypeptide is a fragment of the polypeptide that is shorter than the full-length polypeptide and has at least 5% (e.g., 10%, 20%, 30%, 40%, 50%, 60%, 70%, 80%, 90%, 95%, 98%, 99%, 100%, or more) of the ability of the full-length polypeptide to bind to an antibody specific for periostin. Fragments of interest can be made by recombinant, synthetic, or proteolytic digestive methods. Such fragments can then be isolated and tested for their ability to bind to an antibody specific for periostin by methods known in the art. As used herein, "full-length" periostin is immature periostin and thus includes the periostin native signal sequence.

As used herein, an expression control sequence that is "operably linked" to a coding sequence is incorporated into a genetic construct so that the expression control sequence effectively controls expression of the coding sequence.

As used herein, the term "antibody" refers not only to whole antibody molecules, but also to antigen-binding fragments, e.g., Fab, F(ab')$_2$, Fv, and single chain Fv (scFv) fragments. As used herein, a "scFv" fragment is a recombinant fragment of an antibody molecule that contains, in a single polypeptide chain, the antigen-binding regions of an immunoglobulin (Ig) heavy and an Ig light chain. scFv fragments generally either contain (a) no Ig heavy or Ig light chain constant regions or (b) less than the whole constant region of an Ig heavy and/or Ig light chain. Also included are chimeric antibodies.

As used herein, "testing for expression of a periostin gene in non-small cell cancer (NSCLC) tissue" means testing for expression of a periostin gene in NSCLC cells and stromal cells within and immediately surrounding the tumor as it occurs in vivo.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., testing for metastasis of breast cancer to bone, will be apparent from the following description, from the drawings and from the claims.

DESCRIPTION OF DRAWINGS

FIG. 1A is a depiction of the nucleotide sequence (SEQ ID NO:1) of cDNA encoding full-length OSF-2.

FIG. 1B is a depiction of the amino acid sequence (SEQ ID NO:2) of full-length OSF-2.

FIG. 2A is a depiction of the nucleotide sequence (SEQ ID NO:3) of cDNA encoding full-length periostin-L.

FIG. 2B is a depiction of the amino acid sequence (SEQ ID NO:4) of full-length perisotin-L.

FIG. 3A is a depiction of the nucleotide sequence (SEQ ID NO:7) of cDNA encoding full-length periostin-K.

FIG. 3B is a depiction of the amino acid sequence (SEQ ID NO:8) of full-length periostin-K.

FIG. 4A is a depiction of the nucleotide sequence (SEQ ID NO:11) of cDNA encoding full-length periostin-C (TCG1).

FIG. 4B is a depiction of amino acid sequence (SEQ ID NO:12) of full-length periostin-C (TCG1).

DETAILED DESCRIPTION

Figure 5:
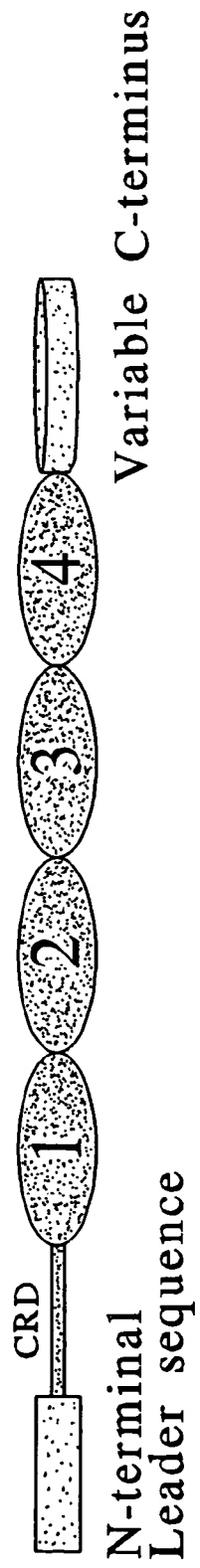
FIG. 5 is a schematic representation of the periostin-C (TCG1) molecule showing the relative positions of an N-terminal leader sequence, a cysteine-rich domain ("CRD"), four internal homologous repeats ("1", "2", "3", and "4"), and a C-terminal domain that varies between periostin variants ("Variable C-terminus").

Sequencing of cDNA products of a reverse transcription-polymerase chain reaction (RT-PCR) analysis of RNA isolated from various tissues revealed novel splice variants of human periostin. One variant that is expressed in placenta and lung is referred to herein as periostin-L. Another that is expressed in kidney is designated periostin-K. In addition, screening of a human carcinoma cDNA library with a DNA fragment derived by differential display of cDNA derived from colon cancer tissue and from normal colon tissue identified a transcript that is over-expressed in colon cancer cells. The cDNA molecule identified encodes another variant (designated herein as TCG1 or periostin-C) of the periostin molecule.

The inventors have also produced a polyclonal antibody (E17) and a variety of monoclonal antibodies that bind to periostin. Using these antibodies, they have also developed a "sandwich" ELISA assay using chemiluminescence for detection.

In clinical studies, the inventors have shown that serum levels of periostin are elevated in breast cancer patients having metastases to bone (compared to breast cancer patients having no sign of bone metastasis), and in patients with preeclampsia (compared to normotensive pregnant women). In a study of patients with a variety of lung cancers, 24% of the patients were found to have elevated serum periostin levels. Moreover, all the patients with very high levels (i.e., >1,000 ng/ml) have died. These findings suggest that periostin is a marker for cancer (e.g., lung cancer), particularly advanced cancer. They also provide the bases for assays to diagnose bone metastasis in breast cancer and preeclampsia.

In addition, ovarian cancer cells and brain tumor cells overexpress periostin [Ismail et al. (2000) Cancer Res. 60:6744–6749; Lal et al. (1999) Cancer Res. 59:5403–5407].

Periostin Nucleic Acid Molecules

The periostin nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:4, 6, 12 and 14). In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. The nucleic acids can be those of a human, non-human primate (e.g., monkey), mouse, rat, guinea pig, cow, sheep, horse, pig, rabbit, dog, or cat. Combinations or modifications of the nucleotides within these types of nucleic acids are also encompassed.

In addition, the isolated nucleic acid molecules of the invention encompass segments that are not found as such in the natural state. Thus, the invention encompasses recombinant nucleic acid molecules (for example, isolated nucleic acid molecules encoding periostin incorporated into a vector (for example, a plasmid or viral vector) or into the genome of a heterologous cell (or the genome of a homologous cell, at a position other than the natural chromosomal location)). Recombinant nucleic acid molecules and uses therefor are discussed further below.

Techniques associated with detection or regulation of genes are well known to skilled artisans. Such techniques can be used to diagnose and/or treat disorders associated with aberrant periostin expression.

A periostin family gene or protein can be identified based on its similarity to the relevant periostin gene or protein, respectively. For example, the identification can be based on sequence identity. The invention features isolated nucleic acid molecules which are at least 50% (or 55%, 65%, 75%, 85%, 95%, or 98%) identical to: (a) the nucleotide sequence of SEQ ID NOS: 2, 4, 6 or 8; and (b) a nucleic acid molecule which includes a segment of at least 30 (e.g., at least 50, 100, 150, 150, 200, 250, 300, 350, 400, 500, 700, 900, 1,100, 1,400, 1,700, 2,000, 2,200, 2,250, 2,300 or 2,310) nucleotides of SEQ ID NO: 3, 5, 11 or 13.

The determination of percent identity between two sequences is accomplished using the mathematical algorithm of Karlin and Altschul (1993) Proc. Natl. Acad. Sci. USA 90:5873–5877. Such an algorithm is incorporated into the BLASTN and BLASTP programs of Altschul et al. (1990) J. Mol. Biol. 215, 403–410. BLAST nucleotide searches are performed with the BLASTN program, score=100, wordlength=12, to obtain nucleotide sequences homologous to periostin encoding nucleic acids. BLAST protein searches are performed with the BLASTP program, score=50, wordlength=3, to obtain amino acid sequences homologous to the periostin polypeptide. To obtain gapped alignments for comparative purposes, Gapped BLAST is utilized as described in Altschul et al. (1997) Nucleic Acids Res. 25:3389–3402. When utilizing BLAST and Gapped BLAST programs, the default parameters of the respective programs (e.g., XBLAST and NBLAST) are used.

Hybridization can also be used as a measure of homology between two nucleic acid sequences. A periostin-encoding nucleic acid sequence, or a portion thereof, can be used as a hybridization probe according to standard hybridization techniques. The hybridization of a periostin probe to DNA or RNA from a test source (e.g., a mammalian cell) is an indication of the presence of periostin DNA or RNA in the test source. Hybridization conditions are known to those skilled in the art and can be found in Current Protocols in Molecular Biology, John Wiley & Sons, N.Y., 6.3.1–6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The invention also encompasses: (a) vectors (see below) that contain any of the foregoing periostin related coding sequences and/or their complements (that is, "antisense"

sequences); (b) expression vectors that contain any of the foregoing periostin related coding sequences operably linked to any transcriptional/translational regulatory elements (examples of which are given below) necessary to direct expression of the coding sequences; (c) expression vectors encoding, in addition to a periostin polypeptide, a sequence unrelated to periostin, such as a reporter, a marker, or a signal peptide fused to periostin; and (d) genetically engineered host cells (see below) that contain any of the foregoing expression vectors and thereby express the nucleic acid molecules of the invention.

Recombinant nucleic acid molecules can contain a sequence encoding periostin or periostin having an heterologous signal sequence. The full length periostin polypeptide, or a fragment thereof, may be fused to such heterologous signal sequences or to additional polypeptides, as described below. Similarly, the nucleic acid molecules of the invention can encode the mature form of periostin or a form that includes an exogenous polypeptide that facilitates secretion.

The transcriptional/translational regulatory elements referred to above and further described below include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trt system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a periostin polypeptide and the second portion being, for example, the reporter described above or an Ig constant region or part of an Ig constant region, e.g., the CH2 and CH3 domains of IgG2a heavy chain. Other hybrids could include an antigenic tag or His tag to facilitate purification.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecule of the invention; insect cell systems infected with recombinant virus expression vectors (for example, baculovirus) containing the nucleic acid molecule of the invention; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a periostin nucleotide sequence; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors of the invention can then be used, for example, for large or small scale in vitro production of a periostin polypeptide or antigenic fragment thereof by methods known in the art. In essence, such methods involve culturing the cells under conditions which maximize production of the polypeptide or antigenic fragment and isolating it from the cells or from the culture medium.

Periostin Polypeptides and Polypeptide Fragments

The polypeptides of the invention include periostin-L, periostin-L without a signal peptide, periostin-C, and periostin-C without a signal peptide, as well as antigenic fragments of these polypeptides. Antigenic fragments of periostin-L can include, consecutively, (a) residues 669 and 670 of SEQ ID NO: 4 and/or (b) residues 725 and 726 of SEQ ID NO:4. Antigenic fragments of periostin-C can include, consecutively, (a) residues 669 and 670 of SEQ ID NO:12 and/or (b) residues 768–771 of SEQ ID NO:12. Antigenic fragments also include the full-length forms of any of the periostin molecules but with the N-terminal 18, 19, 20, 21, 22, 23, 24, or 25 amino acid residues deleted. The polypeptides embraced by the invention also include fusion proteins that contain either full-length periostin (including any of the forms disclosed herein) or an antigenic fragment of it fused to unrelated amino acid sequence. The unrelated sequences can be additional functional domains or signal peptides. Signal peptides are described in greater detail and exemplified below. The polypeptides can be any of those described above but with not more than 50 (i.e., not more than: 50; 40; 30; 20; 15; 12; 10; nine; eight; seven; six; five; four; three; two; or one) conservative substitutions.

The amino acid sequences of the periostin molecules and antigenic fragments thereof can be identical to the wild-type sequences of the periostin molecules and the sequences of the fragments as they occur in the wild-type periostin molecules, respectively. Alternatively, any of the components can contain mutations such as deletions, additions, or substitutions. All that is required is that the mutant periostin molecule have at least 5% (e.g., 10%, 20%, 30%, 40%, 50%, 60%, 70%, 80%, 90%, 95%, 99%, 100%, or even more) of the ability of the wild-type periostin molecule or the antigenic fragment as it occurs in the wild-type periostin molecule to bind to an antibody specific for wild-type periostin. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides can be purified from natural sources (e.g., blood, serum, plasma, tissues or cells such as normal lung or placenta or colon cancer tissue, or any cell that naturally produces periostin polypeptides). The periostin molecules and antigenic fragments can be those of a human, non-human primate (e.g., a monkey), mouse, rat, guinea pig, cow, sheep, horse, pig, rabbit, dog, or cat. Smaller peptides (less than 100 amino acids long) can also be conveniently synthesized by standard chemical means. In addition, both polypeptides and peptides can be produced by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

The polypeptides and antigenic fragments of the invention can be used to generate anti-periostin antibodies or for basic studies on periostin function, e.g., investigations into the significance of its association with various cancers and preeclempsia. The polypeptides and functional fragments can also be used as positive controls in the diagnostic assays of the invention (see below).

Polypeptides and fragments of the invention also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to bind to an antibody specific for periostin in a manner qualitatively identical to that of the periostin functional fragment from which the peptidomimetic was derived. Peptidomimetic compounds can have additional characteristics that enhance their in vivo utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

The in vivo half life of the polypeptides or polypeptide fragments of the invention can also be prolonged by substitution of all or some of the L-amino acid residues of the native molecule or functional fragment with D-amino acids.

Periostin Antibodies

The invention features antibodies that bind specifically to any of the periostin polypeptides or fragments of such polypeptides. Such antibodies can be polyclonal antibodies present in the serum or plasma of animals (e.g., mice, rabbits, rats, guinea pigs, sheep, horses, goats, cows, or pigs) that have been immunized with the relevant periostin polypeptide or peptide fragment using methods, and optionally adjuvants, known in the art. Such polyclonal antibodies can be isolated from, for example, serum, plasma, or ascites by methods known in the art. An example of such a polyclonal antibody is the E17 polyclonal antibody. Monoclonal antibodies that bind to the above polypeptides or fragments are also encompassed by the invention. Methods of making and screening monoclonal antibodies are well known in the art.

Once the desired antibody-producing hybridoma has been selected and cloned, the resultant antibody can be produced by a number of in vivo and in vitro methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for periostin, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240:1041–43; Liu et al. (1987) J. Immunol. 139: 3521–26; Sun et al. (1987) PNAS 84:214–18; Nishimura et al. (1987) Canc. Res. 47:999–1005; Wood et al. (1985) Nature 314:446–49; Shaw et al. (1988) J. Natl. Cancer Inst. 80:1553–59; Morrison, (1985) Science 229:1202–07; Oi et al. (1986) BioTechniques 4:214; Winter, U.S. Pat. No. 5,225,539; Jones et al. (1986) Nature 321:552–25; Verocyan et al. (1988) Science 239:1534; and Beidler et al. (1988) J. Immunol. 141:4053–60.

Also included within the scope of the invention are antibody fragments and derivatives which contain at least the functional portion of the antigen binding domain of an antibody that binds specifically to periostin. Antibody fragments that contain the binding domain of the molecule can be generated by known techniques. For example, such fragments include, but are not limited to: $F(ab')_2$ fragments that can be produced by pepsin digestion of antibody molecules; Fab fragments that can be generated by reducing the disulfide bridges of $F(ab')_2$ fragments; and Fab fragments that can be generated by treating antibody molecules with papain and a reducing agent. See, e.g., National Institutes of Health, 1 *Current Protocols In Immunology*, Coligan et al., ed. 2.8, 2.10 (Wiley Interscience, 1991). Antibody fragments also include Fv (e.g., single chain Fv (scFv)) fragments, i.e., antibody products in which there are few or no constant region amino acid residues. An scFv fragment is a single polypeptide chain that includes both the heavy and light chain variable regions of the antibody from which the ScFv is derived. Such fragments can be produced, for example, as described in U.S. Pat. No. 4,642,334, which is incorporated herein by reference in its entirety.

The antibodies of the invention can bind to all periostin splice variants, a subgroup of splice variants, or a single splice variant. Ways for making and screening for splice variant-specific antibodies are known to those in the art. For example, if it were desired to make an antibody specific for a periostin domain absent in periostin variant x but present in periostin variant y, one could immunize an animal (e.g., a mouse) with periostin variant y and select for antibodies that bind to periostin variant y but not to periostin variant x. Alternatively, the animal could be immunized with a functional fragment of periostin composed of the domain of interest. Antibodies could be selected on the basis of their ability to bind to the functional fragment of periostin and variant y and their inability to bind to variant x.

Applicants deposited under the Budapest Treaty the 5H8 and 8H11 hybridomas with the American Type Culture Collection (ATCC), Rockville, Md. 20852, U.S.A on Aug. 12, 2002. The 5H8 hybridoma was assigned the ATCC accession no. PTA-4589 and the 8H11 hybridoma the ATCC accession no. PTA-4590. The hybridomas deposited with the ATCC were taken from a deposit maintained by the Dana Farber Cancer Institute, Inc., since prior to the priority date of this application. The deposits of hybridomas will be maintained without restriction in the ATCC depository for a period of 30 years, or five years after the most recent request, or for the effective life of the patent, whichever is the longer, and will be replaced if the deposit becomes non-viable during that period.

Diagnostic Assays

The invention features diagnostic assays. Such assays are based on the findings that serum levels of periostin are elevated in breast cancer patients having metastases to bone (compared to breast cancer patients having no sign of bone metastasis) and in patients with preeclampsia (compared to normotensive pregnant women). These findings provide the bases for assays to diagnose bone metastasis in breast cancer and preeclampsia. Such assays can be used on their own or, preferably, in conjunction with other procedures to test for the relevant clinical condition.

In the assays of the invention either: (1) the presence of periostin protein or periostin mRNA in cancer tissue (including surrounding stromal cells) is tested for or their levels are measured; or (2) the level of periostin protein is measured in a liquid sample such as a body fluid (e.g., urine, saliva, semen, blood, or serum or plasma derived from blood); a lavage such as a lung lavage, a gastric lavage, a rectal or colonic lavage, or a vaginal lavage; or a fluid such as a supernatant from a cell culture. In order to test for the presence or measure the level of periostin mRNA in cells, the cells can be lysed and total RNA can be purified or semi-purified from the lysates by any of a variety of methods known to those in the art. Methods of detecting or measuring levels of particular mRNA transcripts are also familiar to those in the art. Such assays include, without limitation, hybridization assays using detectably labeled periostin-specific DNA or probes and quantitative or semi-quantitative RT-PCR methodologies employing appropriate periostin-specific oligonucleotide primers (see Example 1). Additional methods for quantitating mRNA in cell lysates include RNA protection assays and serial analysis of gene expression (SAGE). Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes.

Methods of detecting or measuring the levels of a protein of interest (e.g., periostin) in cells are known in the art. Many such methods employ antibodies (e.g., polyclonal antibodies or mAbs) that bind specifically to the protein. In such assays, the antibody itself or a secondary antibody that binds to it can be detectably labeled. Alternatively, the antibody can be conjugated with biotin, and detectably labeled avidin (a protein that binds to biotin) can be used to detect the presence of the biotinylated antibody. Combinations of these approaches (including "multi-layer" assays) familiar to those in the art can be used to enhance the sensitivity of assays. Some of these assays (e.g., immunohistological methods or fluorescence flow cytometry) can be applied to histological sections or unlysed cell suspensions. The methods described below for detecting periostin in a liquid sample can also be used to detect periostin in cell lysates.

Methods of detecting periostin in a liquid sample (see above) basically involve contacting a sample suspected of containing periostin with an antibody of the invention and testing for binding of the antibody to a component of the sample. In such assays the antibody need not be detectably labeled and can be used without a second antibody that binds to periostin. For example, by exploiting the phenomenon of surface plasmon resonance, an antibody specific for periostin bound to an appropriate solid substrate is exposed to the sample. Binding of periostin to the antibody on the solid substrate results in a change in the intensity of surface plasmon resonance that can be detected qualitatively or quantitatively by an appropriate instrument, e.g., a Biacore apparatus (Biacore International AB, Rapsgatan, Sweden).

Moreover, assays for detection of periostin in a liquid sample can involve the use, for example, of: (a) a single periostin-specific antibody that is detectably labeled; (b) an unlabeled periostin-specific antibody and a detectably labeled secondary antibody; or (c) a biotinylated periostin-specific antibody and detectably labeled avidin. In addition, as described above for detection of proteins in cells, combinations of these approaches (including "multi-layer" assays) familiar to those in the art can be used to enhance the sensitivity of assays. In these assays, the sample or an (aliquot of the sample) suspected of containing periostin can be immobilized on a solid substrate such as a nylon or nitrocellulose membrane by, for example, "spotting" an aliquot of the liquid sample or by blotting of an electrophoretic gel on which the sample or an aliquot of the sample has been subjected to electrophoretic separation. The presence or amount of periostin on the solid substrate is then assayed using any of the above described forms of the periostin-specific antibody and, where required, appropriate detectably labeled secondary antibodies or avidin.

The invention also features "sandwich" assays. In these sandwich assays, instead of immobilizing samples on solid substrates by the methods described above, any periostin that may be present in a sample can be immobilized on the solid substrate by, prior to exposing the solid substrate to the sample, conjugating a second ("capture") periostin-specific antibody (polyclonal or mAb) to the solid substrate by any of a variety of methods known in the art (e.g., see Example 1 below). In exposing the sample to the solid substrate with the second periostin-specific antibody bound to it, any periostin in the sample (or sample aliquot) will bind to the second periostin-specific antibody on the solid substrate. The presence or amount of periostin bound to the conjugated second periostin-specific antibody is then assayed using a "detection" periostin-specific antibody by methods essentially the same as those described above using a single periostin-specific antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either: (a) a mAb that binds to an epitope to that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the used of a capture and detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles. It is noted that periostin-specific antibodies bound to such beads or particles can also be used for immunoaffinity purification of periostin.

Methods of detecting or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, or $^{14}C$), fluorecent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

In assays to diagnose metastasis of breast cancer to bone, the concentration of periostin in, for example, serum from a breast cancer patient suspected of having one or more metastases to bone is compared to a control value. This control value can be, for example, the mean of the concentrations of periostin in a control group of breast cancer patients in whom no bone metastases have been detected. Alternatively, the levels of periostin in the serum of the patient can be measured at various times after a diagnosis of breast cancer. An increase in the level of periostin detected in the serum at a particular time point relative to prior measurements would indicate that the patient's breast cancer had metastasized to bone. In this case the relevant prior measurement would be the control value. A significantly higher concentration of periostin in the serum of the patient relative to the control value would indicate that the patient has a metastasis to bone of her breast cancer.

In assays to diagnose preeclampsia, the patient's serum level of periostin is compared to a control value. The control value can be, for example, the mean of the concentrations of periostin in the sera of control group of normotensive pregnant women. The serum sample from the patient and the control subjects should be obtained at approximately the same stage of pregnancy. Significantly increased levels of periostin in the sera of preeclampsia patients can be detected as early as the first trimester with levels rising with time of gestation. Thus another control value could be the serum level of periostin in a patient of interest at an earlier stage of her pregnancy. A significantly higher concentration of periostin in the serum of the patient relative to the control value would indicate that the patient had preeclampsia.

It is understood that, while the above descriptions of the diagnostic assays refer to assays on serum, the assays can also be carried out on any of the other fluid samples listed herein. In addtion, it is noted that the patients and control subjects referred to above need not be human patients. They can be for example, non-human primates (e.g., monkeys), horses, sheep, cattle, goats, pigs, dogs, guinea pigs, hamsters, rats, rabbits or mice.

The following examples are meant to illustrate, not limit, the invention.

EXAMPLES

Example 1

Methods and Materials

Patients in Study on Bone Metastasis

The study groups included 58 breast cancer and 44 small cell lung cancer patients who had undergone neoadjuvant chemotherapy and/or bone marrow transplantation at the Dana-Farber Cancer Institute.

Blood samples for all studies were collected and processed within 2 hours of collection. Sera were stored at −80° C. until assay.

Patients in Study on Preeclampsia

Thirty nulliparous pregnant women with preeclampsia were matched according to gestational stage with 30 nulliparous normal pregnant women at Magee-Womens Hospital (Pittsburgh, Pa.). Blood samples were obtained in the third trimester (at approximately week 36 of pregnancy) with informed consent as part of an institutional review board-approved longitudinal study of preeclampsia at Magee-Womens Research Institute (University of Pittsburgh, Pittsburgh, Pa.). Preeclampsia was diagnosed in women in their first full term pregnancy whose blood pressure increased by 15 mm Hg diastolic or 30 mm Hg systolic and had proteinuria (300 mg/24 hours or 1+ on a catheterized urine or 2+ on a voided urine or 0.3 on a protein creatinine ratio and hyperuricemia >1SD above normal values for their stage of gestation). None of the patients in this study had an equivocal blood pressure increase i.e., all patients had sustained systolic blood pressures of at least 140 mm Hg and sustained diastolic blood pressures of 90 mm Hg.

Production of Antibodies

The expression vector CMV-6×His-Periostin contains a cDNA sequence encoding mature human periostin-C (see below) linked to: (a) a heterologous leader sequence; and (b) via an enterokinase recognition sequence to a hexa-histidine sequence. The expression vector CMV-Fc-Periostin contains a cDNA sequence encoding mature human periostin-C linked to: (a) a heterologous leader sequence; and (b) a mouse immunoglobulin $\gamma_{2a}$ heavy chain constant region ("Fc-periostin") [Lo et al. (1998) Protein Eng. 11:495–500]. Both expression vectors were transfected by electroporation of the NS/0 mouse myeloma cell line, and stably transfected cells were selected with methotrexate. Periostin produced by the CMV-6×His-Periostin-transfected cell line ("His-periostin") was purified from culture supernatant using the His-Bind Purification Kit (Novagen, Madison, Wis.). After cleavage of the histidine tag with enterokinase (InVitrogen, Carlsbad, Calif.), the periostin protein was injected into rabbits. The E17 polyclonal antibody produced by this immunization was affinity-purified on Affi-gel 10 columns (Amersham Pharmacia Biotech, Piscataway, N.J.) in which the Affi-gel 10 was conjugated to periostin produced by CMV-6×His-Periostin-transfected cells.

Similarly, Fc-periostin was purified from culture supernatant of the CMV-Fc-Periostin-transfected cell line by Protein A affinity chromatography (Amersham Pharmacia Biotech). Fc-periostin fusion protein was injected into mice and the 5H8 monoclonal antibody (mAb) was produced using standard procedures. Seven other human periostin-specific mAb (1B11, 2C6, 6B1, 8H11, 8E3, 10A3, and 7E4) were derived by the same method. All the mAbs are of the IgG class. The 5H8 and 8H11 mAbs are of the IgG1 subclass and have kappa light chains. Purified 5H8 IgG antibody was biotinylated using the Sulfo-NHS-LS Biotinylation Kit (Pierce, Rockford, Ill.).

Cell Culture

The mAb producing hybridomas and the malignant mesothelioma cell line, JMN1B, were cultured in DMEM (GibcoBRL, Grand Island, N.Y.) containing 10% fetal bovine serum (GibcoBRL).

Immunohistochemistry

Sections of human invasive ductal breast cancer tissue were purchased from Novagen. The paraffin-embedded slides were deparaffinized by incubation in xylene and rehydrated in graded ethanol-water solutions. The samples were treated in a microwave oven for 15 minutes with citrate buffer (pH6.0). Endogenous peroxidases were inhibited with 0.3% $H_2O_2$ in methanol and non-specific protein-binding sites were blocked with normal horse serum. Staining of the sections was carried out using the Vecastain® Universal Elite® ABC kit (Vector Laboratories, Burlingame, Calif.). The sections were incubated overnight at 4° C. with diluted affinity-purified E17 polyclonal antibody (see Example 2), and then, after washing, with the biotinylated secondary antibody for 1 hour at room temperature. After further washing, the sections were incubated for 30 minutes at room temperature with a reagent composed of a preformed macromolecular complex of avidin and biotinylated horseradish peroxidase. The substrate for the color reaction was 3,3-diaminobenzidine. Sections were counterstained with hematoxylin before mounting. A negative control slide was processed simultaneously; in this control slide "preimmune serum" was used instead of the E17 polyclonal antibody.

In situ RNA Hybridization

The sections of human invasive ductal breast cancer described above and others of human squamous lung cancer tissues (also purchased from Novagen) were used for in situ RNA hybridization. The paraffin embedded sections were deparaffinized by incubation in xylene and rehydrated in graded ethanol water solutions. In situ RNA hybridization was performed as described previously [Gunn et al. (1998) Proc Natl Acad Sci USA 95(1):258–263]. A 392-bp fragment encoding the N-terminus (starting from the ATG initiation codon) of human periostin-C was excised using BamHI and EcoRI from human periostin cDNA and then cloned in pBluescript (Stratgene, La Jolla, Calif.). Sense and antisense probes were generated with the T3 and T7 RNA polymerases, respectively, in the presence of $[^{35}S]$-UTP, using the 392-bp fragment as a template. All periostin variant-encoding cDNAs characterized at this time have identical nucleotide sequences in the N-terminal region corresponding to the 392-bp fragment, and thus probes made using the fragment as a template would detect all the variant mRNA molecules.

Periostin Chemiluminescence Assay

Patient serum samples were diluted 2-fold with 20 mM Tris-HCl (pH 8.0) and applied to Sep-Pak™ QMA cartridges (New Bedford, Mass.), which were then washed with 20 mM Tris-HCl (pH 8.0) containing 0.1 M NaCl. The cartridges were then eluted with 20 mM Tris-HCl (pH 8.0) containing 0.25 M NaCl. The eluates were immediately frozen and lyophilized. Lyophilized samples were reconstituted and diluted (8-fold or 40-fold) for assay with standard diluent buffer (Tris-buffered saline (TBS), pH 7.4, containing 0.1% BSA and 0.05% Tween 20).

All samples were assayed in duplicate. Reacti-Bind™ NeutrAvidin-coated polystyrene white plates (Pierce, Rockford, Ill.) were pre-washed three times with diluent buffer. Biotin-conjugated 5H8 monoclonal antibody (100 μl/well) was added to each well of the avidin pre-coated plates which were then incubated overnight at 4° C. In some assays, normal plates (i.e., plates not coated with avidin) were used and in these assays 5H8 monoclonal antibody without biotin was coated directly onto the plate well bottoms. The plates were washed 3 times for 10 minutes per wash in diluent buffer. Non-specific protein-binding sites in the wells were blocked by adding PBS (phosphate buffered saline) containing bovine serum albumin (BSA; 3% w/v) to the wells and incubating the plates for 2 hours at 37° C. The plates were then washed three times with diluent buffer. The diluted samples or purified periostin (produced using the CMV-6× His-Periostin vector; see above) (at various concentrations as standards) were added to the wells and the plates were incubated for 3 hours at 37° C. After further washes (as above) affinity-purified polyclonal antibody E17 was added to the wells, and the plates were incubated for 2 hours at 37° C. Unbound antibody was washed away and an alkaline phosphatase-conjugated, affinity-purified antibody specific for rabbit IgG was added to all the wells (Tropix, Bedford, Mass.). The plates were incubated for 2 hours at 37° C. After further washes, 100 μl of Assay buffer (Tropix) was added and incubated for 10 minutes at room temperature. The Assay buffer was completely removed by inverting and tapping the plates. The CSPD (3-(4-methoxyspiro[1,2-dioxetane-3-2'(5'-chloro)-tricyclo [3.3.1.1] decan]-4yl) phenyl phosphate) chemiluminescent substrate (Tropix) was then added. Chemiluminescence intensity was read within 30 minutes using a FL 600 fluorescence microplate reader (Bio-tek Instruments, Winooski, Vt.) following the manufacturer's instructions.

RT-PCR Assay for Periostin cDNAs synthesized from poly A+ RNA isolated from a variety of human tissues were purchased from Clontech, Palo Alto, Calif. PCR was performed as follows. The oligonucleotide primer sequences designed to amplify full length periostin DNA were 5'-ATGATTCCCTTTTTAC-CCATGTTTTCTCTA-3' (forward) (SEQ ID NO:15) and 5'-TCACTGAGAACGACCTTCCCTTAATCGTCTTCTA-3' (reverse) (SEQ ID NO:16). PCR was performed for 38 cycles (30 sec. at 94° C., 45 sec. at 49° C., 150 sec. at 72° C.) Six μl aliquots were subjected to electrophoresis on a 1% agarose gel, and the amplicons were visualized by ethidium bromide staining. The specificity of the PCR was confirmed by sequencing of the product. Control PCRs were performed using GAPDH specific oligonucleotide primers as described above.

Palindromic PCR cDNA Display

Total cellular RNA was extracted from tumor or normal tissues (surgical specimens) or cultured cells by using Tri-reagent (Leedo Medical Lab., Houston, Tex.). Surgical specimens were obtained from the New England Deaconess Hospital Department of Surgery as previously described [Barnard et al. (1992) Cancer Res., 52:3067–3072]. PolyA+ mRNA was purified using oligo dT magnetic beads (Promega, Madison, Wis.).

PolyA+ mRNA (100 ng) from tissue was reverse transcribed to cDNA with a single palindromic primer (5'-CTGATCCATG-3') (SEQ ID NO:17) (2 mM) and 0.5 unit of rTh DNA polymerase (Perkin Elmer Cetus) in the presence of $MnCl_2$ (1.0 mM) at 70° C. for 12 min (total volume: 5 μl) (3 cycles). Reverse transcription was followed by 40 cycles of a palindromic PCR reaction (94° C., 30 sec.; 40° C., 100 sec.; 72° C., 35 sec.) with the same palindromic (0.4 mM) and rTh DNA polymerase in the presence of $MgCl_2$ (2.0 mM) and [$^{35}S$]-dATP in the same reaction tube used for reverse transcription (total volume: 25 μl). Amplified palindromic PCR products ($^{35}S$-labeled) were resolved on a polyacrylamide gel. cDNA patterns derived from tumor and the adjacent normal tissue were directly compared.

The cDNA bands of interest were excised and recovered from the gel. Recovered cDNA fragments were reamplified with Taq DNA polymerase (Perkin Elmer) in Tricine buffer (10 mM Tricine, 50 mM KCl, 1.5 mM $MgCl_2$, 0.001% gelatin, pH 8.4) instead of standard Tris PCR buffer. Reamplified cDNA fragments were analyzed by agarose gel electrophoresis.

Statistical Methods

Statistical analyses were carried out using the Mann-Whitney U-test for unpaired samples. Linear relationships between variables were determined by means of simple linear regression. Correlation coefficients were determined by rank correlation using Spearman's test. Differences between means were tested for significance using the test of Kruskal-Wallis and Fisher's PLSD test. All analyses were done using the StatView™ software package (Abacus Concepts Inc.). Differences were considered significant when the p value was less than 0.05.

Example 2

Periostin JMN1B is a 90 kDa Secreted Protein

Previous studies of the inventors showed that periostin transcripts are detectable in many cancer tissues but not in any of the cancer cell lines tested except the malignant mesothelioma cell lines JMN and JMN1B [Behbehani et al. (1982) Hum Pathol, 13(9):862–866; Demetri et al. (1989) Blood, 74:940–946]. Conditioned medium of JMN1B cells was concentrated 10-fold and both this concentrate and JMN1B cell lysate were analyzed by Western blotting. The E17 polyclonal antibody preparation raised against human periostin contained antibodies that bound to both periostin and βigH3. Western blotting with the E17 polyclonal antibody revealed both periostin and βigH3 to be more abundant in JMN1B supernatant than in cell lysate. After affinity purification with periostin bound to a solid substrate, the ability of the E17 polyclonal antibody to bind to βigH3 was eliminated leaving only the ability to bind to periostin which migrated as a 90 kDa bond on sodium dodecyl sulfate polyacrylaminde gel electrophoresis (SDS-PAGE). The E17 polyclonal antibody did not immunoprecipitate periostin but the 5H8 mAb did. Thus, the 5H8 monoclonal antibody was used for capture and the affinity-purified E17 polyclonal antibody for detection of periostin in "sandwich" assays for periostin.

JMN1B cells were treated with 1.5 μM of monensin (Sigma Co., St. Louis, Mo.) which is an inhibitor of intracellular vesicular transport. Five hours after addition of monensin to the cell cultures, periostin could be detected by Western blotting in cell lysate but not in culture medium. In addition, the affinity-purified E17 antibody stained the Golgi of control cells. However, monensin treatment resulted in punctate cytoplasmic staining.

In toto, the above findings indicate that periostin (as expressed by JMN1B cells) is a 90 kDa secreted protein.

Example 3

Expression of Periostin in Breast Cancer

Periostin protein could be detected by immunohistochemistry using the E17 antibody immunopurified as described above. Strong staining was seen in the invasive breast cancer cells, but the surrounding normal stromal cells were only faintly stained. Strong staining was also observed in the advancing margin of breast cancer, as opposed to the central area of the tumor. On the other hand, strong staining was not detected in sections of non-invasive, normal breast tissues. Periostin mRNA could also be detected by in situ RNA hybridization. High expression of the periostin gene was observed in the stromal cells surrounding breast carcinoma whereas very little expression was found in cancer cells. While the invention is not limited by any particular mechanism of action, it seems likely that the thin layer of stromal cells at the edge of the tumor secrete periostin, which then binds to the surface of the tumor cells. Naturally, it also possible that the tumor cells are producing periostin, possibly at a lower level than the stromal cells at the edge of the tumor. No signal was seen in normal breast tissue sections.

Example 4

Serum Level of Periostin in Cancer Patients as a Predictor of Bone Metastases

The clinical and pathological characteristics of the 58 breast cancer patients studied are shown in Table 1. These included 7 cases at stage II, 15 at stage III, and 36 at stage IV. The median age was 44.5 years (range 31–63). Among the 36 stage IV patients, 15 (42%) were diagnosed with one metastasis site, and 21 (58%) had more than two. Among a subset of 40 patients (mixed stages), the tumors in 24 (60%) were estrogen receptor-positive. In a subset of 38 patients, the tumors in 24 (63%) were progesterone receptor-positive. In a subset of 40 patients, 29 (72.5%) were premenopausal and 11 (27.5%) were postmenopausal.

TABLE 1

CLINICOPATHOLOGICAL DATA ON 58 BREAST CANCER PATIENTS

| | | Serum Periostin | |
|---|---|---|---|
| Factors | No. of patients | Periostin levels (ng/ml) | p-value |
| Mean age 44.4 ± 1.1 years | 58 | | 0.2012 $r^2 = 0.0369$* |
| Menopause | | | |
| Pre menopausal | 29 (72.5%) | 89.8 ± 25.3 | 0.4309 |
| post menopausal | 11 (27.5%) | 41.7 ± 11.0 | |
| Tumor status | | | |
| T1 | 11 (27.5%) | 65.7 ± 15.7 | NS |
| T2 | 17 (42.5%) | 63.6 ± 24.7 | |
| T3 | 4 (10.0%) | 91.8 ± 52.8 | |
| T4 | 8 (20.0%) | 124.4 ± 72.8 | |
| Stage | | | |
| II | 7 (12.1%) | 56.1 ± 14.3 | NS |
| III | 15 (25.9%) | 28.0 ± 4.7 | |
| IV | 36 (62.1%) | 85.3 ± 20.5 | |
| Bone metastasis | | | |
| negative | 37 (63.8%) | 55.0 ± 16.6 | 0.04 |
| positive | 21 (36.2%) | 89.3 ± 21.8 | |
| No. of metastasis sites | | | |
| one | 15 (41.7%) | 75.9 ± 29.7 | 0.2546 |
| more than two | 21 (58.3%) | 92.0 ± 28.6 | |
| Lymph node metastasis | | | |
| Positive | 36 (78.3%) | 95.3 ± 25.0 | 0.5411 |
| Negative | 10 (21.7%) | 44.4 ± 8.4 | |
| ER status | | | |
| negative | 24 (60.0%) | 72.1 ± 19.0 | 0.8359 |
| positive | 16 (40.0%) | 88.4 ± 38.0 | |
| PR status | | | |
| negative | 24 (63.2%) | 72.3 ± 19.1 | 0.9758 |
| positive | 14 (36.8%) | 94.8 ± 43.1 | |
| Grading | | | |
| II | 6 (17.1%) | 128.3 ± 62.0 | 0.189 |
| III | 29 (82.9%) | 65.8 ± 21.1 | |

*Correlation of age with periostin levels for all 58 patients
NS, not significant;
ER, estrogen receptor;
PR, progesterone receptor The clinical and pathological characteristics of the 44 small cell lung cancer patients are shown in Table 2. This group of patients included 32 cases at stage III and 12 cases at stage IV. The median age was 51 years (range 26–62). Among the 12 stage IV patients, 5 had a single metastasis site, and 7 were diagnosed with more than two metastasis sites (Table 2).

TABLE 2

CLINICOPATHOLOGICAL DATA ON 44 SMALL CELL LUNG CANCER PATIENTS

| | | Serum Periostin | |
|---|---|---|---|
| Factors | No. of Patients | Periostin levels (ng/ml) | p-value |
| Mean age 51.3 ± 7.5 years | 44 | | 0.3579 $r^2 = 0.0202$* |
| Gender | | | |
| Male | 27 (61.4%) | 79.7 ± 12.5 | 0.3349 |
| Female | 17 (38.6%) | 68.2 ± 21.3 | |
| Tumor status | | | |
| T1 | 6 (14.0%) | 36.3 ± 7.5 | T4 vs T2 |
| T2 | 14 (31.8%) | 64.9 ± 16.1 | 0.0304 |
| T3 | 11 (25.0%) | 70.6 ± 15.0 | T4 vs T1 |
| T4 | 12 (27.3%) | 126.5 ± 29.7 | 0.0136 |
| Stage | | | |
| III | 32 (72.7%) | 84.9 ± 13.5 | 0.2641 |
| IV | 12 (27.3%) | 55.7 ± 17.0 | |
| Bone metastasis | | | |
| negative | 36 (81.8%) | 75.6 ± 12.7 | 0.4559 |
| positive | 8 (18.2%) | 88.6 ± 23.9 | |
| No. of metastasis sites | | | |
| one | 5 (41.7%) | 28.8 ± 7.6 | 0.4649 |
| more than two | 7 (58.3%) | 77.0 ± 26.8 | |
| Lymph node metastasis | | | |
| N0 | 2 (4.7%) | 14.0 ± 5.0 | N3 vs N2 |
| N2 | 18 (41.9%) | 49.7 ± 10.9 | 0.0091 |
| N3 | 23 (53.5%) | 108.7 ± 17.3 | |
| Performance status | | | |
| 0 | 9 (25.7%) | 59.9 ± 21.7 | NS |
| 1 | 22 (62.9%) | 66.7 ± 13.7 | |
| 2 | 4 (11.4%) | 104.5 ± 27.3 | |
| LDH 466.9 ± 291.2 U/l | 27 | | 0.6752 $r^2 = 0.0074$* |
| CEA 7.7 ± 16.7 ng/ml | 17 | | 0.7287 $r^2 = 0.088$* |

*Correlation with periostin levels for all patients monitored for this parameter
NS, not significant;
LDH, lactate dehydrogenase;
CEA, carcinoembryonic antigen The mean values for serum periostin in breast cancer patients were: at stage II, 56.1±14.3 ng/ml; at stage III, 28.0±4.7 ng/ml; and at stage IV, 85.3±20.5 ng/ml (Table 1). In normal healthy volunteers (n=20) a mean serum periostin level of 38.5±5.8 ng/ml was observed. No significant difference in serum periostin levels was found between these groups.

Patient groups were further stratified according to established prognostic factors. Serum periostin levels were elevated in breast cancer patients with bone metastases (89.3±21.8 ng/ml) compared to patients without evidence of bone metastasis (55.0±16.6 ng/ml; p=0.04) (Table 1). However, there were no significant differences in the serum periostin levels according to estrogen or progesterone receptor status (p=0.8359 and 0.9758, respectively), tumor grading (p=0.1890), menopausal status (p=0.4309), single vs. multiple metastatic sites (p=0.2546), the presence of lymph node metastases (p=0.5411), or the original tumor size (T) status (T1–T4). A T1 lung tumor is 3.0 cm or less in its greatest dimension, is surrounded by lung or visceral pleura, and is without evidence of invasion proximal to a lobar bronchus at bronchoscopy. A T2 lung tumor is greater than 3.0 cm in its greatest dimension or is a lung tumor of any size that either invades the visceral pleura or has associated atelactasis or obstructive pneumonitis extending to the hilar region. At bronchoscopy, the proximal extent of demonstrable tumor must be within a lobar bronchus or at least 2.0 cm distal to the carina. Any associated atelactasis or obstructive pneumonitis must involve less than entire lung. A T3 lung tumor is (a) a tumor of any size with direct extension into the chest wall (including the superior sulcus tumors), diaphragm, or the mediastinal pleura or pericardium without involving the heart, great vessels trachea, esophagus or vertebral body, or (b) a tumor in the main bronchus within 2 cm of carina without involving the carina, or associated atelactasis or obstructive pneumonitis of the entire lung. A T4 lung tumor is a tumor of any size with invasion of the mediastinum or involving heart, great vessels, trachea, esophagus, vertebral body, or carina or presence of malignant pleural or pericardial effusion, or with satellite tumor nodules within the ipsilateral, primary tumor lobe of the lung.

There was also no significant difference in periostin levels in HER-2-positive (n=4) vs. HER-2-negative (n=8) patients (p=0.3958) although sample size of patients studied was limited.

The mean serum periostin levels in patients with small cell lung cancer were 84.9±13.5 ng/ml for stage III and 55.7±17.0 ng/ml for stage IV patients (Table 2). There was no significant difference between stages of disease or between the patients and normal controls. Significant differences in serum periostin levels were seen, however, between patients with different T-status (tumor size status) and N-status (lymph node metastasis status). Serum periostin levels were elevated in T4 patients (126.5±29.7 ng/ml) compared to T2 (64.9±16.1 ng/ml, p=0.03) and T1 (36.3±7.5 ng/ml, p=0.01). The difference in serum periostin levels in patients with N3 status (108.7±17.3 ng/ml) was significantly different from those with N2 status (49.7±10.9 ng/ml, p=0.01). Serum periostin levels were not different in lung cancer patients with bone metastases (88.6±23.9 ng/ml) compared to patients who had no evidence of bone metastasis (75.6±12.7 ng/ml). There were also no significant differences in serum periostin levels according to parameters such as gender (p=0.3349), performance status (ability to carry out physical activity) (PS 0–2), or one metastatic site vs. two or more metastatic sites (p=0.4649). Periostin levels did not correlate with the levels of either lactate dehydrogenase (LDH) or carcinoembryonic antigen (CEA).

Example 5

Expression of Periostin mRNA in Normal Human Tissues

Periostin mRNA was detected by RT-PCR in RNA from the human lung, kidney and placenta. However, it was not detectable in RNA from human heart, liver, brain and skeletal muscle. The DNA sequences of RT-PCR products from lung, kidney and placenta revealed forms of human periostin cDNA that differed from that (OSF-2) cloned from osteosarcoma [Takeshita et al. (1993) Biochem. J. 294: 271–278]. The nucleotide sequence of cDNA (SEQ ID NO:1) encoding OSF-2 is shown in FIG. 1A and the amino acid sequence of OSF-2 (SEQ ID NO:2) is shown in FIG. 1B. Compared with OSF-2 cDNA, periostin cDNA cloned from placenta and lung had two deletions at residues 2009–2179 (171 base pairs, 57 amino acids) and residues 2360–2443 (84 base pairs, 28 amino acids), respectively. The nucleotide sequence of cDNA (SEQ ID NO:3) encoding this splice variant of periostin (designated periostin-L) is shown in FIG. 2A, and the amino acid sequence of periostin-L (SEQ ID NO:4) is shown in FIG. 2B. The nucleotide sequence of cDNA encoding the mature form of periostin-L (i.e., lacking nucleotides 1 to 63 of SEQ ID NO:3) is designated SEQ ID NO:5 and the amino acid sequence of mature periostin-L is designated SEQ ID NO:6. It is noted that nucleotide 2220 of SEQ ID NO:3 (and the corresponding nucleotide of SEQ ID NO:5) can be an A rather than a T residue. Periostin cDNA cloned from kidney had only one deletion at residues 2009–2179 (171 base pairs, 57 amino acids). The nucleotide sequence of cDNA (SEQ ID NO:7) encoding this splice variant of periostin (periostin-K) is shown in FIG. 3A, and the amino acid sequence of periostin-K (SEQ ID NO:8) is shown in FIG. 3B. The nucleotide sequence of cDNA encoding the mature form of periostin-K (i.e., lacking nucleotides 1 to 63 of SEQ ID NO:7) is designated SEQ ID NO:9, and the amino acid sequence of mature periostin-K is designated SEQ ID NO:10. It is noted that nucleotide 2304 of SEQ ID NO:7 (and the corresponding nucleotide of SEQ ID NO:9) can be an A rather than a T residue. All the above deletions are in-frame deletions. The periostin clones from placenta and lung lacked part of an $\alpha$-helix site (residues 2403–2466) that could be involved in attachment to the cell extracellular matrix. In situ hybridization revealed periostin mRNA localized in the stroma of normal placenta tissue.

Example 6

Serum Periostin Levels in Patients with Preeclampsia

The clinical characteristics of the study sample of women with preeclampsia and normal pregnant women are shown in Table 3. There was no significant difference in pre-pregnancy body weight, hematocrit, or placenta weight at delivery between the groups. As required by the classification criteria used in this study, significant differences between the groups with preeclampsia and the normal pregnant group were noted for both systolic and diastolic blood pressures.

A significant difference in the age was noted between the groups. The mean age at delivery in the group with preeclampsia was 29.8±1.2 years while that of normal pregnant group was 22.8±0.7 years. There was, however, no significant correlation between maternal periostin levels and age at delivery in either group. There was a significant statistical difference in the mean birth weight between the infants of the women with preeclampsia (2240.1±183.9 g) and those of normal pregnant women (3413.3±78.7 g). However, there was no significant correlation between maternal periostin levels and infant body weight.

Serum periostin concentrations were elevated in preeclampsia patients (311.8±56.3 ng/ml) compared to normal pregnant women at term (218.8±37.3 ng/ml). The mean serum periostin concentration for normal healthy nonpregnant volunteers (n=20) was previously found to be 38.5±6.1 ng/ml. Periostin concentrations in pregnant volunteers in the first trimester (n=58) were 77.5±13.7 ng/ml. Thus, serum periostin concentrations in preeclampsia patients and in normal pregnant women at term were elevated compared to nonpregnant (p=0.0001) and first trimester pregnant subjects (p=0.01). Concentrations in early pregnant and nonpregnant women were not significantly different. Other factors were also determined (Table 3). Serum TGF-$\beta$1 levels were higher in preeclampsia patients (8.0±0.3 ng/ml) than in normotensive pregnant women (7.2±0.3 ng/ml, p=0.0406).

However, TGF-β1 concentrations did not correlate with periostin concentrations (r=0.03, p=0.82). The concentrations of serum VCAM-1 (1.74±0.12 mg/ml vs. 1.28±0.07 mg/ml, p=0.0018) and E-selectin (50.4±4.3 ng/ml vs. 32.0±3.6 ng/ml, p=0.0007) significantly elevated in preeclampsia patients compared to normotensive pregnant women. Their levels also did not correlate with serum periostin levels. The level of interleukin-6 in serum of preeclampsia patients (0.86±0.17 ng/ml) was lower than in normal pregnant women (1.33±0.20 ng/ml), although the difference did not reach the level of significance selected. Interleukin-6 and periostin concentrations did not correlate.

TABLE 3

CLINICOPATHOLOGICAL DATA ON 30 PATIENTS WITH PREECLEMPSIA AND 30 NORMOTENSIVE PREGNANT WOMEN

| Factors | total 60 women (100%) | | |
|---|---|---|---|
| | preeclampsia 30 (50%) | normal 30 (50%) | p-value |
| Age at delivery (years) | 29.8 ± 1.2 | 22.8 ± 0.7 | 0.0001 |
| Body weight before pregnant (kg) | 67.9 ± 3.1 | 69.8 ± 1.2 | 0.7449 |
| Maternal predelivery hematocrit (%) | 36.1 ± 0.7 | 36.4 ± 0.6 | 0.5894 |
| Maternal predelivery Platelet | 182.6 ± 9.5 | 250.1 ± 14.9 | 0.0003 |
| Placenta weight (g) | 318.4 ± 19.0 | 438.3 ± 59.3 | 0.06 |
| Birth weight (g) | 2240.1 ± 183.9 | 3413.3 ± 78.7 | 0.0001 |
| Systolic blood pressure at delivery (mmHg) | 157.1 ± 2.0 | 121.3 ± 1.8 | 0.0001 |
| Diastolic blood pressure at delivery (mmHg) | 93.8 ± 1.4 | 72.2 ± 1.7 | 0.0001 |
| Maternal predelivery creatinine (mg/dL) | 0.85 ± 0.03 | 0.66 ± 0.05 | 0.01 |
| Gestational age at delivery (wk) | 35.1 ± 0.8 | 39.9 ± 0.3 | 0.0001 |
| Maternal predelivery uric acid | 6.7 ± 0.2 | 4.0 ± 0.2 | 0.0005 |
| Serum TGF-β1 levels correlation with periostin | 8.0 ± 0.3 | 7.2 ± 0.3 | 0.0406 0.82 r = 0.03 |
| Serum VCAM-1 levels correlation with periostin | 1.74 ± 0.12 | 1.28 ± 0.07 | 0.0018 0.5229 r = 0.085 |
| Serum E-selectin levels correlation with periostin | 50.5 ± 4.3 | 32.0 ± 3.6 | 0.0007 0.1852 r = 0.173 |
| Serum Interleukin-6 levels | 0.86 ± 0.17 | 1.33 ± 0.20 | 0.0591 0.5649 r = 0.076 |
| Serum Periostin levels (ng/ml) | 311.2 ± 56.3 | 218.8 ± 37.3 | 0.0385 |

Example 7

Isolation of TCG1 cDNA from Human Colon Carcinoma

TCG1 mRNA was initially identified as being overexpressed in human colon cancers (compared to normal colon tissue) using a palindromic PCR cDNA display technique. Briefly, paired mRNA preparations from human colon carcinoma tissue and from the adjacent normal colon tissue from the same patient were reverse transcribed and the resulting cDNA amplified by palindromic PCR. Amplified PCR cDNA fragments ($^{35}$S-labeled) were resolved on a polyacrymide electrophoretic gel. The cDNA patterns for tumor and normal tissue were similar, though one expressed cDNA fragment was identified to be dominant in the tumor tissue but not in the adjacent normal tissue. This cDNA fragment was recovered from the polyacrymide gel and then reamplified with the same primer (PP12) used for the cDNA display. The reamplified cDNA fragment was then cloned in the PCR2.1 TA cloning vector (Invitrogen, Groningen, Germany). Nucleotide sequence analysis revealed that this fragment contained 636 bp with the same PP12 primer at both 5'-ends of the double stranded cDNA.

The full-length cDNA was obtained by screening a human colon carcinoma-derived cDNA library (Lambda ZAP II) with the 636 bp TCG1 fragment as a probe. A full-length clone was found to have an open reading frame of 2313 bp encoding a 771 amino acid sequence with a predicted molecular weight of 85 kDa. The nucleotide sequence of cDNA encoding TCG1 (SEQ ID NO:11) is shown in FIG. 4A and the amino acid sequence of TCG1 (SEQ ID NO:12) is shown in FIG. 4B. TCG1 cDNA lacks nucleotides 2009–2089 and 2349–2432 of OSF-2 cDNA (SEQ ID NO:1). In addition, while OSF-2 cDNA has 6 A residues at positions 2472–2477, TCG1 cDNA has 7 A residues in the corresponding subsequence. Thus, TCG1 protein: (1) lacks amino acids 670–726 of SEQ ID NO:2 and has an arginine residue in place of this subsequence (due to the deletion of nucleotides 2009–2089 of SEQ ID NO:1); (2) lacks amino acids 783–810 of SEQ ID NO:2 (due to the deletion of nucleotides 2349–2432 of SEQ ID NO:1); and (3) replaces amino acid residues 823–836 of SEQ ID NO:2 with the amino acid sequence SSRI (SEQ ID NO:18) (due to the extra A residue in the TCG1 cDNA sequence, which results in a frame shift and a premature stop codon). Furthermore, the first nucleotide of last codon of the TCG1 coding region (SEQ ID NO:11) can be a T rather than an A. In this case, the last amino acid of TCG1 is F rather than I. Amino acid sequence analysis revealed that TCG1 contains an N-terminal signal peptide (SP) or secretory leader sequence, followed by a cysteine-rich domain (CRD), four internal homologous repeats (each about 135 amino acids in length) and a hydrophilic C-terminal domain (FIG. 5). It is in the hydrophilic C-terminal domain that heterogeneity between the periostin variants occurs. One chemokine B family motif (C-C) was found in the cysteine-rich domain at amino acid residues 79–80. The protein contains one predicted site of N-linked glycosylation (NDT) at amino acid residue 599–601. The signal peptide at the N-terminus and lack of a transmembrane domain suggest that it is a secreted protein. Western blot analysis of culture medium of cells expressing TCG1 confirmed that it is indeed a secreted protein. The nucleotide sequence of cDNA encoding mature TCG1 (i.e., lacking nucleotides 1 to 63 of SEQ ID NO:11) is designated SEQ ID NO:13 and mature TCG1 is designated SEQ ID NO:14.

A database search with the deduced amino acid sequence revealed that it is a splice variant of the human homologue of the mouse OSF-2 which was identified from MEC-3T3 osteoblast cells by substractive screening [Takeshita et al. (1993) Biochem J, 294:271–278]. Northern blot analysis revealed that this protein is not osteoblast specific. To avoid confusion of OSF-2 with the Osteoblast Specific Transcription Factor OSF2/Cbfa1, the protein was designated TCG1 (TGF-α- and TGF-β-regulated and Cancer-associated Gene 1). Further analysis indicated that the TCG1 has significant structural and sequence homology with βigH3, a TGF-β inducible gene initially identified from human lung carcinoma A5409 cells [Skonier et al. (1992) DNA Cell Biol, 11:511–522]. TCG1 shares 45.2% identity or 82.9% similarity with βigH3 at the amino acid level (DNAstar algorithm; Madison, Wis.). However, TCG1 contains an additional hydrophilic domain at the C-terminus. In addition, the βigH3 protein contains an RGD sequence at the C-terminus [Skonier et al. (1992) DNA Cell Biol, 11:511–522] that TCG1 does not contain. The amino acid sequence homology and structural similarity between TCG1 and βigH3 indicate their functional similarity. However, divergent amino acid sequences at the C-termini may reflect functional differences between the two proteins. Indeed, the expression patterns in various cell lines of TCG1 and βigH3 are very different. In addition, regulation of their expression by growth factors differs. Interestingly, both TCG1 and βigH3 share significant homology with Fasciclin I from Grasshopper and Drosophila [Bastiani et al. (1987) Cell, 48:745–755; Zinn et al. (1988) Cell, 53:577–587]. Fasciclin I is an extrinsic membrane glycoprotein involved in growth cone guidance during nervous system development in the insect embryo.

Example 8

Overexpression of TCG1 in Human Colon Carcinomas and Breast Cancers 27 pairs of total RNA samples separately isolated from human primary colon tumor tissue (T) and their adjacent normal colon tissue (N) were examined by Northern Blot analysis with a $^{32}$P-labeled TCG1 probe. In 24 of the 27 matched pairs, the TCG1 mRNA expression level was much greater in the tumor tissue than in the adjacent normal colon tissue. Further analysis of the expression pattern indicated that the T/N ratio (tumor/normal ratio) of TCG1 mRNA in the 27 cases ranged from 3.8 to 42. The mean T/N ratio was 16.5. To test for a possible correlation between the T/N ratio of TCG1 mRNA and the disease stage of colon cancer, the T/N ratios were plotted against the stages of disease. The data indicated no correlation between higher T/N ratios of TCG1 mRNA expression with later stages of the disease. However, in all 5 cases with recurrent colon cancer, the T/N ratios were significantly higher than the average. The T/N ratio in these 5 cases ranged from 22.4 to 42 (mean=29.6). This result suggested that high level of expression of TCG1 mRNA in tumor cells is associated with recurrence of the tumor. A higher frequency of tumor recurrence usually indicates stronger tumorigenicity of relevant cancer cells. Malignant colon carcinoma frequently metastasizes to the liver. To test the expression pattern of TCG1 mRNA in these metastatic colon tumors, six pairs of total RNA samples from metastatic colon carcinomas and their adjacent normal liver tissues were examined by Northern Blot analysis with a TCG1 cDNA probe. The level of TCG1 mRNA was much greater in the metastatic tumors than in the adjacent normal liver tissue in all 6 cases. Indeed, TCG1 mRNA was not detectable in normal liver tissue in 5 of the 6 cases studied.

Example 9

Increased Levels of Periostin in the Sera of a Panel of Lung Cancer Patients

The levels of periostin in the sera of 116 lung cancer (small cell lung carcinoma, non-small cell lung carcinoma, squamous cell carcinoma, and large cell carcinoma) patients were measured using a modification of the chemiluminescence assay described above. As in the assay described above, the 5H8 monoclonal antibody was used as a "capture" antibody. In contrast, however, the 8H11 monoclonal antibody (rather than the E17 polyclonal antibody) was used as a "detection" antibody. In the breast cancer study performed using the E17 polyclonal antibody as a detection antibody, a mean serum periostin level in a group of 20 normal subjects of 38.5±5.8 ng/ml was observed. On the other hand, using the 8H11 monoclonal antibody as a detection antibody in the study on lung cancer patients, sera from 76% of the patients gave chemiluminescence values not significantly different from values observed for assay wells to which assay buffer (instead of a serum sample) was added. Thus, the "normal" serum level of periostin, as measured in the assay using the 8H11 monoclonal antibody as a detection antibody, was essentially 0. Importantly, this assay was sufficiently sensitive to detect a serum periostin level of only 2 ng/ml (see patient no. 16 in Table 4 below)

Of the 116 lung cancer patients studied, 28 (24%) had significantly increased serum periostin levels. The serum periostin levels detected in these 28 patients are shown in Table 4. Of the 116 patients, 6 (5%) had serum periostin levels greater than 1,000 ng/ml and 22 (19%) had serum periostin levels of between 1 ng/ml and 400 ng/ml. Notably, all the patients with serum periostin levels higher than 1,000 ng/ml died within a year of initial testing. In contrast, those showing serum periostin levels between 1 ng/ml and 400 ng/ml, at least ten of whom were first tested more than a year before the time of writing, continue to be monitored at the time of writing.

TABLE 4

SERUM PERIOSTIN LEVELS IN 28 LUNG CANCER PATIENTS

| Patient No. | Serum periostin level (ng/ml) |
| --- | --- |
| 1 | >1,000 |
| 2 | >1,000 |
| 3 | >1,000 |
| 4 | >1,000 |
| 5 | >1,000 |
| 6 | >1,000 |
| 7 | 81 |
| 8 | 73 |
| 9 | 80 |
| 10 | 130 |
| 11 | 190 |
| 12 | 190 |
| 13 | 220 |
| 14 | 113 |
| 15 | 32 |
| 16 | 2 |
| 17 | 91 |
| 18 | 87 |
| 19 | 3 |
| 20 | 120 |
| 21 | 235 |
| 22 | 184 |
| 23 | 470 |
| 24 | 74 |
| 25 | 120 |
| 26 | 80 |
| 27 | 68 |
| 28 | 182 |

These data indicate that a body fluid (e.g., blood or urine) level of periostin can be a useful marker for lung cancer and that a high serum level (e.g., greater than 1,000 ng/ml) of periostin is indicative of a poor prognosis for lung cancer patients.

A number of embodiments of the invention have been described. Nevertheless, it will be understood that various modifications may be made without departing from the spirit and scope of the invention. Accordingly, the invention is limited only by the following claims.

What is claimed is:

1. A purified antibody that binds specifically to human periostin, wherein the antibody is the monoclonal antibody (mAb) secreted by hybridoma 5H8 having ATCC accession no. PTA-4589.

2. A purified antibody that binds specifically to human periostin, wherein the antibody is the mAb secreted by hybridoma 8H11 having ATCC accession no. PTA-4590.

3. A hybridoma that secretes a mAb that binds to human periostin, wherein the hybridoma is hybridoma 5H8 having ATCC accession no. PTA-4589.

4. A hybridoma that secretes a mAb that binds to human periostin, wherein the hybridoma is hybridoma 8H11 having ATCC accession no. PTA-4590.

* * * * *

SEQUENCE LISTING

<160> NUMBER OF SEQ ID NOS: 18

<210> SEQ ID NO 1
<211> LENGTH: 2508
<212> TYPE: DNA
<213> ORGANISM: Mus musculus
<220> FEATURE:
<221> NAME/KEY: CDS
<222> LOCATION: (1)...(2508)

<400> SEQUENCE: 1

```
atg att ccc ttt tta ccc atg ttt tct cta cta ttg ctg ctt att gtt      48
Met Ile Pro Phe Leu Pro Met Phe Ser Leu Leu Leu Leu Ile Val
  1               5                  10                  15 aac cct ata aac gcc aac aat cat tat gac aag atc ttg gct cat agt      96
Asn Pro Ile Asn Ala Asn Asn His Tyr Asp Lys Ile Leu Ala His Ser
                 20                  25                  30 cgt atc agg ggt cgg gac caa ggc cca aat gtc tgt gcc ctt caa cag     144
Arg Ile Arg Gly Arg Asp Gln Gly Pro Asn Val Cys Ala Leu Gln Gln
             35                  40                  45 att ttg ggc acc aaa aag aaa tac ttc agc act tgt aag aac tgg tat     192
Ile Leu Gly Thr Lys Lys Lys Tyr Phe Ser Thr Cys Lys Asn Trp Tyr
 50                  55                  60 aaa aag tcc atc tgt gga cag aaa acg act gtt tta tat gaa tgt tgc     240
Lys Lys Ser Ile Cys Gly Gln Lys Thr Thr Val Leu Tyr Glu Cys Cys
 65                  70                  75                  80 cct ggt tat atg aga atg gaa gga atg aaa ggc tgc cca gca gtt ttg     288
Pro Gly Tyr Met Arg Met Glu Gly Met Lys Gly Cys Pro Ala Val Leu
                 85                  90                  95 ccc att gac cat gtt tat ggc act ctg ggc atc gtg gga gcc acc aca     336
Pro Ile Asp His Val Tyr Gly Thr Leu Gly Ile Val Gly Ala Thr Thr
                100                 105                 110 acg cag cgc tat tct gac gcc tca aaa ctg agg gag gag atc gag gga     384
Thr Gln Arg Tyr Ser Asp Ala Ser Lys Leu Arg Glu Glu Ile Glu Gly
            115                 120                 125 aag gga tcc ttc act tac ttt gca ccg agt aat gag gct tgg gac aac     432
Lys Gly Ser Phe Thr Tyr Phe Ala Pro Ser Asn Glu Ala Trp Asp Asn
        130                 135                 140 ttg gat tct gat atc cgt aga ggt ttg gag agc aac gtg aat gtt gaa     480
Leu Asp Ser Asp Ile Arg Arg Gly Leu Glu Ser Asn Val Asn Val Glu
145                 150                 155                 160 tta ctg aat gct tta cat agt cac atg att aat aag aga atg ttg acc     528
Leu Leu Asn Ala Leu His Ser His Met Ile Asn Lys Arg Met Leu Thr
                165                 170                 175 aag gac tta aaa aat ggc atg att att cct tca atg tat aac aat ttg     576
Lys Asp Leu Lys Asn Gly Met Ile Ile Pro Ser Met Tyr Asn Asn Leu
            180                 185                 190 ggg ctt ttc att aac cat tat cct aat ggg gtt gtc act gtt aat tgt     624
Gly Leu Phe Ile Asn His Tyr Pro Asn Gly Val Val Thr Val Asn Cys
        195                 200                 205 gct cga atc atc cat ggg aac cag att gca aca aat ggt gtt gtc cat     672
Ala Arg Ile Ile His Gly Asn Gln Ile Ala Thr Asn Gly Val Val His
    210                 215                 220 gtc att gac cgt gtg ctt aca caa att ggt acc tca att caa gac ttc     720
Val Ile Asp Arg Val Leu Thr Gln Ile Gly Thr Ser Ile Gln Asp Phe
225                 230                 235                 240 att gaa gca gaa gat gac ctt tca tct ttt aga gca gct gcc atc aca     768
Ile Glu Ala Glu Asp Asp Leu Ser Ser Phe Arg Ala Ala Ala Ile Thr
                245                 250                 255
```

-continued

| | | |
|---|---|---|
| tcg gac ata ttg gag gcc ctt gga aga gac ggt cac ttc aca ctc ttt<br>Ser Asp Ile Leu Glu Ala Leu Gly Arg Asp Gly His Phe Thr Leu Phe<br>260 265 270 | | 816 |
| gct ccc acc aat gag gct ttt gag aaa ctt cca cga ggt gtc cta gaa<br>Ala Pro Thr Asn Glu Ala Phe Glu Lys Leu Pro Arg Gly Val Leu Glu<br>275 280 285 | | 864 |
| agg ttc atg gga gac aaa gtg gct tcc gaa gct ctt atg aag tac cac<br>Arg Phe Met Gly Asp Lys Val Ala Ser Glu Ala Leu Met Lys Tyr His<br>290 295 300 | | 912 |
| atc tta aat act ctc cag tgt tct gag tct att atg gga gga gca gtc<br>Ile Leu Asn Thr Leu Gln Cys Ser Glu Ser Ile Met Gly Gly Ala Val<br>305 310 315 320 | | 960 |
| ttt gag acg ctg gaa gga aat aca att gag ata gga tgt gac ggt gac<br>Phe Glu Thr Leu Glu Gly Asn Thr Ile Glu Ile Gly Cys Asp Gly Asp<br>325 330 335 | | 1008 |
| agt ata aca gta aat gga atc aaa atg gtg aac aaa aag gat att gtg<br>Ser Ile Thr Val Asn Gly Ile Lys Met Val Asn Lys Lys Asp Ile Val<br>340 345 350 | | 1056 |
| aca aat aat ggt gtg atc cat ttg att gat cag gtc cta att cct gat<br>Thr Asn Asn Gly Val Ile His Leu Ile Asp Gln Val Leu Ile Pro Asp<br>355 360 365 | | 1104 |
| tct gcc aaa caa gtt att gag ctg gct gga aaa cag caa acc acc ttc<br>Ser Ala Lys Gln Val Ile Glu Leu Ala Gly Lys Gln Gln Thr Thr Phe<br>370 375 380 | | 1152 |
| acg gat ctt gtg gcc caa tta ggc ttg gca tct gct ctg agg cca gat<br>Thr Asp Leu Val Ala Gln Leu Gly Leu Ala Ser Ala Leu Arg Pro Asp<br>385 390 395 400 | | 1200 |
| gga gaa tac act ttg ctg gca cct gtg aat aat gca ttt tct gat gat<br>Gly Glu Tyr Thr Leu Leu Ala Pro Val Asn Asn Ala Phe Ser Asp Asp<br>405 410 415 | | 1248 |
| act ctc agc atg gtt cag cgc ctc ctt aaa tta att ctg cag aat cac<br>Thr Leu Ser Met Val Gln Arg Leu Leu Lys Leu Ile Leu Gln Asn His<br>420 425 430 | | 1296 |
| ata ttg aaa gta aaa gtt ggc ctt aat gag ctt tac aac ggg caa ata<br>Ile Leu Lys Val Lys Val Gly Leu Asn Glu Leu Tyr Asn Gly Gln Ile<br>435 440 445 | | 1344 |
| ctg gaa acc atc gga ggc aaa cag ctc aga gtc ttc gta tat cgt aca<br>Leu Glu Thr Ile Gly Gly Lys Gln Leu Arg Val Phe Val Tyr Arg Thr<br>450 455 460 | | 1392 |
| gct gtc tgc att gaa aat tca tgc atg gag aaa ggg agt aag caa ggg<br>Ala Val Cys Ile Glu Asn Ser Cys Met Glu Lys Gly Ser Lys Gln Gly<br>465 470 475 480 | | 1440 |
| aga aac ggt gcg att cac ata ttc cgc gag atc atc aag cca gca gag<br>Arg Asn Gly Ala Ile His Ile Phe Arg Glu Ile Ile Lys Pro Ala Glu<br>485 490 495 | | 1488 |
| aaa tcc ctc cat gaa aag tta aaa caa gat aag cgc ttt agc acc ttc<br>Lys Ser Leu His Glu Lys Leu Lys Gln Asp Lys Arg Phe Ser Thr Phe<br>500 505 510 | | 1536 |
| ctc agc cta ctt gaa gct gca gac ttg aaa gag ctc ctg aca caa cct<br>Leu Ser Leu Leu Glu Ala Ala Asp Leu Lys Glu Leu Leu Thr Gln Pro<br>515 520 525 | | 1584 |
| gga gac tgg aca tta ttt gtg cca acc aat gat gct ttt aag gga atg<br>Gly Asp Trp Thr Leu Phe Val Pro Thr Asn Asp Ala Phe Lys Gly Met<br>530 535 540 | | 1632 |
| act agt gaa gaa aaa gaa att ctg ata cgg gac aaa aat gct ctt caa<br>Thr Ser Glu Glu Lys Glu Ile Leu Ile Arg Asp Lys Asn Ala Leu Gln<br>545 550 555 560 | | 1680 |
| aac atc att ctt tat cac ctg aca cca gga gtt ttc att gga aaa gga<br>Asn Ile Ile Leu Tyr His Leu Thr Pro Gly Val Phe Ile Gly Lys Gly<br>565 570 575 | | 1728 |

| | | |
|---|---|---|
| ttt gaa cct ggt gtt act aac att tta aag acc aca caa gga agc aaa<br>Phe Glu Pro Gly Val Thr Asn Ile Leu Lys Thr Thr Gln Gly Ser Lys<br>580 585 590 | | 1776 |
| atc ttt ctg aaa gaa gta aat gat aca ctt ctg gtg aat gaa ttg aaa<br>Ile Phe Leu Lys Glu Val Asn Asp Thr Leu Leu Val Asn Glu Leu Lys<br>595 600 605 | | 1824 |
| tca aaa gaa tct gac atc atg aca aca aat ggt gta att cat gtt gta<br>Ser Lys Glu Ser Asp Ile Met Thr Thr Asn Gly Val Ile His Val Val<br>610 615 620 | | 1872 |
| gat aaa ctc ctc tat cca gca gac aca cct gtt gga aat gat caa ctg<br>Asp Lys Leu Leu Tyr Pro Ala Asp Thr Pro Val Gly Asn Asp Gln Leu<br>625 630 635 640 | | 1920 |
| ctg gaa ata ctt aat aaa tta atc aaa tac atc caa att aag ttt gtt<br>Leu Glu Ile Leu Asn Lys Leu Ile Lys Tyr Ile Gln Ile Lys Phe Val<br>645 650 655 | | 1968 |
| cgt ggt agc acc ttc aaa gaa atc ccc gtg act gtc tat aca act aaa<br>Arg Gly Ser Thr Phe Lys Glu Ile Pro Val Thr Val Tyr Thr Thr Lys<br>660 665 670 | | 2016 |
| att ata acc aaa gtt gtg gaa cca aaa att aaa gtg att gaa ggc agt<br>Ile Ile Thr Lys Val Val Glu Pro Lys Ile Lys Val Ile Glu Gly Ser<br>675 680 685 | | 2064 |
| ctt cag cct att atc aaa act gaa gga ccc aca cta aca aaa gtc aaa<br>Leu Gln Pro Ile Ile Lys Thr Glu Gly Pro Thr Leu Thr Lys Val Lys<br>690 695 700 | | 2112 |
| att gaa ggt gaa cct gaa ttc aga ctg att aaa gaa ggt gaa aca ata<br>Ile Glu Gly Glu Pro Glu Phe Arg Leu Ile Lys Glu Gly Glu Thr Ile<br>705 710 715 720 | | 2160 |
| act gaa gtg atc cat gga gag cca att att aaa aaa tac acc aaa atc<br>Thr Glu Val Ile His Gly Glu Pro Ile Ile Lys Lys Tyr Thr Lys Ile<br>725 730 735 | | 2208 |
| att gat gga gtg cct gtg gaa ata act gaa aaa gag aca cga gaa gaa<br>Ile Asp Gly Val Pro Val Glu Ile Thr Glu Lys Glu Thr Arg Glu Glu<br>740 745 750 | | 2256 |
| cga atc att aca ggt cct gaa ata aaa tac act agg att tct act gga<br>Arg Ile Ile Thr Gly Pro Glu Ile Lys Tyr Thr Arg Ile Ser Thr Gly<br>755 760 765 | | 2304 |
| ggt gga gaa aca gaa gaa act ctg aag aaa ttg tta caa gaa gag gtc<br>Gly Gly Glu Thr Glu Glu Thr Leu Lys Lys Leu Leu Gln Glu Glu Val<br>770 775 780 | | 2352 |
| acc aag gtc acc aaa ttc att gaa ggt ggt gat ggt cat tta ttt gaa<br>Thr Lys Val Thr Lys Phe Ile Glu Gly Gly Asp Gly His Leu Phe Glu<br>785 790 795 800 | | 2400 |
| gat gaa gaa att aaa aga ctg ctt cag gga gac aca ccc gtg agg aag<br>Asp Glu Glu Ile Lys Arg Leu Leu Gln Gly Asp Thr Pro Val Arg Lys<br>805 810 815 | | 2448 |
| ttg caa gcc aac aaa aaa gtt caa ggt tct aga aga cga tta agg gaa<br>Leu Gln Ala Asn Lys Lys Val Gln Gly Ser Arg Arg Arg Leu Arg Glu<br>820 825 830 | | 2496 |
| ggt cgt tct cag<br>Gly Arg Ser Gln<br>835 | | 2508 |

<210> SEQ ID NO 2
<211> LENGTH: 836
<212> TYPE: PRT
<213> ORGANISM: Mus musculus

<400> SEQUENCE: 2

Met Ile Pro Phe Leu Pro Met Phe Ser Leu Leu Leu Leu Ile Val
1               5                   10                  15

-continued

```
Asn Pro Ile Asn Ala Asn Asn His Tyr Asp Lys Ile Leu Ala His Ser
             20                  25                  30
Arg Ile Arg Gly Arg Asp Gln Gly Pro Asn Val Cys Ala Leu Gln Gln
         35                  40                  45
Ile Leu Gly Thr Lys Lys Tyr Phe Ser Thr Cys Lys Asn Trp Tyr
 50                  55                  60
Lys Lys Ser Ile Cys Gly Gln Lys Thr Thr Val Leu Tyr Glu Cys Cys
 65                  70                  75                  80
Pro Gly Tyr Met Arg Met Glu Gly Met Lys Gly Cys Pro Ala Val Leu
                 85                  90                  95
Pro Ile Asp His Val Tyr Gly Thr Leu Gly Ile Val Gly Ala Thr Thr
            100                 105                 110
Thr Gln Arg Tyr Ser Asp Ala Ser Lys Leu Arg Glu Glu Ile Glu Gly
            115                 120                 125
Lys Gly Ser Phe Thr Tyr Phe Ala Pro Ser Asn Glu Ala Trp Asp Asn
130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
            195                 200                 205
Ala Arg Ile Ile His Gly Asn Gln Ile Ala Thr Asn Gly Val Val His
            210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ile Thr
                245                 250                 255
Ser Asp Ile Leu Glu Ala Leu Gly Arg Asp Gly His Phe Thr Leu Phe
            260                 265                 270
Ala Pro Thr Asn Glu Ala Phe Glu Lys Leu Pro Arg Gly Val Leu Glu
            275                 280                 285
Arg Phe Met Gly Asp Lys Val Ala Ser Glu Ala Leu Met Lys Tyr His
            290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Lys Asp Ile Val
            340                 345                 350
Thr Asn Asn Gly Val Ile His Leu Ile Asp Gln Val Leu Ile Pro Asp
            355                 360                 365
Ser Ala Lys Gln Val Ile Glu Leu Ala Gly Lys Gln Gln Thr Thr Phe
            370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Val Gln Arg Leu Leu Lys Leu Ile Leu Gln Asn His
            420                 425                 430
```

-continued

```
Ile Leu Lys Val Lys Gly Leu Asn Glu Leu Tyr Asn Gly Gln Ile
        435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
        610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
                660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
        690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
                740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
        770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Leu Arg Glu
        820                 825                 830

Gly Arg Ser Gln
        835
```

-continued

<210> SEQ ID NO 3
<211> LENGTH: 2253
<212> TYPE: DNA
<213> ORGANISM: Homo sapiens
<220> FEATURE:
<221> NAME/KEY: CDS
<222> LOCATION: (1)...(2253)

<400> SEQUENCE: 3

| | | | | | | | | | | | | | | | | |
|---|---|---|---|---|---|---|---|---|---|---|---|---|---|---|---|---|
| atg | att | ccc | ttt | tta | ccc | atg | ttt | tct | cta | cta | ttg | ctg | ctt | att | gtt | 48 |
| Met | Ile | Pro | Phe | Leu | Pro | Met | Phe | Ser | Leu | Leu | Leu | Leu | Leu | Ile | Val | |
| 1 | | | | 5 | | | | | 10 | | | | | 15 | | |
| aac | cct | ata | aac | gcc | aac | aat | cat | tat | gac | aag | atc | ttg | gct | cat | agt | 96 |
| Asn | Pro | Ile | Asn | Ala | Asn | Asn | His | Tyr | Asp | Lys | Ile | Leu | Ala | His | Ser | |
| | | | 20 | | | | | 25 | | | | | 30 | | | |
| cgt | atc | agg | ggt | cgg | gac | caa | ggc | cca | aat | gtc | tgt | gcc | ctt | caa | cag | 144 |
| Arg | Ile | Arg | Gly | Arg | Asp | Gln | Gly | Pro | Asn | Val | Cys | Ala | Leu | Gln | Gln | |
| | | 35 | | | | | 40 | | | | | 45 | | | | |
| att | ttg | ggc | acc | aaa | aag | aaa | tac | ttc | agc | act | tgt | aag | aac | tgg | tat | 192 |
| Ile | Leu | Gly | Thr | Lys | Lys | Lys | Tyr | Phe | Ser | Thr | Cys | Lys | Asn | Trp | Tyr | |
| 50 | | | | | 55 | | | | | 60 | | | | | | |
| aaa | aag | tcc | atc | tgt | gga | cag | aaa | acg | act | gtt | tta | tat | gaa | tgt | tgc | 240 |
| Lys | Lys | Ser | Ile | Cys | Gly | Gln | Lys | Thr | Thr | Val | Leu | Tyr | Glu | Cys | Cys | |
| 65 | | | | | 70 | | | | | 75 | | | | | 80 | |
| cct | ggt | tat | atg | aga | atg | gaa | gga | atg | aaa | ggc | tgc | cca | gca | gtt | ttg | 288 |
| Pro | Gly | Tyr | Met | Arg | Met | Glu | Gly | Met | Lys | Gly | Cys | Pro | Ala | Val | Leu | |
| | | | | 85 | | | | | 90 | | | | | 95 | | |
| ccc | att | gac | cat | gtt | tat | ggc | act | ctg | ggc | atc | gtg | gga | gcc | acc | aca | 336 |
| Pro | Ile | Asp | His | Val | Tyr | Gly | Thr | Leu | Gly | Ile | Val | Gly | Ala | Thr | Thr | |
| | | | 100 | | | | | 105 | | | | | 110 | | | |
| acg | cag | cgc | tat | tct | gac | gcc | tca | aaa | ctg | agg | gag | gag | atc | gag | gga | 384 |
| Thr | Gln | Arg | Tyr | Ser | Asp | Ala | Ser | Lys | Leu | Arg | Glu | Glu | Ile | Glu | Gly | |
| | | 115 | | | | | 120 | | | | | 125 | | | | |
| aag | gga | tcc | ttc | act | tac | ttt | gca | ccg | agt | aat | gag | gct | tgg | gac | aac | 432 |
| Lys | Gly | Ser | Phe | Thr | Tyr | Phe | Ala | Pro | Ser | Asn | Glu | Ala | Trp | Asp | Asn | |
| | 130 | | | | | 135 | | | | | 140 | | | | | |
| ttg | gat | tct | gat | atc | cgt | aga | ggt | ttg | gag | agc | aac | gtg | aat | gtt | gaa | 480 |
| Leu | Asp | Ser | Asp | Ile | Arg | Arg | Gly | Leu | Glu | Ser | Asn | Val | Asn | Val | Glu | |
| 145 | | | | | 150 | | | | | 155 | | | | | 160 | |
| tta | ctg | aat | gct | tta | cat | agt | cac | atg | att | aat | aag | aga | atg | ttg | acc | 528 |
| Leu | Leu | Asn | Ala | Leu | His | Ser | His | Met | Ile | Asn | Lys | Arg | Met | Leu | Thr | |
| | | | | 165 | | | | | 170 | | | | | 175 | | |
| aag | gac | tta | aaa | aat | ggc | atg | att | att | cct | tca | atg | tat | aac | aat | ttg | 576 |
| Lys | Asp | Leu | Lys | Asn | Gly | Met | Ile | Ile | Pro | Ser | Met | Tyr | Asn | Asn | Leu | |
| | | | 180 | | | | | 185 | | | | | 190 | | | |
| ggg | ctt | ttc | att | aac | cat | tat | cct | aat | ggg | gtt | gtc | act | gtt | aat | tgt | 624 |
| Gly | Leu | Phe | Ile | Asn | His | Tyr | Pro | Asn | Gly | Val | Val | Thr | Val | Asn | Cys | |
| | | 195 | | | | | 200 | | | | | 205 | | | | |
| gct | cga | atc | atc | cat | ggg | aac | cag | att | gca | aca | aat | ggt | gtt | gtc | cat | 672 |
| Ala | Arg | Ile | Ile | His | Gly | Asn | Gln | Ile | Ala | Thr | Asn | Gly | Val | Val | His | |
| | 210 | | | | | 215 | | | | | 220 | | | | | |
| gtc | att | gac | cgt | gtg | ctt | aca | caa | att | ggt | acc | tca | att | caa | gac | ttc | 720 |
| Val | Ile | Asp | Arg | Val | Leu | Thr | Gln | Ile | Gly | Thr | Ser | Ile | Gln | Asp | Phe | |
| 225 | | | | | 230 | | | | | 235 | | | | | 240 | |
| att | gaa | gca | gaa | gat | gac | ctt | tca | tct | ttt | aga | gca | gct | gcc | atc | aca | 768 |
| Ile | Glu | Ala | Glu | Asp | Asp | Leu | Ser | Ser | Phe | Arg | Ala | Ala | Ala | Ile | Thr | |
| | | | | 245 | | | | | 250 | | | | | 255 | | |
| tcg | gac | ata | ttg | gag | gcc | ctt | gga | aga | gac | ggt | cac | ttc | aca | ctc | ttt | 816 |
| Ser | Asp | Ile | Leu | Glu | Ala | Leu | Gly | Arg | Asp | Gly | His | Phe | Thr | Leu | Phe | |
| | | | 260 | | | | | 265 | | | | | 270 | | | |
| gct | ccc | acc | aat | gag | gct | ttt | gag | aaa | ctt | cca | cga | ggt | gtc | cta | gaa | 864 |

|  |  |
|---|---|
| Ala Pro Thr Asn Glu Ala Phe Glu Lys Leu Pro Arg Gly Val Leu Glu<br>    275                          280                  285 |  |
| agg ttc atg gga gac aaa gtg gct tcc gaa gct ctt atg aag tac cac<br>Arg Phe Met Gly Asp Lys Val Ala Ser Glu Ala Leu Met Lys Tyr His<br>    290                        295                300 | 912 |
| atc tta aat act ctc cag tgt tct gag tct att atg gga gga gca gtc<br>Ile Leu Asn Thr Leu Gln Cys Ser Glu Ser Ile Met Gly Gly Ala Val<br>305                310                315                320 | 960 |
| ttt gag acg ctg gaa gga aat aca att gag ata gga tgt gac ggt gac<br>Phe Glu Thr Leu Glu Gly Asn Thr Ile Glu Ile Gly Cys Asp Gly Asp<br>                      325                330              335 | 1008 |
| agt ata aca gta aat gga atc aaa atg gtg aac aaa aag gat att gtg<br>Ser Ile Thr Val Asn Gly Ile Lys Met Val Asn Lys Lys Asp Ile Val<br>                340                345              350 | 1056 |
| aca aat aat ggt gtg atc cat ttg att gat cag gtc cta att cct gat<br>Thr Asn Asn Gly Val Ile His Leu Ile Asp Gln Val Leu Ile Pro Asp<br>              355                360              365 | 1104 |
| tct gcc aaa caa gtt att gag ctg gct gga aaa cag caa acc acc ttc<br>Ser Ala Lys Gln Val Ile Glu Leu Ala Gly Lys Gln Gln Thr Thr Phe<br>370                375                380 | 1152 |
| acg gat ctt gtg gcc caa tta ggc ttg gca tct gct ctg agg cca gat<br>Thr Asp Leu Val Ala Gln Leu Gly Leu Ala Ser Ala Leu Arg Pro Asp<br>385                390                395              400 | 1200 |
| gga gaa tac act ttg ctg gca cct gtg aat aat gca ttt tct gat gat<br>Gly Glu Tyr Thr Leu Leu Ala Pro Val Asn Asn Ala Phe Ser Asp Asp<br>                      405                410              415 | 1248 |
| act ctc agc atg gtt cag cgc ctc ctt aaa tta att ctg cag aat cac<br>Thr Leu Ser Met Val Gln Arg Leu Leu Lys Leu Ile Leu Gln Asn His<br>              420                425              430 | 1296 |
| ata ttg aaa gta aaa gtt ggc ctt aat gag ctt tac aac ggg caa ata<br>Ile Leu Lys Val Lys Val Gly Leu Asn Glu Leu Tyr Asn Gly Gln Ile<br>              435                440              445 | 1344 |
| ctg gaa acc atc gga ggc aaa cag ctc aga gtc ttc gta tat cgt aca<br>Leu Glu Thr Ile Gly Gly Lys Gln Leu Arg Val Phe Val Tyr Arg Thr<br>    450                        455                460 | 1392 |
| gct gtc tgc att gaa aat tca tgc atg gag aaa ggg agt aag caa ggg<br>Ala Val Cys Ile Glu Asn Ser Cys Met Glu Lys Gly Ser Lys Gln Gly<br>465                470                475              480 | 1440 |
| aga aac ggt gcg att cac ata ttc cgc gag atc atc aag cca gca gag<br>Arg Asn Gly Ala Ile His Ile Phe Arg Glu Ile Ile Lys Pro Ala Glu<br>                      485                490              495 | 1488 |
| aaa tcc ctc cat gaa aag tta aaa caa gat aag cgc ttt agc acc ttc<br>Lys Ser Leu His Glu Lys Leu Lys Gln Asp Lys Arg Phe Ser Thr Phe<br>              500                505              510 | 1536 |
| ctc agc cta ctt gaa gct gca gac ttg aaa gag ctc ctg aca caa cct<br>Leu Ser Leu Leu Glu Ala Ala Asp Leu Lys Glu Leu Leu Thr Gln Pro<br>              515                520              525 | 1584 |
| gga gac tgg aca tta ttt gtg cca acc aat gat gct ttt aag gga atg<br>Gly Asp Trp Thr Leu Phe Val Pro Thr Asn Asp Ala Phe Lys Gly Met<br>    530                        535                540 | 1632 |
| act agt gaa gaa aaa gaa att ctg ata cgg gac aaa aat gct ctt caa<br>Thr Ser Glu Glu Lys Glu Ile Leu Ile Arg Asp Lys Asn Ala Leu Gln<br>545                550                555              560 | 1680 |
| aac atc att ctt tat cac ctg aca cca gga gtt ttc att gga aaa gga<br>Asn Ile Ile Leu Tyr His Leu Thr Pro Gly Val Phe Ile Gly Lys Gly<br>                      565                570              575 | 1728 |
| ttt gaa cct ggt gtt act aac att tta aag acc aca caa gga agc aaa<br>Phe Glu Pro Gly Val Thr Asn Ile Leu Lys Thr Thr Gln Gly Ser Lys<br>              580                585              590 | 1776 |

-continued

| | | |
|---|---|---|
| atc ttt ctg aaa gaa gta aat gat aca ctt ctg gtg aat gaa ttg aaa<br>Ile Phe Leu Lys Glu Val Asn Asp Thr Leu Leu Val Asn Glu Leu Lys<br>595                                600                            605 | 1824 |

```
atc ttt ctg aaa gaa gta aat gat aca ctt ctg gtg aat gaa ttg aaa      1824
Ile Phe Leu Lys Glu Val Asn Asp Thr Leu Leu Val Asn Glu Leu Lys
595                 600                 605 tca aaa gaa tct gac atc atg aca aca aat ggt gta att cat gtt gta      1872
Ser Lys Glu Ser Asp Ile Met Thr Thr Asn Gly Val Ile His Val Val
    610                 615                 620 gat aaa ctc ctc tat cca gca gac aca cct gtt gga aat gat caa ctg      1920
Asp Lys Leu Leu Tyr Pro Ala Asp Thr Pro Val Gly Asn Asp Gln Leu
625                 630                 635                 640 ctg gaa ata ctt aat aaa tta atc aaa tac atc caa att aag ttt gtt      1968
Leu Glu Ile Leu Asn Lys Leu Ile Lys Tyr Ile Gln Ile Lys Phe Val
                645                 650                 655 cgt ggt agc acc ttc aaa gaa atc ccc gtg act gtc tat aag cca att      2016
Arg Gly Ser Thr Phe Lys Glu Ile Pro Val Thr Val Tyr Lys Pro Ile
            660                 665                 670 att aaa aaa tac acc aaa atc att gat gga gtg cct gtg gaa ata act      2064
Ile Lys Lys Tyr Thr Lys Ile Ile Asp Gly Val Pro Val Glu Ile Thr
        675                 680                 685 gaa aaa gag aca cga gaa gaa cga atc att aca ggt cct gaa ata aaa      2112
Glu Lys Glu Thr Arg Glu Glu Arg Ile Ile Thr Gly Pro Glu Ile Lys
    690                 695                 700 tac act agg att tct act gga ggt gga gaa aca gaa gaa act ctg aag      2160
Tyr Thr Arg Ile Ser Thr Gly Gly Gly Glu Thr Glu Glu Thr Leu Lys
705                 710                 715                 720 aaa ttg tta caa gaa gag gtc acc aag ggg aag ttg caa gcc aac aaa      2208
Lys Leu Leu Gln Glu Glu Val Thr Lys Gly Lys Leu Gln Ala Asn Lys
                725                 730                 735 aaa gtt caa ggt tct aga aga cga tta agg gaa ggt cgt tct cag          2253
Lys Val Gln Gly Ser Arg Arg Arg Leu Arg Glu Gly Arg Ser Gln
            740                 745                 750
```

<210> SEQ ID NO 4
<211> LENGTH: 751
<212> TYPE: PRT
<213> ORGANISM: Homo sapiens

<400> SEQUENCE: 4

```
Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
```

-continued

```
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
        195                 200                 205
Ala Arg Ile Ile His Gly Asn Gln Ile Ala Thr Asn Gly Val Val His
    210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ile Thr
                245                 250                 255
Ser Asp Ile Leu Glu Ala Leu Gly Arg Asp Gly His Phe Thr Leu Phe
            260                 265                 270
Ala Pro Thr Asn Glu Ala Phe Glu Lys Leu Pro Arg Gly Val Leu Glu
        275                 280                 285
Arg Phe Met Gly Asp Lys Val Ala Ser Glu Ala Leu Met Lys Tyr His
    290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Asp Ile Val
            340                 345                 350
Thr Asn Asn Gly Val Ile His Leu Ile Asp Gln Val Leu Ile Pro Asp
        355                 360                 365
Ser Ala Lys Gln Val Ile Glu Leu Ala Gly Lys Gln Gln Thr Thr Phe
    370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Val Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Thr Gln Pro
        515                 520                 525
Gly Asp Trp Thr Leu Phe Val Pro Thr Asn Asp Ala Phe Lys Gly Met
    530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
```

```
Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Arg Ile Ile Thr Gly Pro Glu Ile Lys
    690                 695                 700

Tyr Thr Arg Ile Ser Thr Gly Gly Glu Thr Glu Thr Leu Lys
705                 710                 715                 720

Lys Leu Leu Gln Glu Glu Val Thr Lys Gly Lys Leu Gln Ala Asn Lys
                725                 730                 735

Lys Val Gln Gly Ser Arg Arg Arg Leu Arg Glu Gly Arg Ser Gln
            740                 745                 750
```

<210> SEQ ID NO 5
<211> LENGTH: 2190
<212> TYPE: DNA
<213> ORGANISM: Homo sapiens
<220> FEATURE:
<221> NAME/KEY: CDS
<222> LOCATION: (1)...(2190)

<400> SEQUENCE: 5

```
aac aat cat tat gac aag atc ttg gct cat agt cgt atc agg ggt cgg      48
Asn Asn His Tyr Asp Lys Ile Leu Ala His Ser Arg Ile Arg Gly Arg
  1               5                  10                  15 gac caa ggc cca aat gtc tgt gcc ctt caa cag att ttg ggc acc aaa      96
Asp Gln Gly Pro Asn Val Cys Ala Leu Gln Gln Ile Leu Gly Thr Lys
             20                  25                  30 aag aaa tac ttc agc act tgt aag aac tgg tat aaa aag tcc atc tgt     144
Lys Lys Tyr Phe Ser Thr Cys Lys Asn Trp Tyr Lys Lys Ser Ile Cys
         35                  40                  45 gga cag aaa acg act gtt tta tat gaa tgt tgc cct ggt tat atg aga     192
Gly Gln Lys Thr Thr Val Leu Tyr Glu Cys Cys Pro Gly Tyr Met Arg
     50                  55                  60 atg gaa gga atg aaa ggc tgc cca gca gtt ttg ccc att gac cat gtt     240
Met Glu Gly Met Lys Gly Cys Pro Ala Val Leu Pro Ile Asp His Val
 65                  70                  75                  80 tat ggc act ctg ggc atc gtg gga gcc acc aca acg cag cgc tat tct     288
Tyr Gly Thr Leu Gly Ile Val Gly Ala Thr Thr Thr Gln Arg Tyr Ser
                 85                  90                  95 gac gcc tca aaa ctg agg gag gag atc gag gga aag gga tcc ttc act     336
Asp Ala Ser Lys Leu Arg Glu Glu Ile Glu Gly Lys Gly Ser Phe Thr
            100                 105                 110 tac ttt gca ccg agt aat gag gct tgg gac aac ttg gat tct gat atc     384
Tyr Phe Ala Pro Ser Asn Glu Ala Trp Asp Asn Leu Asp Ser Asp Ile
        115                 120                 125 cgt aga ggt ttg gag agc aac gtg aat gtt gaa tta ctg aat gct tta     432
Arg Arg Gly Leu Glu Ser Asn Val Asn Val Glu Leu Leu Asn Ala Leu
    130                 135                 140 cat agt cac atg att aat aag aga atg ttg acc aag gac tta aaa aat     480
```

```
His Ser His Met Ile Asn Lys Arg Met Leu Thr Lys Asp Leu Lys Asn
145                 150                 155                 160 ggc atg att att cct tca atg tat aac aat ttg ggg ctt ttc att aac       528
Gly Met Ile Ile Pro Ser Met Tyr Asn Asn Leu Gly Leu Phe Ile Asn
                165                 170                 175 cat tat cct aat ggg gtt gtc act gtt aat tgt gct cga atc atc cat       576
His Tyr Pro Asn Gly Val Val Thr Val Asn Cys Ala Arg Ile Ile His
            180                 185                 190 ggg aac cag att gca aca aat ggt gtt gtc cat gtc att gac cgt gtg       624
Gly Asn Gln Ile Ala Thr Asn Gly Val Val His Val Ile Asp Arg Val
        195                 200                 205 ctt aca caa att ggt acc tca att caa gac ttc att gaa gca gaa gat       672
Leu Thr Gln Ile Gly Thr Ser Ile Gln Asp Phe Ile Glu Ala Glu Asp
    210                 215                 220 gac ctt tca tct ttt aga gca gct gcc atc aca tcg gac ata ttg gag       720
Asp Leu Ser Ser Phe Arg Ala Ala Ala Ile Thr Ser Asp Ile Leu Glu
225                 230                 235                 240 gcc ctt gga aga gac ggt cac ttc aca ctc ttt gct ccc acc aat gag       768
Ala Leu Gly Arg Asp Gly His Phe Thr Leu Phe Ala Pro Thr Asn Glu
                245                 250                 255 gct ttt gag aaa ctt cca cga ggt gtc cta gaa agg ttc atg gga gac       816
Ala Phe Glu Lys Leu Pro Arg Gly Val Leu Glu Arg Phe Met Gly Asp
            260                 265                 270 aaa gtg gct tcc gaa gct ctt atg aag tac cac atc tta aat act ctc       864
Lys Val Ala Ser Glu Ala Leu Met Lys Tyr His Ile Leu Asn Thr Leu
        275                 280                 285 cag tgt tct gag tct att atg gga gga gca gtc ttt gag acg ctg gaa       912
Gln Cys Ser Glu Ser Ile Met Gly Gly Ala Val Phe Glu Thr Leu Glu
    290                 295                 300 gga aat aca att gag ata gga tgt gac ggt gac agt ata aca gta aat       960
Gly Asn Thr Ile Glu Ile Gly Cys Asp Gly Asp Ser Ile Thr Val Asn
305                 310                 315                 320 gga atc aaa atg gtg aac aaa aag gat att gtg aca aat aat ggt gtg      1008
Gly Ile Lys Met Val Asn Lys Lys Asp Ile Val Thr Asn Asn Gly Val
                325                 330                 335 atc cat ttg att gat cag gtc cta att cct gat tct gcc aaa caa gtt      1056
Ile His Leu Ile Asp Gln Val Leu Ile Pro Asp Ser Ala Lys Gln Val
            340                 345                 350 att gag ctg gct gga aaa cag caa acc acc ttc acg gat ctt gtg gcc      1104
Ile Glu Leu Ala Gly Lys Gln Gln Thr Thr Phe Thr Asp Leu Val Ala
        355                 360                 365 caa tta ggc ttg gca tct gct ctg agg cca gat gga gaa tac act ttg      1152
Gln Leu Gly Leu Ala Ser Ala Leu Arg Pro Asp Gly Glu Tyr Thr Leu
    370                 375                 380 ctg gca cct gtg aat aat gca ttt tct gat gat act ctc agc atg gtt      1200
Leu Ala Pro Val Asn Asn Ala Phe Ser Asp Asp Thr Leu Ser Met Val
385                 390                 395                 400 cag cgc ctc ctt aaa tta att ctg cag aat cac ata ttg aaa gta aaa      1248
Gln Arg Leu Leu Lys Leu Ile Leu Gln Asn His Ile Leu Lys Val Lys
                405                 410                 415 gtt ggc ctt aat gag ctt tac aac ggg caa ata ctg gaa acc atc gga      1296
Val Gly Leu Asn Glu Leu Tyr Asn Gly Gln Ile Leu Glu Thr Ile Gly
            420                 425                 430 ggc aaa cag ctc aga gtc ttc gta tat cgt aca gct gtc tgc att gaa      1344
Gly Lys Gln Leu Arg Val Phe Val Tyr Arg Thr Ala Val Cys Ile Glu
        435                 440                 445 aat tca tgc atg gag aaa ggg agt aag caa ggg aga aac ggt gcg att      1392
Asn Ser Cys Met Glu Lys Gly Ser Lys Gln Gly Arg Asn Gly Ala Ile
    450                 455                 460
```

-continued

```
cac ata ttc cgc gag atc atc aag cca gca gag aaa tcc ctc cat gaa    1440
His Ile Phe Arg Glu Ile Ile Lys Pro Ala Glu Lys Ser Leu His Glu
465                 470                 475                 480 aag tta aaa caa gat aag cgc ttt agc acc ttc ctc agc cta ctt gaa    1488
Lys Leu Lys Gln Asp Lys Arg Phe Ser Thr Phe Leu Ser Leu Leu Glu
            485                 490                 495 gct gca gac ttg aaa gag ctc ctg aca caa cct gga gac tgg aca tta    1536
Ala Ala Asp Leu Lys Glu Leu Leu Thr Gln Pro Gly Asp Trp Thr Leu
        500                 505                 510 ttt gtg cca acc aat gat gct ttt aag gga atg act agt gaa gaa aaa    1584
Phe Val Pro Thr Asn Asp Ala Phe Lys Gly Met Thr Ser Glu Glu Lys
    515                 520                 525 gaa att ctg ata cgg gac aaa aat gct ctt caa aac atc att ctt tat    1632
Glu Ile Leu Ile Arg Asp Lys Asn Ala Leu Gln Asn Ile Ile Leu Tyr
530                 535                 540 cac ctg aca cca gga gtt ttc att gga aaa gga ttt gaa cct ggt gtt    1680
His Leu Thr Pro Gly Val Phe Ile Gly Lys Gly Phe Glu Pro Gly Val
545                 550                 555                 560 act aac att tta aag acc aca caa gga agc aaa atc ttt ctg aaa gaa    1728
Thr Asn Ile Leu Lys Thr Thr Gln Gly Ser Lys Ile Phe Leu Lys Glu
            565                 570                 575 gta aat gat aca ctt ctg gtg aat gaa ttg aaa tca aaa gaa tct gac    1776
Val Asn Asp Thr Leu Leu Val Asn Glu Leu Lys Ser Lys Glu Ser Asp
        580                 585                 590 atc atg aca aca aat ggt gta att cat gtt gta gat aaa ctc ctc tat    1824
Ile Met Thr Thr Asn Gly Val Ile His Val Val Asp Lys Leu Leu Tyr
    595                 600                 605 cca gca gac aca cct gtt gga aat gat caa ctg ctg gaa ata ctt aat    1872
Pro Ala Asp Thr Pro Val Gly Asn Asp Gln Leu Leu Glu Ile Leu Asn
610                 615                 620 aaa tta atc aaa tac atc caa att aag ttt gtt cgt ggt agc acc ttc    1920
Lys Leu Ile Lys Tyr Ile Gln Ile Lys Phe Val Arg Gly Ser Thr Phe
625                 630                 635                 640 aaa gaa atc ccc gtg act gtc tat aag cca att att aaa aaa tac acc    1968
Lys Glu Ile Pro Val Thr Val Tyr Lys Pro Ile Ile Lys Lys Tyr Thr
            645                 650                 655 aaa atc att gat gga gtg cct gtg gaa ata act gaa aaa gag aca cga    2016
Lys Ile Ile Asp Gly Val Pro Val Glu Ile Thr Glu Lys Glu Thr Arg
        660                 665                 670 gaa gaa cga atc att aca ggt cct gaa ata aaa tac act agg att tct    2064
Glu Glu Arg Ile Ile Thr Gly Pro Glu Ile Lys Tyr Thr Arg Ile Ser
    675                 680                 685 act gga ggt gga gaa aca gaa gaa act ctg aag aaa ttg tta caa gaa    2112
Thr Gly Gly Gly Glu Thr Glu Glu Thr Leu Lys Lys Leu Leu Gln Glu
690                 695                 700 gag gtc acc aag ggg aag ttg caa gcc aac aaa aaa gtt caa ggt tct    2160
Glu Val Thr Lys Gly Lys Leu Gln Ala Asn Lys Lys Val Gln Gly Ser
705                 710                 715                 720 aga aga cga tta agg gaa ggt cgt tct cag                            2190
Arg Arg Arg Leu Arg Glu Gly Arg Ser Gln
            725                 730
```

<210> SEQ ID NO 6
<211> LENGTH: 730
<212> TYPE: PRT
<213> ORGANISM: Homo sapiens

<400> SEQUENCE: 6

Asn Asn His Tyr Asp Lys Ile Leu Ala His Ser Arg Ile Arg Gly Arg
1               5                   10                  15

```
Asp Gln Gly Pro Asn Val Cys Ala Leu Gln Gln Ile Leu Gly Thr Lys
        20              25              30

Lys Lys Tyr Phe Ser Thr Cys Lys Asn Trp Tyr Lys Lys Ser Ile Cys
        35              40              45

Gly Gln Lys Thr Thr Val Leu Tyr Glu Cys Cys Pro Gly Tyr Met Arg
        50              55              60

Met Glu Gly Met Lys Gly Cys Pro Ala Val Leu Pro Ile Asp His Val
65              70              75              80

Tyr Gly Thr Leu Gly Ile Val Gly Ala Thr Thr Gln Arg Tyr Ser
                85              90              95

Asp Ala Ser Lys Leu Arg Glu Glu Ile Glu Gly Lys Gly Ser Phe Thr
            100             105             110

Tyr Phe Ala Pro Ser Asn Glu Ala Trp Asp Asn Leu Asp Ser Asp Ile
        115             120             125

Arg Arg Gly Leu Glu Ser Asn Val Asn Val Glu Leu Leu Asn Ala Leu
130             135             140

His Ser His Met Ile Asn Lys Arg Met Leu Thr Lys Asp Leu Lys Asn
145             150             155             160

Gly Met Ile Ile Pro Ser Met Tyr Asn Asn Leu Gly Leu Phe Ile Asn
                165             170             175

His Tyr Pro Asn Gly Val Val Thr Val Asn Cys Ala Arg Ile Ile His
            180             185             190

Gly Asn Gln Ile Ala Thr Asn Gly Val Val His Val Ile Asp Arg Val
            195             200             205

Leu Thr Gln Ile Gly Thr Ser Ile Gln Asp Phe Ile Glu Ala Glu Asp
        210             215             220

Asp Leu Ser Ser Phe Arg Ala Ala Ile Thr Ser Asp Ile Leu Glu
225             230             235             240

Ala Leu Gly Arg Asp Gly His Phe Thr Leu Phe Ala Pro Thr Asn Glu
            245             250             255

Ala Phe Glu Lys Leu Pro Arg Gly Val Leu Glu Arg Phe Met Gly Asp
        260             265             270

Lys Val Ala Ser Glu Ala Leu Met Lys Tyr His Ile Leu Asn Thr Leu
        275             280             285

Gln Cys Ser Glu Ser Ile Met Gly Gly Ala Val Phe Glu Thr Leu Glu
        290             295             300

Gly Asn Thr Ile Glu Ile Gly Cys Asp Gly Asp Ser Ile Thr Val Asn
305             310             315             320

Gly Ile Lys Met Val Asn Lys Lys Asp Ile Val Thr Asn Asn Gly Val
            325             330             335

Ile His Leu Ile Asp Gln Val Leu Ile Pro Asp Ser Ala Lys Gln Val
            340             345             350

Ile Glu Leu Ala Gly Lys Gln Gln Thr Thr Phe Thr Asp Leu Val Ala
        355             360             365

Gln Leu Gly Leu Ala Ser Ala Leu Arg Pro Asp Gly Glu Tyr Thr Leu
        370             375             380

Leu Ala Pro Val Asn Asn Ala Phe Ser Asp Asp Thr Leu Ser Met Val
385             390             395             400

Gln Arg Leu Leu Lys Leu Ile Leu Gln Asn His Ile Leu Lys Val Lys
            405             410             415

Val Gly Leu Asn Glu Leu Tyr Asn Gly Gln Ile Leu Glu Thr Ile Gly
            420             425             430

Gly Lys Gln Leu Arg Val Phe Val Tyr Arg Thr Ala Val Cys Ile Glu
```

```
                435                 440                 445
Asn Ser Cys Met Glu Lys Gly Ser Lys Gln Gly Arg Asn Gly Ala Ile
            450                 455                 460

His Ile Phe Arg Glu Ile Ile Lys Pro Ala Glu Lys Ser Leu His Glu
465                 470                 475                 480

Lys Leu Lys Gln Asp Lys Arg Phe Ser Thr Phe Leu Ser Leu Leu Glu
                485                 490                 495

Ala Ala Asp Leu Lys Glu Leu Leu Thr Gln Pro Gly Asp Trp Thr Leu
            500                 505                 510

Phe Val Pro Thr Asn Asp Ala Phe Lys Gly Met Thr Ser Glu Glu Lys
        515                 520                 525

Glu Ile Leu Ile Arg Asp Lys Asn Ala Leu Gln Asn Ile Ile Leu Tyr
    530                 535                 540

His Leu Thr Pro Gly Val Phe Ile Gly Lys Gly Phe Glu Pro Gly Val
545                 550                 555                 560

Thr Asn Ile Leu Lys Thr Thr Gln Gly Ser Lys Ile Phe Leu Lys Glu
                565                 570                 575

Val Asn Asp Thr Leu Leu Val Asn Glu Leu Lys Ser Lys Glu Ser Asp
            580                 585                 590

Ile Met Thr Thr Asn Gly Val Ile His Val Val Asp Lys Leu Leu Tyr
        595                 600                 605

Pro Ala Asp Thr Pro Val Gly Asn Asp Gln Leu Leu Glu Ile Leu Asn
    610                 615                 620

Lys Leu Ile Lys Tyr Ile Gln Ile Lys Phe Val Arg Gly Ser Thr Phe
625                 630                 635                 640

Lys Glu Ile Pro Val Thr Val Tyr Lys Pro Ile Ile Lys Lys Tyr Thr
                645                 650                 655

Lys Ile Ile Asp Gly Val Pro Val Glu Ile Thr Glu Lys Glu Thr Arg
            660                 665                 670

Glu Glu Arg Ile Ile Thr Gly Pro Glu Ile Lys Tyr Thr Arg Ile Ser
        675                 680                 685

Thr Gly Gly Gly Glu Thr Glu Glu Thr Leu Lys Lys Leu Leu Gln Glu
    690                 695                 700

Glu Val Thr Lys Gly Lys Leu Gln Ala Asn Lys Lys Val Gln Gly Ser
705                 710                 715                 720

Arg Arg Arg Leu Arg Glu Gly Arg Ser Gln
                725                 730

<210> SEQ ID NO 7
<211> LENGTH: 2337
<212> TYPE: DNA
<213> ORGANISM: Homo sapiens
<220> FEATURE:
<221> NAME/KEY: CDS
<222> LOCATION: (1)...(2337)

<400> SEQUENCE: 7 atg att ccc ttt tta ccc atg ttt tct cta cta ttg ctg ctt att gtt     48
Met Ile Pro Phe Leu Pro Met Phe Ser Leu Leu Leu Leu Ile Val
 1               5                  10                  15 aac cct ata aac gcc aac aat cat tat gac aag atc ttg gct cat agt     96
Asn Pro Ile Asn Ala Asn Asn His Tyr Asp Lys Ile Leu Ala His Ser
                20                  25                  30 cgt atc agg ggt cgg gac caa ggc cca aat gtc tgt gcc ctt caa cag    144
Arg Ile Arg Gly Arg Asp Gln Gly Pro Asn Val Cys Ala Leu Gln Gln
        35                  40                  45
```

-continued

| | | |
|---|---|---|
| att ttg ggc acc aaa aag aaa tac ttc agc act tgt aag aac tgg tat<br>Ile Leu Gly Thr Lys Lys Lys Tyr Phe Ser Thr Cys Lys Asn Trp Tyr<br>50          55                  60 | 192 | |
| aaa aag tcc atc tgt gga cag aaa acg act gtt tta tat gaa tgt tgc<br>Lys Lys Ser Ile Cys Gly Gln Lys Thr Thr Val Leu Tyr Glu Cys Cys<br>65          70              75              80 | 240 | |
| cct ggt tat atg aga atg gaa gga atg aaa ggc tgc cca gca gtt ttg<br>Pro Gly Tyr Met Arg Met Glu Gly Met Lys Gly Cys Pro Ala Val Leu<br>85              90              95 | 288 | |
| ccc att gac cat gtt tat ggc act ctg ggc atc gtg gga gcc acc aca<br>Pro Ile Asp His Val Tyr Gly Thr Leu Gly Ile Val Gly Ala Thr Thr<br>100              105              110 | 336 | |
| acg cag cgc tat tct gac gcc tca aaa ctg agg gag gag atc gag gga<br>Thr Gln Arg Tyr Ser Asp Ala Ser Lys Leu Arg Glu Glu Ile Glu Gly<br>115              120              125 | 384 | |
| aag gga tcc ttc act tac ttt gca ccg agt aat gag gct tgg gac aac<br>Lys Gly Ser Phe Thr Tyr Phe Ala Pro Ser Asn Glu Ala Trp Asp Asn<br>130              135              140 | 432 | |
| ttg gat tct gat atc cgt aga ggt ttg gag agc aac gtg aat gtt gaa<br>Leu Asp Ser Asp Ile Arg Arg Gly Leu Glu Ser Asn Val Asn Val Glu<br>145          150              155              160 | 480 | |
| tta ctg aat gct tta cat agt cac atg att aat aag aga atg ttg acc<br>Leu Leu Asn Ala Leu His Ser His Met Ile Asn Lys Arg Met Leu Thr<br>165              170              175 | 528 | |
| aag gac tta aaa aat ggc atg att att cct tca atg tat aac aat ttg<br>Lys Asp Leu Lys Asn Gly Met Ile Ile Pro Ser Met Tyr Asn Asn Leu<br>180              185              190 | 576 | |
| ggg ctt ttc att aac cat tat cct aat ggg gtt gtc act gtt aat tgt<br>Gly Leu Phe Ile Asn His Tyr Pro Asn Gly Val Val Thr Val Asn Cys<br>195              200              205 | 624 | |
| gct cga atc atc cat ggg aac cag att gca aca aat ggt gtt gtc cat<br>Ala Arg Ile Ile His Gly Asn Gln Ile Ala Thr Asn Gly Val Val His<br>210              215              220 | 672 | |
| gtc att gac cgt gtg ctt aca caa att ggt acc tca att caa gac ttc<br>Val Ile Asp Arg Val Leu Thr Gln Ile Gly Thr Ser Ile Gln Asp Phe<br>225          230              235              240 | 720 | |
| att gaa gca gaa gat gac ctt tca tct ttt aga gca gct gcc atc aca<br>Ile Glu Ala Glu Asp Asp Leu Ser Ser Phe Arg Ala Ala Ala Ile Thr<br>245              250              255 | 768 | |
| tcg gac ata ttg gag gcc ctt gga aga gac ggt cac ttc aca ctc ttt<br>Ser Asp Ile Leu Glu Ala Leu Gly Arg Asp Gly His Phe Thr Leu Phe<br>260              265              270 | 816 | |
| gct ccc acc aat gag gct ttt gag aaa ctt cca cga ggt gtc cta gaa<br>Ala Pro Thr Asn Glu Ala Phe Glu Lys Leu Pro Arg Gly Val Leu Glu<br>275              280              285 | 864 | |
| agg ttc atg gga gac aaa gtg gct tcc gaa gct ctt atg aag tac cac<br>Arg Phe Met Gly Asp Lys Val Ala Ser Glu Ala Leu Met Lys Tyr His<br>290              295              300 | 912 | |
| atc tta aat act ctc cag tgt tct gag tct att atg gga gga gca gtc<br>Ile Leu Asn Thr Leu Gln Cys Ser Glu Ser Ile Met Gly Gly Ala Val<br>305              310              315              320 | 960 | |
| ttt gag acg ctg gaa gga aat aca att gag ata gga tgt gac ggt gac<br>Phe Glu Thr Leu Glu Gly Asn Thr Ile Glu Ile Gly Cys Asp Gly Asp<br>325              330              335 | 1008 | |
| agt ata aca gta aat gga atc aaa atg gtg aac aaa aag gat att gtg<br>Ser Ile Thr Val Asn Gly Ile Lys Met Val Asn Lys Lys Asp Ile Val<br>340              345              350 | 1056 | |
| aca aat aat ggt gtg atc cat ttg att gat cag gtc cta att cct gat<br>Thr Asn Asn Gly Val Ile His Leu Ile Asp Gln Val Leu Ile Pro Asp<br>355              360              365 | 1104 | |

-continued

| | | |
|---|---|---|
| tct gcc aaa caa gtt att gag ctg gct gga aaa cag caa acc acc ttc<br>Ser Ala Lys Gln Val Ile Glu Leu Ala Gly Lys Gln Gln Thr Thr Phe<br>370                      375                        380 | 1152 |
| acg gat ctt gtg gcc caa tta ggc ttg gca tct gct ctg agg cca gat<br>Thr Asp Leu Val Ala Gln Leu Gly Leu Ala Ser Ala Leu Arg Pro Asp<br>385                      390                        395                    400 | 1200 |
| gga gaa tac act ttg ctg gca cct gtg aat aat gca ttt tct gat gat<br>Gly Glu Tyr Thr Leu Leu Ala Pro Val Asn Asn Ala Phe Ser Asp Asp<br>                        405                        410                        415 | 1248 |
| act ctc agc atg gtt cag cgc ctc ctt aaa tta att ctg cag aat cac<br>Thr Leu Ser Met Val Gln Arg Leu Leu Lys Leu Ile Leu Gln Asn His<br>                  420                        425                        430 | 1296 |
| ata ttg aaa gta aaa gtt ggc ctt aat gag ctt tac aac ggg caa ata<br>Ile Leu Lys Val Lys Val Gly Leu Asn Glu Leu Tyr Asn Gly Gln Ile<br>                        435                        440                        445 | 1344 |
| ctg gaa acc atc gga ggc aaa cag ctc aga gtc ttc gta tat cgt aca<br>Leu Glu Thr Ile Gly Gly Lys Gln Leu Arg Val Phe Val Tyr Arg Thr<br>450                      455                        460 | 1392 |
| gct gtc tgc att gaa aat tca tgc atg gag aaa ggg agt aag caa ggg<br>Ala Val Cys Ile Glu Asn Ser Cys Met Glu Lys Gly Ser Lys Gln Gly<br>465                      470                        475                    480 | 1440 |
| aga aac ggt gcg att cac ata ttc cgc gag atc atc aag cca gca gag<br>Arg Asn Gly Ala Ile His Ile Phe Arg Glu Ile Ile Lys Pro Ala Glu<br>                        485                        490                        495 | 1488 |
| aaa tcc ctc cat gaa aag tta aaa caa gat aag cgc ttt agc acc ttc<br>Lys Ser Leu His Glu Lys Leu Lys Gln Asp Lys Arg Phe Ser Thr Phe<br>                  500                        505                        510 | 1536 |
| ctc agc cta ctt gaa gct gca gac ttg aaa gag ctc ctg aca caa cct<br>Leu Ser Leu Leu Glu Ala Ala Asp Leu Lys Glu Leu Leu Thr Gln Pro<br>                        515                        520                        525 | 1584 |
| gga gac tgg aca tta ttt gtg cca acc aat gat gct ttt aag gga atg<br>Gly Asp Trp Thr Leu Phe Val Pro Thr Asn Asp Ala Phe Lys Gly Met<br>530                      535                        540 | 1632 |
| act agt gaa gaa aaa gaa att ctg ata cgg gac aaa aat gct ctt caa<br>Thr Ser Glu Glu Lys Glu Ile Leu Ile Arg Asp Lys Asn Ala Leu Gln<br>545                      550                        555                    560 | 1680 |
| aac atc att ctt tat cac ctg aca cca gga gtt ttc att gga aaa gga<br>Asn Ile Ile Leu Tyr His Leu Thr Pro Gly Val Phe Ile Gly Lys Gly<br>                        565                        570                        575 | 1728 |
| ttt gaa cct ggt gtt act aac att tta aag acc aca caa gga agc aaa<br>Phe Glu Pro Gly Val Thr Asn Ile Leu Lys Thr Thr Gln Gly Ser Lys<br>                  580                        585                        590 | 1776 |
| atc ttt ctg aaa gaa gta aat gat aca ctt ctg gtg aat gaa ttg aaa<br>Ile Phe Leu Lys Glu Val Asn Asp Thr Leu Leu Val Asn Glu Leu Lys<br>                        595                        600                        605 | 1824 |
| tca aaa gaa tct gac atc atg aca aca aat ggt gta att cat gtt gta<br>Ser Lys Glu Ser Asp Ile Met Thr Thr Asn Gly Val Ile His Val Val<br>610                      615                        620 | 1872 |
| gat aaa ctc ctc tat cca gca gac aca cct gtt gga aat gat caa ctg<br>Asp Lys Leu Leu Tyr Pro Ala Asp Thr Pro Val Gly Asn Asp Gln Leu<br>625                      630                        635                    640 | 1920 |
| ctg gaa ata ctt aat aaa tta atc aaa tac atc caa att aag ttt gtt<br>Leu Glu Ile Leu Asn Lys Leu Ile Lys Tyr Ile Gln Ile Lys Phe Val<br>                        645                        650                        655 | 1968 |
| cgt ggt agc acc ttc aaa gaa atc ccc gtg act gtc tat aag cca att<br>Arg Gly Ser Thr Phe Lys Glu Ile Pro Val Thr Val Tyr Lys Pro Ile<br>                        660                        665                        670 | 2016 |
| att aaa aaa tac acc aaa atc att gat gga gtg cct gtg gaa ata act<br>Ile Lys Lys Tyr Thr Lys Ile Ile Asp Gly Val Pro Val Glu Ile Thr | 2064 |

|   |   |   |   |   |   |   |   |   |   |   |   |   |   |   |   |      |
|---|---|---|---|---|---|---|---|---|---|---|---|---|---|---|---|------|
|   |   | 675 |   |   |   | 680 |   |   |   | 685 |   |   |   |   |   |      |
| gaa | aaa | gag | aca | cga | gaa | gaa | cga | atc | att | aca | ggt | cct | gaa | ata | aaa | 2112 |
| Glu | Lys | Glu | Thr | Arg | Glu | Glu | Arg | Ile | Ile | Thr | Gly | Pro | Glu | Ile | Lys |      |
|   | 690 |   |   |   |   | 695 |   |   |   |   | 700 |   |   |   |   |      |
| tac | act | agg | att | tct | act | gga | ggt | gga | gaa | aca | gaa | gaa | act | ctg | aag | 2160 |
| Tyr | Thr | Arg | Ile | Ser | Thr | Gly | Gly | Gly | Glu | Thr | Glu | Glu | Thr | Leu | Lys |      |
| 705 |   |   |   |   | 710 |   |   |   |   | 715 |   |   |   |   | 720 |      |
| aaa | ttg | tta | caa | gaa | gag | gtc | acc | aag | gtc | acc | aaa | ttc | att | gaa | ggt | 2208 |
| Lys | Leu | Leu | Gln | Glu | Glu | Val | Thr | Lys | Val | Thr | Lys | Phe | Ile | Glu | Gly |      |
|   |   |   |   | 725 |   |   |   |   | 730 |   |   |   |   | 735 |   |      |
| ggt | gat | ggt | cat | tta | ttt | gaa | gat | gaa | gaa | att | aaa | aga | ctg | ctt | cag | 2256 |
| Gly | Asp | Gly | His | Leu | Phe | Glu | Asp | Glu | Glu | Ile | Lys | Arg | Leu | Leu | Gln |      |
|   |   |   | 740 |   |   |   |   | 745 |   |   |   |   | 750 |   |   |      |
| gga | gac | aca | ccc | gtg | agg | aag | ttg | caa | gcc | aac | aaa | aaa | gtt | caa | ggt | 2304 |
| Gly | Asp | Thr | Pro | Val | Arg | Lys | Leu | Gln | Ala | Asn | Lys | Lys | Val | Gln | Gly |      |
|   |   | 755 |   |   |   |   | 760 |   |   |   |   | 765 |   |   |   |      |
| tct | aga | aga | cga | tta | agg | gaa | ggt | cgt | tct | cag |   |   |   |   |   | 2337 |
| Ser | Arg | Arg | Arg | Leu | Arg | Glu | Gly | Arg | Ser | Gln |   |   |   |   |   |      |
| 770 |   |   |   |   | 775 |   |   |   |   |   |   |   |   |   |   |      |

<210> SEQ ID NO 8
<211> LENGTH: 779
<212> TYPE: PRT
<213> ORGANISM: Homo sapiens

<400> SEQUENCE: 8

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

-continued

```
Ile Glu Ala Glu Asp Asp Leu Ser Ser Phe Arg Ala Ala Ile Thr
                245                 250                 255
Ser Asp Ile Leu Glu Ala Leu Gly Arg Asp Gly His Phe Thr Leu Phe
        260                 265                 270
Ala Pro Thr Asn Glu Ala Phe Glu Lys Leu Pro Arg Gly Val Leu Glu
        275                 280                 285
Arg Phe Met Gly Asp Lys Val Ala Ser Glu Ala Leu Met Lys Tyr His
    290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Lys Asp Ile Val
                340                 345                 350
Thr Asn Asn Gly Val Ile His Leu Ile Asp Gln Val Leu Ile Pro Asp
            355                 360                 365
Ser Ala Lys Gln Val Ile Glu Leu Ala Gly Lys Gln Gln Thr Thr Phe
    370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Val Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Leu Thr Gln Pro
        515                 520                 525
Gly Asp Trp Thr Leu Phe Val Pro Thr Asn Asp Ala Phe Lys Gly Met
    530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
Ser Lys Glu Ser Asp Ile Met Thr Thr Asn Gly Val Ile His Val Val
    610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Lys Pro Ile
```

```
                      660                 665                 670
Ile Lys Lys Tyr Thr Lys Ile Ile Asp Gly Val Pro Val Glu Ile Thr
            675                 680                 685

Glu Lys Glu Thr Arg Glu Arg Ile Ile Thr Gly Pro Glu Ile Lys
        690                 695                 700

Tyr Thr Arg Ile Ser Thr Gly Gly Glu Thr Glu Thr Leu Lys
705                 710                 715                 720

Lys Leu Leu Gln Glu Glu Val Thr Lys Val Thr Lys Phe Ile Glu Gly
                725                 730                 735

Gly Asp Gly His Leu Phe Glu Asp Glu Ile Lys Arg Leu Leu Gln
            740                 745                 750

Gly Asp Thr Pro Val Arg Lys Leu Gln Ala Asn Lys Lys Val Gln Gly
            755                 760                 765

Ser Arg Arg Arg Leu Arg Glu Gly Arg Ser Gln
            770                 775

<210> SEQ ID NO 9
<211> LENGTH: 2274
<212> TYPE: DNA
<213> ORGANISM: Homo sapiens
<220> FEATURE:
<221> NAME/KEY: CDS
<222> LOCATION: (1)...(2274)

<400> SEQUENCE: 9 aac aat cat tat gac aag atc ttg gct cat agt cgt atc agg ggt cgg     48
Asn Asn His Tyr Asp Lys Ile Leu Ala His Ser Arg Ile Arg Gly Arg
  1               5                  10                  15 gac caa ggc cca aat gtc tgt gcc ctt caa cag att ttg ggc acc aaa     96
Asp Gln Gly Pro Asn Val Cys Ala Leu Gln Gln Ile Leu Gly Thr Lys
             20                  25                  30 aag aaa tac ttc agc act tgt aag aac tgg tat aaa aag tcc atc tgt    144
Lys Lys Tyr Phe Ser Thr Cys Lys Asn Trp Tyr Lys Lys Ser Ile Cys
         35                  40                  45 gga cag aaa acg act gtt tta tat gaa tgt tgc cct ggt tat atg aga    192
Gly Gln Lys Thr Thr Val Leu Tyr Glu Cys Cys Pro Gly Tyr Met Arg
     50                  55                  60 atg gaa gga atg aaa ggc tgc cca gca gtt ttg ccc att gac cat gtt    240
Met Glu Gly Met Lys Gly Cys Pro Ala Val Leu Pro Ile Asp His Val
 65                  70                  75                  80 tat ggc act ctg ggc atc gtg gga gcc acc aca acg cag cgc tat tct    288
Tyr Gly Thr Leu Gly Ile Val Gly Ala Thr Thr Thr Gln Arg Tyr Ser
                 85                  90                  95 gac gcc tca aaa ctg agg gag gag atc gag gga aag gga tcc ttc act    336
Asp Ala Ser Lys Leu Arg Glu Glu Ile Glu Gly Lys Gly Ser Phe Thr
            100                 105                 110 tac ttt gca ccg agt aat gag gct tgg gac aac ttg gat tct gat atc    384
Tyr Phe Ala Pro Ser Asn Glu Ala Trp Asp Asn Leu Asp Ser Asp Ile
        115                 120                 125 cgt aga ggt ttg gag agc aac gtg aat gtt gaa tta ctg aat gct tta    432
Arg Arg Gly Leu Glu Ser Asn Val Asn Val Glu Leu Leu Asn Ala Leu
    130                 135                 140 cat agt cac atg att aat aag aga atg ttg acc aag gac tta aaa aat    480
His Ser His Met Ile Asn Lys Arg Met Leu Thr Lys Asp Leu Lys Asn
145                 150                 155                 160 ggc atg att att cct tca atg tat aac aat ttg ggg ctt ttc att aac    528
Gly Met Ile Ile Pro Ser Met Tyr Asn Asn Leu Gly Leu Phe Ile Asn
                165                 170                 175 cat tat cct aat ggg gtt gtc act gtt aat tgt gct cga atc atc cat    576
```

```
His Tyr Pro Asn Gly Val Val Thr Val Asn Cys Ala Arg Ile Ile His
            180                 185                 190 ggg aac cag att gca aca aat ggt gtt gtc cat gtc att gac cgt gtg       624
Gly Asn Gln Ile Ala Thr Asn Gly Val Val His Val Ile Asp Arg Val
        195                 200                 205 ctt aca caa att ggt acc tca att caa gac ttc att gaa gca gaa gat       672
Leu Thr Gln Ile Gly Thr Ser Ile Gln Asp Phe Ile Glu Ala Glu Asp
    210                 215                 220 gac ctt tca tct ttt aga gca gct gcc atc aca tcg gac ata ttg gag       720
Asp Leu Ser Ser Phe Arg Ala Ala Ala Ile Thr Ser Asp Ile Leu Glu
225                 230                 235                 240 gcc ctt gga aga gac ggt cac ttc aca ctc ttt gct ccc acc aat gag       768
Ala Leu Gly Arg Asp Gly His Phe Thr Leu Phe Ala Pro Thr Asn Glu
                245                 250                 255 gct ttt gag aaa ctt cca cga ggt gtc cta gaa agg ttc atg gga gac       816
Ala Phe Glu Lys Leu Pro Arg Gly Val Leu Glu Arg Phe Met Gly Asp
            260                 265                 270 aaa gtg gct tcc gaa gct ctt atg aag tac cac atc tta aat act ctc       864
Lys Val Ala Ser Glu Ala Leu Met Lys Tyr His Ile Leu Asn Thr Leu
        275                 280                 285 cag tgt tct gag tct att atg gga gga gca gtc ttt gag acg ctg gaa       912
Gln Cys Ser Glu Ser Ile Met Gly Gly Ala Val Phe Glu Thr Leu Glu
    290                 295                 300 gga aat aca att gag ata gga tgt gac ggt gac agt ata aca gta aat       960
Gly Asn Thr Ile Glu Ile Gly Cys Asp Gly Asp Ser Ile Thr Val Asn
305                 310                 315                 320 gga atc aaa atg gtg aac aaa aag gat att gtg aca aat aat ggt gtg      1008
Gly Ile Lys Met Val Asn Lys Lys Asp Ile Val Thr Asn Asn Gly Val
                325                 330                 335 atc cat ttg att gat cag gtc cta att cct gat tct gcc aaa caa gtt      1056
Ile His Leu Ile Asp Gln Val Leu Ile Pro Asp Ser Ala Lys Gln Val
            340                 345                 350 att gag ctg gct gga aaa cag caa acc acc ttc acg gat ctt gtg gcc      1104
Ile Glu Leu Ala Gly Lys Gln Gln Thr Thr Phe Thr Asp Leu Val Ala
        355                 360                 365 caa tta ggc ttg gca tct gct ctg agg cca gat gga gaa tac act ttg      1152
Gln Leu Gly Leu Ala Ser Ala Leu Arg Pro Asp Gly Glu Tyr Thr Leu
    370                 375                 380 ctg gca cct gtg aat aat gca ttt tct gat gat act ctc agc atg gtt      1200
Leu Ala Pro Val Asn Asn Ala Phe Ser Asp Asp Thr Leu Ser Met Val
385                 390                 395                 400 cag cgc ctc ctt aaa tta att ctg cag aat cac ata ttg aaa gta aaa      1248
Gln Arg Leu Leu Lys Leu Ile Leu Gln Asn His Ile Leu Lys Val Lys
                405                 410                 415 gtt ggc ctt aat gag ctt tac aac ggg caa ata ctg gaa acc atc gga      1296
Val Gly Leu Asn Glu Leu Tyr Asn Gly Gln Ile Leu Glu Thr Ile Gly
            420                 425                 430 ggc aaa cag ctc aga gtc ttc gta tat cgt aca gct gtc tgc att gaa      1344
Gly Lys Gln Leu Arg Val Phe Val Tyr Arg Thr Ala Val Cys Ile Glu
        435                 440                 445 aat tca tgc atg gag aaa ggg agt aag caa ggg aga aac ggt gcg att      1392
Asn Ser Cys Met Glu Lys Gly Ser Lys Gln Gly Arg Asn Gly Ala Ile
    450                 455                 460 cac ata ttc cgc gag atc atc aag cca gca gag aaa tcc ctc cat gaa      1440
His Ile Phe Arg Glu Ile Ile Lys Pro Ala Glu Lys Ser Leu His Glu
465                 470                 475                 480 aag tta aaa caa gat aag cgc ttt agc acc ttc ctc agc cta ctt gaa      1488
Lys Leu Lys Gln Asp Lys Arg Phe Ser Thr Phe Leu Ser Leu Leu Glu
                485                 490                 495
```

-continued

| | | |
|---|---|---|
| gct gca gac ttg aaa gag ctc ctg aca caa cct gga gac tgg aca tta<br>Ala Ala Asp Leu Lys Glu Leu Leu Thr Gln Pro Gly Asp Trp Thr Leu<br>           500                   505                  510 | 1536 |
| ttt gtg cca acc aat gat gct ttt aag gga atg act agt gaa gaa aaa<br>Phe Val Pro Thr Asn Asp Ala Phe Lys Gly Met Thr Ser Glu Glu Lys<br>        515                   520                   525 | 1584 |
| gaa att ctg ata cgg gac aaa aat gct ctt caa aac atc att ctt tat<br>Glu Ile Leu Ile Arg Asp Lys Asn Ala Leu Gln Asn Ile Ile Leu Tyr<br>530                   535                   540 | 1632 |
| cac ctg aca cca gga gtt ttc att gga aaa gga ttt gaa cct ggt gtt<br>His Leu Thr Pro Gly Val Phe Ile Gly Lys Gly Phe Glu Pro Gly Val<br>545                   550                   555                   560 | 1680 |
| act aac att tta aag acc aca caa gga agc aaa atc ttt ctg aaa gaa<br>Thr Asn Ile Leu Lys Thr Thr Gln Gly Ser Lys Ile Phe Leu Lys Glu<br>                  565                   570                   575 | 1728 |
| gta aat gat aca ctt ctg gtg aat gaa ttg aaa tca aaa gaa tct gac<br>Val Asn Asp Thr Leu Leu Val Asn Glu Leu Lys Ser Lys Glu Ser Asp<br>        580                   585                   590 | 1776 |
| atc atg aca aca aat ggt gta att cat gtt gta gat aaa ctc ctc tat<br>Ile Met Thr Thr Asn Gly Val Ile His Val Val Asp Lys Leu Leu Tyr<br>595                   600                   605 | 1824 |
| cca gca gac aca cct gtt gga aat gat caa ctg ctg gaa ata ctt aat<br>Pro Ala Asp Thr Pro Val Gly Asn Asp Gln Leu Leu Glu Ile Leu Asn<br>610                   615                   620 | 1872 |
| aaa tta atc aaa tac atc caa att aag ttt gtt cgt ggt agc acc ttc<br>Lys Leu Ile Lys Tyr Ile Gln Ile Lys Phe Val Arg Gly Ser Thr Phe<br>625                   630                   635                   640 | 1920 |
| aaa gaa atc ccc gtg act gtc tat aag cca att att aaa aaa tac acc<br>Lys Glu Ile Pro Val Thr Val Tyr Lys Pro Ile Ile Lys Lys Tyr Thr<br>                  645                   650                   655 | 1968 |
| aaa atc att gat gga gtg cct gtg gaa ata act gaa aaa gag aca cga<br>Lys Ile Ile Asp Gly Val Pro Val Glu Ile Thr Glu Lys Glu Thr Arg<br>                        660                   665                   670 | 2016 |
| gaa gaa cga atc att aca ggt cct gaa ata aaa tac act agg att tct<br>Glu Glu Arg Ile Ile Thr Gly Pro Glu Ile Lys Tyr Thr Arg Ile Ser<br>                675                   680                   685 | 2064 |
| act gga ggt gga gaa aca gaa gaa act ctg aag aaa ttg tta caa gaa<br>Thr Gly Gly Gly Glu Thr Glu Glu Thr Leu Lys Lys Leu Leu Gln Glu<br>690                   695                   700 | 2112 |
| gag gtc acc aag gtc acc aaa ttc att gaa ggt ggt gat ggt cat tta<br>Glu Val Thr Lys Val Thr Lys Phe Ile Glu Gly Gly Asp Gly His Leu<br>705                   710                   715                   720 | 2160 |
| ttt gaa gat gaa gaa att aaa aga ctg ctt cag gga gac aca ccc gtg<br>Phe Glu Asp Glu Glu Ile Lys Arg Leu Leu Gln Gly Asp Thr Pro Val<br>                  725                   730                   735 | 2208 |
| agg aag ttg caa gcc aac aaa aaa gtt caa ggt tct aga aga cga tta<br>Arg Lys Leu Gln Ala Asn Lys Lys Val Gln Gly Ser Arg Arg Arg Leu<br>                740                   745                   750 | 2256 |
| agg gaa ggt cgt tct cag<br>Arg Glu Gly Arg Ser Gln<br>        755 | 2274 |

```
<210> SEQ ID NO 10
<211> LENGTH: 758
<212> TYPE: PRT
<213> ORGANISM: Homo sapiens

<400> SEQUENCE: 10

Asn Asn His Tyr Asp Lys Ile Leu Ala His Ser Arg Ile Arg Gly Arg
 1               5                   10                  15
```

```
Asp Gln Gly Pro Asn Val Cys Ala Leu Gln Gln Ile Leu Gly Thr Lys
         20                  25                  30
Lys Lys Tyr Phe Ser Thr Cys Lys Asn Trp Tyr Lys Lys Ser Ile Cys
         35                  40                  45
Gly Gln Lys Thr Thr Val Leu Tyr Glu Cys Cys Pro Gly Tyr Met Arg
 50                  55                  60
Met Glu Gly Met Lys Gly Cys Pro Ala Val Leu Pro Ile Asp His Val
 65                  70                  75                  80
Tyr Gly Thr Leu Gly Ile Val Gly Ala Thr Thr Thr Gln Arg Tyr Ser
                 85                  90                  95
Asp Ala Ser Lys Leu Arg Glu Glu Ile Glu Gly Lys Gly Ser Phe Thr
             100                 105                 110
Tyr Phe Ala Pro Ser Asn Glu Ala Trp Asp Asn Leu Asp Ser Asp Ile
             115                 120                 125
Arg Arg Gly Leu Glu Ser Asn Val Asn Val Glu Leu Leu Asn Ala Leu
130                 135                 140
His Ser His Met Ile Asn Lys Arg Met Leu Thr Lys Asp Leu Lys Asn
145                 150                 155                 160
Gly Met Ile Ile Pro Ser Met Tyr Asn Asn Leu Gly Leu Phe Ile Asn
                165                 170                 175
His Tyr Pro Asn Gly Val Val Thr Val Asn Cys Ala Arg Ile Ile His
            180                 185                 190
Gly Asn Gln Ile Ala Thr Asn Gly Val Val His Val Ile Asp Arg Val
            195                 200                 205
Leu Thr Gln Ile Gly Thr Ser Ile Gln Asp Phe Ile Glu Ala Glu Asp
        210                 215                 220
Asp Leu Ser Ser Phe Arg Ala Ala Ile Thr Ser Asp Ile Leu Glu
225                 230                 235                 240
Ala Leu Gly Arg Asp Gly His Phe Thr Leu Phe Ala Pro Thr Asn Glu
                245                 250                 255
Ala Phe Glu Lys Leu Pro Arg Gly Val Leu Glu Arg Phe Met Gly Asp
            260                 265                 270
Lys Val Ala Ser Glu Ala Leu Met Lys Tyr His Ile Leu Asn Thr Leu
        275                 280                 285
Gln Cys Ser Glu Ser Ile Met Gly Gly Ala Val Phe Glu Thr Leu Glu
    290                 295                 300
Gly Asn Thr Ile Glu Ile Gly Cys Asp Gly Asp Ser Ile Thr Val Asn
305                 310                 315                 320
Gly Ile Lys Met Val Asn Lys Lys Asp Ile Val Thr Asn Asn Gly Val
                325                 330                 335
Ile His Leu Ile Asp Gln Val Leu Ile Pro Asp Ser Ala Lys Gln Val
            340                 345                 350
Ile Glu Leu Ala Gly Lys Gln Gln Thr Thr Phe Thr Asp Leu Val Ala
        355                 360                 365
Gln Leu Gly Leu Ala Ser Ala Leu Arg Pro Asp Gly Glu Tyr Thr Leu
    370                 375                 380
Leu Ala Pro Val Asn Asn Ala Phe Ser Asp Asp Thr Leu Ser Met Val
385                 390                 395                 400
Gln Arg Leu Leu Lys Leu Ile Leu Gln Asn His Ile Leu Lys Val Lys
                405                 410                 415
Val Gly Leu Asn Glu Leu Tyr Asn Gly Gln Ile Leu Glu Thr Ile Gly
            420                 425                 430
Gly Lys Gln Leu Arg Val Phe Val Tyr Arg Thr Ala Val Cys Ile Glu
```

```
                435                 440                 445
Asn Ser Cys Met Glu Lys Gly Ser Lys Gln Gly Arg Asn Gly Ala Ile
    450                 455                 460

His Ile Phe Arg Glu Ile Ile Lys Pro Ala Glu Lys Ser Leu His Glu
465                 470                 475                 480

Lys Leu Lys Gln Asp Lys Arg Phe Ser Thr Phe Leu Ser Leu Leu Glu
                485                 490                 495

Ala Ala Asp Leu Lys Glu Leu Leu Thr Gln Pro Gly Asp Trp Thr Leu
            500                 505                 510

Phe Val Pro Thr Asn Asp Ala Phe Lys Gly Met Thr Ser Glu Glu Lys
        515                 520                 525

Glu Ile Leu Ile Arg Asp Lys Asn Ala Leu Gln Asn Ile Ile Leu Tyr
    530                 535                 540

His Leu Thr Pro Gly Val Phe Ile Gly Lys Gly Phe Glu Pro Gly Val
545                 550                 555                 560

Thr Asn Ile Leu Lys Thr Thr Gln Gly Ser Lys Ile Phe Leu Lys Glu
                565                 570                 575

Val Asn Asp Thr Leu Leu Val Asn Glu Leu Lys Ser Lys Glu Ser Asp
            580                 585                 590

Ile Met Thr Thr Asn Gly Val Ile His Val Val Asp Lys Leu Leu Tyr
        595                 600                 605

Pro Ala Asp Thr Pro Val Gly Asn Asp Gln Leu Leu Glu Ile Leu Asn
    610                 615                 620

Lys Leu Ile Lys Tyr Ile Gln Ile Lys Phe Val Arg Gly Ser Thr Phe
625                 630                 635                 640

Lys Glu Ile Pro Val Thr Val Tyr Lys Pro Ile Ile Lys Lys Tyr Thr
                645                 650                 655

Lys Ile Ile Asp Gly Val Pro Val Glu Ile Thr Glu Lys Glu Thr Arg
            660                 665                 670

Glu Glu Arg Ile Ile Thr Gly Pro Glu Ile Lys Tyr Thr Arg Ile Ser
        675                 680                 685

Thr Gly Gly Gly Glu Thr Glu Glu Thr Leu Lys Lys Leu Leu Gln Glu
    690                 695                 700

Glu Val Thr Lys Val Thr Lys Phe Ile Glu Gly Gly Asp Gly His Leu
705                 710                 715                 720

Phe Glu Asp Glu Glu Ile Lys Arg Leu Leu Gln Gly Asp Thr Pro Val
                725                 730                 735

Arg Lys Leu Gln Ala Asn Lys Lys Val Gln Gly Ser Arg Arg Arg Leu
            740                 745                 750

Arg Glu Gly Arg Ser Gln
        755

<210> SEQ ID NO 11
<211> LENGTH: 2313
<212> TYPE: DNA
<213> ORGANISM: Homo sapiens
<220> FEATURE:
<221> NAME/KEY: CDS
<222> LOCATION: (1)...(2313)

<400> SEQUENCE: 11 atg att ccc ttt tta ccc atg ttt tct cta cta ttg ctg ctt att gtt     48
Met Ile Pro Phe Leu Pro Met Phe Ser Leu Leu Leu Leu Leu Ile Val
1               5                   10                  15 aac cct ata aac gcc aac aat cat tat gac aag atc ttg gct cat agt     96
Asn Pro Ile Asn Ala Asn Asn His Tyr Asp Lys Ile Leu Ala His Ser
```

-continued

|  |  |
|---|---|
| cgt atc agg ggt cgg gac caa ggc cca aat gtc tgt gcc ctt caa cag<br>Arg Ile Arg Gly Arg Asp Gln Gly Pro Asn Val Cys Ala Leu Gln Gln<br>35                     40                     45 | 144 |
| att ttg ggc acc aaa aag aaa tac ttc agc act tgt aag aac tgg tat<br>Ile Leu Gly Thr Lys Lys Lys Tyr Phe Ser Thr Cys Lys Asn Trp Tyr<br>50                     55                    60 | 192 |
| aaa aag tcc atc tgt gga cag aaa acg act gtg tta tat gaa tgt tgc<br>Lys Lys Ser Ile Cys Gly Gln Lys Thr Thr Val Leu Tyr Glu Cys Cys<br>65                     70                    75                   80 | 240 |
| cct ggt tat atg aga atg gaa gga atg aaa ggc tgc cca gca gtt ttg<br>Pro Gly Tyr Met Arg Met Glu Gly Met Lys Gly Cys Pro Ala Val Leu<br>                  85                    90                    95 | 288 |
| ccc att gac cat gtt tat ggc act ctg ggc atc gtg gga gcc acc aca<br>Pro Ile Asp His Val Tyr Gly Thr Leu Gly Ile Val Gly Ala Thr Thr<br>                100                   105                  110 | 336 |
| acg cag cgc tat tct gac gcc tca aaa ctg agg gag gag atc gag gga<br>Thr Gln Arg Tyr Ser Asp Ala Ser Lys Leu Arg Glu Glu Ile Glu Gly<br>                115                   120                  125 | 384 |
| aag gga tcc ttc act tac ttt gca ccg agt aat gag gct tgg gac aac<br>Lys Gly Ser Phe Thr Tyr Phe Ala Pro Ser Asn Glu Ala Trp Asp Asn<br>130                   135                   140 | 432 |
| ttg gat tct gat atc cgt aga ggt ttg gag agc aac gtg aat gtt gaa<br>Leu Asp Ser Asp Ile Arg Arg Gly Leu Glu Ser Asn Val Asn Val Glu<br>145                   150                   155                  160 | 480 |
| tta ctg aat gct tta cat agt cac atg att aat aag aga atg ttg acc<br>Leu Leu Asn Ala Leu His Ser His Met Ile Asn Lys Arg Met Leu Thr<br>                165                   170                  175 | 528 |
| aag gac tta aaa aat ggc atg att att cct tca atg tat aac aat ttg<br>Lys Asp Leu Lys Asn Gly Met Ile Ile Pro Ser Met Tyr Asn Asn Leu<br>                180                   185                  190 | 576 |
| ggg ctt ttc att aac cat tat cct aat ggg gtt gtc act gtt aat tgt<br>Gly Leu Phe Ile Asn His Tyr Pro Asn Gly Val Val Thr Val Asn Cys<br>                195                   200                  205 | 624 |
| gct cga atc atc cat ggg aac cag att gca aca aat ggt gtt gtc cat<br>Ala Arg Ile Ile His Gly Asn Gln Ile Ala Thr Asn Gly Val Val His<br>210                   215                   220 | 672 |
| gtc att gac cgt gtg ctt aca caa att ggt acc tca att caa gac ttc<br>Val Ile Asp Arg Val Leu Thr Gln Ile Gly Thr Ser Ile Gln Asp Phe<br>225                   230                   235                  240 | 720 |
| att gaa gca gaa gat gac ctt tca tct ttt aga gca gct gcc atc aca<br>Ile Glu Ala Glu Asp Asp Leu Ser Ser Phe Arg Ala Ala Ala Ile Thr<br>                245                   250                  255 | 768 |
| tcg gac ata ttg gag gcc ctt gga aga gac ggt cac ttc aca ctc ttt<br>Ser Asp Ile Leu Glu Ala Leu Gly Arg Asp Gly His Phe Thr Leu Phe<br>                260                   265                  270 | 816 |
| gct ccc acc aat gag gct ttt gag aaa ctt cca cga ggt gtc cta gaa<br>Ala Pro Thr Asn Glu Ala Phe Glu Lys Leu Pro Arg Gly Val Leu Glu<br>                275                   280                  285 | 864 |
| agg atc atg gga gac aaa gtg gct tcc gaa gct ctt atg aag tac cac<br>Arg Ile Met Gly Asp Lys Val Ala Ser Glu Ala Leu Met Lys Tyr His<br>290                   295                   300 | 912 |
| atc tta aat act ctc cag tgt tct gag tct att atg gga gga gca gtc<br>Ile Leu Asn Thr Leu Gln Cys Ser Glu Ser Ile Met Gly Gly Ala Val<br>305                   310                   315                  320 | 960 |
| ttt gag acg ctg gaa gga aat aca att gag ata gga tgt gac ggt gac<br>Phe Glu Thr Leu Glu Gly Asn Thr Ile Glu Ile Gly Cys Asp Gly Asp<br>                325                   330                  335 | 1008 |
| agt ata aca gta aat gga atc aaa atg gtg aac aaa aag gat att gtg | 1056 |

```
                                                            -continued

Ser Ile Thr Val Asn Gly Ile Lys Met Val Asn Lys Asp Ile Val
            340                 345                 350 aca aat aat ggt gtg atc cat ttg att gat cag gtc cta att cct gat      1104
Thr Asn Asn Gly Val Ile His Leu Ile Asp Gln Val Leu Ile Pro Asp
            355                 360                 365 tct gcc aaa caa gtt att gag ctg gct gga aaa cag caa acc acc ttc      1152
Ser Ala Lys Gln Val Ile Glu Leu Ala Gly Lys Gln Gln Thr Thr Phe
            370                 375                 380 acg gat ctt gtg gcc caa tta ggc ttg gca tct gct ctg agg cca gat      1200
Thr Asp Leu Val Ala Gln Leu Gly Leu Ala Ser Ala Leu Arg Pro Asp
385                 390                 395                 400 gga gaa tac act ttg ctg gca cct gtg aat aat gca ttt tct gat gat      1248
Gly Glu Tyr Thr Leu Leu Ala Pro Val Asn Asn Ala Phe Ser Asp Asp
            405                 410                 415 act ctc agc atg gat cag cgc ctc ctt aaa tta att ctg cag aat cac      1296
Thr Leu Ser Met Asp Gln Arg Leu Leu Lys Leu Ile Leu Gln Asn His
            420                 425                 430 ata ttg aaa gta aaa gtt ggc ctt aat gag ctt tac aac ggg caa ata      1344
Ile Leu Lys Val Lys Val Gly Leu Asn Glu Leu Tyr Asn Gly Gln Ile
            435                 440                 445 ctg gaa acc atc gga ggc aaa cag ctc aga gtc ttc gta tat cgt aca      1392
Leu Glu Thr Ile Gly Gly Lys Gln Leu Arg Val Phe Val Tyr Arg Thr
            450                 455                 460 gct gtc tgc att gaa aat tca tgc atg gag aaa ggg agt aag caa ggg      1440
Ala Val Cys Ile Glu Asn Ser Cys Met Glu Lys Gly Ser Lys Gln Gly
465                 470                 475                 480 aga aac ggt gcg att cac ata ttc cgc gag atc atc aag cca gca gag      1488
Arg Asn Gly Ala Ile His Ile Phe Arg Glu Ile Ile Lys Pro Ala Glu
            485                 490                 495 aaa tcc ctc cat gaa aag tta aaa caa gat aag cgc ttt acg acc ttc      1536
Lys Ser Leu His Glu Lys Leu Lys Gln Asp Lys Arg Phe Thr Thr Phe
            500                 505                 510 ctc agc cta ctt gaa gct gca gac ttg aaa gag ctc ctg aca caa cct      1584
Leu Ser Leu Leu Glu Ala Ala Asp Leu Lys Glu Leu Leu Thr Gln Pro
            515                 520                 525 gga gac tgg aca tta ttt gtg cca acc aat gat gct ttt aag gga atg      1632
Gly Asp Trp Thr Leu Phe Val Pro Thr Asn Asp Ala Phe Lys Gly Met
530                 535                 540 act agt gaa gaa aaa gaa att ctg ata cgg gac aaa aat gct ctt caa      1680
Thr Ser Glu Glu Lys Glu Ile Leu Ile Arg Asp Lys Asn Ala Leu Gln
545                 550                 555                 560 aac atc att ctt tat cac ctg aca cca gga gtt ttc att gga aaa gga      1728
Asn Ile Ile Leu Tyr His Leu Thr Pro Gly Val Phe Ile Gly Lys Gly
            565                 570                 575 ttt gaa cct ggt gtt act aac att tta aag acc aca caa gga agc aaa      1776
Phe Glu Pro Gly Val Thr Asn Ile Leu Lys Thr Thr Gln Gly Ser Lys
            580                 585                 590 atc ttt ctg aaa gaa gta aat gat aca ctt ctg gtg aat gaa ttg aaa      1824
Ile Phe Leu Lys Glu Val Asn Asp Thr Leu Leu Val Asn Glu Leu Lys
            595                 600                 605 tca aaa gaa tct gac atc atg aca aca aat ggt gta att cat gtt gta      1872
Ser Lys Glu Ser Asp Ile Met Thr Thr Asn Gly Val Ile His Val Val
610                 615                 620 gat aaa ctc ctc tat cca gca gac aca cct gtt gga aat gat caa ctg      1920
Asp Lys Leu Leu Tyr Pro Ala Asp Thr Pro Val Gly Asn Asp Gln Leu
625                 630                 635                 640 ctg gaa ata ctt aat aaa tta atc aaa tac atc caa att aag ttt gtt      1968
Leu Glu Ile Leu Asn Lys Leu Ile Lys Tyr Ile Gln Ile Lys Phe Val
            645                 650                 655
```

-continued

```
cgt ggt agc acc ttc aaa gaa atc ccc gtg act gtc tat aga ccc aca    2016
Arg Gly Ser Thr Phe Lys Glu Ile Pro Val Thr Val Tyr Arg Pro Thr
            660                 665                 670 cta aca aaa gtc aaa att gaa ggt gaa cct gaa ttc aga ctg att aaa    2064
Leu Thr Lys Val Lys Ile Glu Gly Glu Pro Glu Phe Arg Leu Ile Lys
675                 680                 685 gaa ggt gaa aca ata act gaa gtg atc cat gga gag cca att att aaa    2112
Glu Gly Glu Thr Ile Thr Glu Val Ile His Gly Glu Pro Ile Ile Lys
    690                 695                 700 aaa tac acc aaa atc att gat gga gtg cct gtg gaa ata act gaa aaa    2160
Lys Tyr Thr Lys Ile Ile Asp Gly Val Pro Val Glu Ile Thr Glu Lys
705                 710                 715                 720 gag aca cga gaa gaa cga atc att aca ggt cct gaa ata aaa tac act    2208
Glu Thr Arg Glu Glu Arg Ile Ile Thr Gly Pro Glu Ile Lys Tyr Thr
                725                 730                 735 agg att tct act gga ggt gga gaa aca gaa gaa act ctg aag aaa ttg    2256
Arg Ile Ser Thr Gly Gly Gly Glu Thr Glu Glu Thr Leu Lys Lys Leu
            740                 745                 750 tta caa gaa gac aca ccc gtg agg aag ttg caa gcc aac aaa aaa agt    2304
Leu Gln Glu Asp Thr Pro Val Arg Lys Leu Gln Ala Asn Lys Lys Ser
        755                 760                 765 tca agg atc                                                        2313
Ser Arg Ile
    770
```

<210> SEQ ID NO 12
<211> LENGTH: 771
<212> TYPE: PRT
<213> ORGANISM: Homo sapiens

<400> SEQUENCE: 12

```
Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205
```

-continued

```
Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
                275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Thr Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
```

-continued

```
                625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Arg Pro Thr
                    660                 665                 670

Leu Thr Lys Val Lys Ile Glu Gly Pro Glu Phe Arg Leu Ile Lys
                    675                 680             685

Glu Gly Glu Thr Ile Thr Glu Val Ile His Gly Pro Ile Ile Lys
                690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                    725                 730                 735

Arg Ile Ser Thr Gly Gly Glu Thr Glu Glu Thr Leu Lys Lys Leu
                    740                 745                 750

Leu Gln Glu Asp Thr Pro Val Arg Lys Leu Gln Ala Asn Lys Lys Ser
                    755                 760                 765

Ser Arg Ile
    770
```

<210> SEQ ID NO 13
<211> LENGTH: 2250
<212> TYPE: DNA
<213> ORGANISM: Homo sapiens
<220> FEATURE:
<221> NAME/KEY: CDS
<222> LOCATION: (1)...(2250)

<400> SEQUENCE: 13

```
aac aat cat tat gac aag atc ttg gct cat agt cgt atc agg ggt cgg      48
Asn Asn His Tyr Asp Lys Ile Leu Ala His Ser Arg Ile Arg Gly Arg
 1               5                  10                  15 gac caa ggc cca aat gtc tgt gcc ctt caa cag att ttg ggc acc aaa      96
Asp Gln Gly Pro Asn Val Cys Ala Leu Gln Gln Ile Leu Gly Thr Lys
                20                  25                  30 aag aaa tac ttc agc act tgt aag aac tgg tat aaa aag tcc atc tgt     144
Lys Lys Tyr Phe Ser Thr Cys Lys Asn Trp Tyr Lys Lys Ser Ile Cys
            35                  40                  45 gga cag aaa acg act gtg tta tat gaa tgt tgc cct ggt tat atg aga     192
Gly Gln Lys Thr Thr Val Leu Tyr Glu Cys Cys Pro Gly Tyr Met Arg
        50                  55                  60 atg gaa gga atg aaa ggc tgc cca gca gtt ttg ccc att gac cat gtt     240
Met Glu Gly Met Lys Gly Cys Pro Ala Val Leu Pro Ile Asp His Val
 65                  70                  75                  80 tat ggc act ctg ggc atc gtg gga gcc acc aca acg cag cgc tat tct     288
Tyr Gly Thr Leu Gly Ile Val Gly Ala Thr Thr Thr Gln Arg Tyr Ser
                85                  90                  95 gac gcc tca aaa ctg agg gag gag atc gag gga aag gga tcc ttc act     336
Asp Ala Ser Lys Leu Arg Glu Glu Ile Glu Gly Lys Gly Ser Phe Thr
                100                 105                 110 tac ttt gca ccg agt aat gag gct tgg gac aac ttg gat tct gat atc     384
Tyr Phe Ala Pro Ser Asn Glu Ala Trp Asp Asn Leu Asp Ser Asp Ile
            115                 120                 125 cgt aga ggt ttg gag agc aac gtg aat gtt gaa tta ctg aat gct tta     432
Arg Arg Gly Leu Glu Ser Asn Val Asn Val Glu Leu Leu Asn Ala Leu
        130                 135                 140 cat agt cac atg att aat aag aga atg ttg acc aag gac tta aaa aat     480
His Ser His Met Ile Asn Lys Arg Met Leu Thr Lys Asp Leu Lys Asn
145                 150                 155                 160
```

-continued

| | |
|---|---|
| ggc atg att att cct tca atg tat aac aat ttg ggg ctt ttc att aac<br>Gly Met Ile Ile Pro Ser Met Tyr Asn Asn Leu Gly Leu Phe Ile Asn<br>            165                     170                     175 | 528 |
| cat tat cct aat ggg gtt gtc act gtt aat tgt gct cga atc atc cat<br>His Tyr Pro Asn Gly Val Val Thr Val Asn Cys Ala Arg Ile Ile His<br>          180                     185                     190 | 576 |
| ggg aac cag att gca aca aat ggt gtt gtc cat gtc att gac cgt gtg<br>Gly Asn Gln Ile Ala Thr Asn Gly Val Val His Val Ile Asp Arg Val<br>           195                     200                   205 | 624 |
| ctt aca caa att ggt acc tca att caa gac ttc att gaa gca gaa gat<br>Leu Thr Gln Ile Gly Thr Ser Ile Gln Asp Phe Ile Glu Ala Glu Asp<br>210                     215                     220 | 672 |
| gac ctt tca tct ttt aga gca gct gcc atc aca tcg gac ata ttg gag<br>Asp Leu Ser Ser Phe Arg Ala Ala Ala Ile Thr Ser Asp Ile Leu Glu<br>225                     230                     235                    240 | 720 |
| gcc ctt gga aga gac ggt cac ttc aca ctc ttt gct ccc acc aat gag<br>Ala Leu Gly Arg Asp Gly His Phe Thr Leu Phe Ala Pro Thr Asn Glu<br>                    245                     250                     255 | 768 |
| gct ttt gag aaa ctt cca cga ggt gtc cta gaa agg atc atg gga gac<br>Ala Phe Glu Lys Leu Pro Arg Gly Val Leu Glu Arg Ile Met Gly Asp<br>            260                     265                   270 | 816 |
| aaa gtg gct tcc gaa gct ctt atg aag tac cac atc tta aat act ctc<br>Lys Val Ala Ser Glu Ala Leu Met Lys Tyr His Ile Leu Asn Thr Leu<br>              275                     280                     285 | 864 |
| cag tgt tct gag tct att atg gga gga gca gtc ttt gag acg ctg gaa<br>Gln Cys Ser Glu Ser Ile Met Gly Gly Ala Val Phe Glu Thr Leu Glu<br>          290                     295                   300 | 912 |
| gga aat aca att gag ata gga tgt gac ggt gac agt ata aca gta aat<br>Gly Asn Thr Ile Glu Ile Gly Cys Asp Gly Asp Ser Ile Thr Val Asn<br>305                     310                     315                    320 | 960 |
| gga atc aaa atg gtg aac aaa aag gat att gtg aca aat aat ggt gtg<br>Gly Ile Lys Met Val Asn Lys Lys Asp Ile Val Thr Asn Asn Gly Val<br>                    325                     330                    335 | 1008 |
| atc cat ttg att gat cag gtc cta att cct gat tct gcc aaa caa gtt<br>Ile His Leu Ile Asp Gln Val Leu Ile Pro Asp Ser Ala Lys Gln Val<br>              340                     345                    350 | 1056 |
| att gag ctg gct gga aaa cag caa acc acc ttc acg gat ctt gtg gcc<br>Ile Glu Leu Ala Gly Lys Gln Gln Thr Thr Phe Thr Asp Leu Val Ala<br>          355                     360                   365 | 1104 |
| caa tta ggc ttg gca tct gct ctg agg cca gat gga gaa tac act ttg<br>Gln Leu Gly Leu Ala Ser Ala Leu Arg Pro Asp Gly Glu Tyr Thr Leu<br>370                     375                     380 | 1152 |
| ctg gca cct gtg aat aat gca ttt tct gat gat act ctc agc atg gat<br>Leu Ala Pro Val Asn Asn Ala Phe Ser Asp Asp Thr Leu Ser Met Asp<br>385                     390                     395                    400 | 1200 |
| cag cgc ctc ctt aaa tta att ctg cag aat cac ata ttg aaa gta aaa<br>Gln Arg Leu Leu Lys Leu Ile Leu Gln Asn His Ile Leu Lys Val Lys<br>                    405                     410                    415 | 1248 |
| gtt ggc ctt aat gag ctt tac aac ggg caa ata ctg gaa acc atc gga<br>Val Gly Leu Asn Glu Leu Tyr Asn Gly Gln Ile Leu Glu Thr Ile Gly<br>            420                     425                   430 | 1296 |
| ggc aaa cag ctc aga gtc ttc gta tat cgt aca gct gtc tgc att gaa<br>Gly Lys Gln Leu Arg Val Phe Val Tyr Arg Thr Ala Val Cys Ile Glu<br>              435                     440                    445 | 1344 |
| aat tca tgc atg gag aaa ggg agt aag caa ggg aga aac ggt gcg att<br>Asn Ser Cys Met Glu Lys Gly Ser Lys Gln Gly Arg Asn Gly Ala Ile<br>450                     455                     460 | 1392 |
| cac ata ttc cgc gag atc atc aag cca gca gag aaa tcc ctc cat gaa<br>His Ile Phe Arg Glu Ile Ile Lys Pro Ala Glu Lys Ser Leu His Glu | 1440 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 465 |     |     |     |     | 470 |     |     |     |     | 475 |     |     | 480 |      |
| aag | tta | aaa | caa | gat | aag | cgc | ttt | acg | acc | ttc | ctc | agc | cta | ctt | gaa | 1488 |
| Lys | Leu | Lys | Gln | Asp | Lys | Arg | Phe | Thr | Thr | Phe | Leu | Ser | Leu | Leu | Glu |      |
|     |     |     |     | 485 |     |     |     |     | 490 |     |     |     |     | 495 |     |      |
| gct | gca | gac | ttg | aaa | gag | ctc | ctg | aca | caa | cct | gga | gac | tgg | aca | tta | 1536 |
| Ala | Ala | Asp | Leu | Lys | Glu | Leu | Leu | Thr | Gln | Pro | Gly | Asp | Trp | Thr | Leu |      |
|     |     |     | 500 |     |     |     |     | 505 |     |     |     |     | 510 |     |     |      |
| ttt | gtg | cca | acc | aat | gat | gct | ttt | aag | gga | atg | act | agt | gaa | gaa | aaa | 1584 |
| Phe | Val | Pro | Thr | Asn | Asp | Ala | Phe | Lys | Gly | Met | Thr | Ser | Glu | Glu | Lys |      |
|     |     | 515 |     |     |     |     | 520 |     |     |     |     | 525 |     |     |     |      |
| gaa | att | ctg | ata | cgg | gac | aaa | aat | gct | ctt | caa | aac | atc | att | ctt | tat | 1632 |
| Glu | Ile | Leu | Ile | Arg | Asp | Lys | Asn | Ala | Leu | Gln | Asn | Ile | Ile | Leu | Tyr |      |
|     | 530 |     |     |     |     | 535 |     |     |     |     | 540 |     |     |     |     |      |
| cac | ctg | aca | cca | gga | gtt | ttc | att | gga | aaa | gga | ttt | gaa | cct | ggt | gtt | 1680 |
| His | Leu | Thr | Pro | Gly | Val | Phe | Ile | Gly | Lys | Gly | Phe | Glu | Pro | Gly | Val |      |
| 545 |     |     |     |     | 550 |     |     |     |     | 555 |     |     |     |     | 560 |      |
| act | aac | att | tta | aag | acc | aca | caa | gga | agc | aaa | atc | ttt | ctg | aaa | gaa | 1728 |
| Thr | Asn | Ile | Leu | Lys | Thr | Thr | Gln | Gly | Ser | Lys | Ile | Phe | Leu | Lys | Glu |      |
|     |     |     |     | 565 |     |     |     |     | 570 |     |     |     |     | 575 |     |      |
| gta | aat | gat | aca | ctt | ctg | gtg | aat | gaa | ttg | aaa | tca | aaa | gaa | tct | gac | 1776 |
| Val | Asn | Asp | Thr | Leu | Leu | Val | Asn | Glu | Leu | Lys | Ser | Lys | Glu | Ser | Asp |      |
|     |     |     | 580 |     |     |     |     | 585 |     |     |     |     | 590 |     |     |      |
| atc | atg | aca | aca | aat | ggt | gta | att | cat | gtt | gta | gat | aaa | ctc | ctc | tat | 1824 |
| Ile | Met | Thr | Thr | Asn | Gly | Val | Ile | His | Val | Val | Asp | Lys | Leu | Leu | Tyr |      |
|     |     | 595 |     |     |     |     | 600 |     |     |     |     | 605 |     |     |     |      |
| cca | gca | gac | aca | cct | gtt | gga | aat | gat | caa | ctg | ctg | gaa | ata | ctt | aat | 1872 |
| Pro | Ala | Asp | Thr | Pro | Val | Gly | Asn | Asp | Gln | Leu | Leu | Glu | Ile | Leu | Asn |      |
|     | 610 |     |     |     |     | 615 |     |     |     |     | 620 |     |     |     |     |      |
| aaa | tta | atc | aaa | tac | atc | caa | att | aag | ttt | gtt | cgt | ggt | agc | acc | ttc | 1920 |
| Lys | Leu | Ile | Lys | Tyr | Ile | Gln | Ile | Lys | Phe | Val | Arg | Gly | Ser | Thr | Phe |      |
| 625 |     |     |     |     | 630 |     |     |     |     | 635 |     |     |     |     | 640 |      |
| aaa | gaa | atc | ccc | gtg | act | gtc | tat | aga | ccc | aca | cta | aca | aaa | gtc | aaa | 1968 |
| Lys | Glu | Ile | Pro | Val | Thr | Val | Tyr | Arg | Pro | Thr | Leu | Thr | Lys | Val | Lys |      |
|     |     |     |     | 645 |     |     |     |     | 650 |     |     |     |     | 655 |     |      |
| att | gaa | ggt | gaa | cct | gaa | ttc | aga | ctg | att | aaa | gaa | ggt | gaa | aca | ata | 2016 |
| Ile | Glu | Gly | Glu | Pro | Glu | Phe | Arg | Leu | Ile | Lys | Glu | Gly | Glu | Thr | Ile |      |
|     |     |     | 660 |     |     |     |     | 665 |     |     |     |     | 670 |     |     |      |
| act | gaa | gtg | atc | cat | gga | gag | cca | att | att | aaa | aaa | tac | acc | aaa | atc | 2064 |
| Thr | Glu | Val | Ile | His | Gly | Glu | Pro | Ile | Ile | Lys | Lys | Tyr | Thr | Lys | Ile |      |
|     |     | 675 |     |     |     |     | 680 |     |     |     |     | 685 |     |     |     |      |
| att | gat | gga | gtg | cct | gtg | gaa | ata | act | gaa | aaa | gag | aca | cga | gaa | gaa | 2112 |
| Ile | Asp | Gly | Val | Pro | Val | Glu | Ile | Thr | Glu | Lys | Glu | Thr | Arg | Glu | Glu |      |
|     | 690 |     |     |     |     | 695 |     |     |     |     | 700 |     |     |     |     |      |
| cga | atc | att | aca | ggt | cct | gaa | ata | aaa | tac | act | agg | att | tct | act | gga | 2160 |
| Arg | Ile | Ile | Thr | Gly | Pro | Glu | Ile | Lys | Tyr | Thr | Arg | Ile | Ser | Thr | Gly |      |
| 705 |     |     |     |     | 710 |     |     |     |     | 715 |     |     |     |     | 720 |      |
| ggt | gga | gaa | aca | gaa | gaa | act | ctg | aag | aaa | ttg | tta | caa | gaa | gac | aca | 2208 |
| Gly | Gly | Glu | Thr | Glu | Glu | Thr | Leu | Lys | Lys | Leu | Leu | Gln | Glu | Asp | Thr |      |
|     |     |     |     | 725 |     |     |     |     | 730 |     |     |     |     | 735 |     |      |
| ccc | gtg | agg | aag | ttg | caa | gcc | aac | aaa | aaa | agt | tca | agg | atc |     |     | 2250 |
| Pro | Val | Arg | Lys | Leu | Gln | Ala | Asn | Lys | Lys | Ser | Ser | Arg | Ile |     |     |      |
|     |     |     | 740 |     |     |     |     | 745 |     |     |     |     | 750 |     |     |      |

<210> SEQ ID NO 14
<211> LENGTH: 750
<212> TYPE: PRT
<213> ORGANISM: Homo sapiens

<400> SEQUENCE: 14

Asn Asn His Tyr Asp Lys Ile Leu Ala His Ser Arg Ile Arg Gly Arg

```
            1               5                  10                 15
Asp Gln Gly Pro Asn Val Cys Ala Leu Gln Gln Ile Leu Gly Thr Lys
                20                  25                  30
Lys Lys Tyr Phe Ser Thr Cys Lys Asn Trp Tyr Lys Lys Ser Ile Cys
                35                  40                  45
Gly Gln Lys Thr Thr Val Leu Tyr Glu Cys Cys Pro Gly Tyr Met Arg
                50                  55                  60
Met Glu Gly Met Lys Gly Cys Pro Ala Val Leu Pro Ile Asp His Val
65                      70                  75                  80
Tyr Gly Thr Leu Gly Ile Val Gly Ala Thr Thr Thr Gln Arg Tyr Ser
                    85                  90                  95
Asp Ala Ser Lys Leu Arg Glu Glu Ile Glu Gly Lys Gly Ser Phe Thr
                100                 105                 110
Tyr Phe Ala Pro Ser Asn Glu Ala Trp Asp Asn Leu Asp Ser Asp Ile
                115                 120                 125
Arg Arg Gly Leu Glu Ser Asn Val Asn Val Glu Leu Leu Asn Ala Leu
                130                 135                 140
His Ser His Met Ile Asn Lys Arg Met Leu Thr Lys Asp Leu Lys Asn
145                 150                 155                 160
Gly Met Ile Ile Pro Ser Met Tyr Asn Asn Leu Gly Leu Phe Ile Asn
                    165                 170                 175
His Tyr Pro Asn Gly Val Val Thr Val Asn Cys Ala Arg Ile Ile His
                180                 185                 190
Gly Asn Gln Ile Ala Thr Asn Gly Val Val His Val Ile Asp Arg Val
                195                 200                 205
Leu Thr Gln Ile Gly Thr Ser Ile Gln Asp Phe Ile Glu Ala Glu Asp
    210                 215                 220
Asp Leu Ser Ser Phe Arg Ala Ala Ile Thr Ser Asp Ile Leu Glu
225                 230                 235                 240
Ala Leu Gly Arg Asp Gly His Phe Thr Leu Phe Ala Pro Thr Asn Glu
                    245                 250                 255
Ala Phe Glu Lys Leu Pro Arg Gly Val Leu Glu Arg Ile Met Gly Asp
                260                 265                 270
Lys Val Ala Ser Glu Ala Leu Met Lys Tyr His Ile Leu Asn Thr Leu
    275                 280                 285
Gln Cys Ser Glu Ser Ile Met Gly Gly Ala Val Phe Glu Thr Leu Glu
    290                 295                 300
Gly Asn Thr Ile Glu Ile Gly Cys Asp Gly Asp Ser Ile Thr Val Asn
305                 310                 315                 320
Gly Ile Lys Met Val Asn Lys Lys Asp Ile Val Thr Asn Asn Gly Val
                325                 330                 335
Ile His Leu Ile Asp Gln Val Leu Ile Pro Asp Ser Ala Lys Gln Val
                340                 345                 350
Ile Glu Leu Ala Gly Lys Gln Gln Thr Thr Phe Thr Asp Leu Val Ala
                355                 360                 365
Gln Leu Gly Leu Ala Ser Ala Leu Arg Pro Asp Gly Glu Tyr Thr Leu
    370                 375                 380
Leu Ala Pro Val Asn Asn Ala Phe Ser Asp Asp Thr Leu Ser Met Asp
385                 390                 395                 400
Gln Arg Leu Leu Lys Leu Ile Leu Gln Asn His Ile Leu Lys Val Lys
                405                 410                 415
Val Gly Leu Asn Glu Leu Tyr Asn Gly Gln Ile Leu Glu Thr Ile Gly
                420                 425                 430
```

```
Gly Lys Gln Leu Arg Val Phe Val Tyr Arg Thr Ala Val Cys Ile Glu
            435                 440                 445

Asn Ser Cys Met Glu Lys Gly Ser Lys Gln Gly Arg Asn Gly Ala Ile
        450                 455                 460

His Ile Phe Arg Glu Ile Ile Lys Pro Ala Glu Lys Ser Leu His Glu
465                 470                 475                 480

Lys Leu Lys Gln Asp Lys Arg Phe Thr Thr Phe Leu Ser Leu Leu Glu
                485                 490                 495

Ala Ala Asp Leu Lys Glu Leu Leu Thr Gln Pro Gly Asp Trp Thr Leu
            500                 505                 510

Phe Val Pro Thr Asn Asp Ala Phe Lys Gly Met Thr Ser Glu Glu Lys
        515                 520                 525

Glu Ile Leu Ile Arg Asp Lys Asn Ala Leu Gln Asn Ile Ile Leu Tyr
530                 535                 540

His Leu Thr Pro Gly Val Phe Ile Gly Lys Gly Phe Glu Pro Gly Val
545                 550                 555                 560

Thr Asn Ile Leu Lys Thr Thr Gln Gly Ser Lys Ile Phe Leu Lys Glu
                565                 570                 575

Val Asn Asp Thr Leu Leu Val Asn Glu Leu Lys Ser Lys Glu Ser Asp
            580                 585                 590

Ile Met Thr Thr Asn Gly Val Ile His Val Val Asp Lys Leu Leu Tyr
        595                 600                 605

Pro Ala Asp Thr Pro Val Gly Asn Asp Gln Leu Leu Glu Ile Leu Asn
610                 615                 620

Lys Leu Ile Lys Tyr Ile Gln Ile Lys Phe Val Arg Gly Ser Thr Phe
625                 630                 635                 640

Lys Glu Ile Pro Val Thr Val Tyr Arg Pro Thr Leu Thr Lys Val Lys
                645                 650                 655

Ile Glu Gly Glu Pro Glu Phe Arg Leu Ile Lys Glu Gly Glu Thr Ile
            660                 665                 670

Thr Glu Val Ile His Gly Glu Pro Ile Ile Lys Lys Tyr Thr Lys Ile
        675                 680                 685

Ile Asp Gly Val Pro Val Glu Ile Thr Glu Lys Glu Thr Arg Glu Glu
690                 695                 700

Arg Ile Ile Thr Gly Pro Glu Ile Lys Tyr Thr Arg Ile Ser Thr Gly
705                 710                 715                 720

Gly Gly Glu Thr Glu Glu Thr Leu Lys Lys Leu Leu Gln Glu Asp Thr
                725                 730                 735

Pro Val Arg Lys Leu Gln Ala Asn Lys Lys Ser Ser Arg Ile
            740                 745                 750

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
atgattccct ttttacccat gttttctcta                                    30

<210> SEQ ID NO 16
<211> LENGTH: 34
<212> TYPE: DNA
<213> ORGANISM: Artificial Sequence
<220> FEATURE:
```

```
-continued

<223> OTHER INFORMATION: primer

<400> SEQUENCE: 16
tcactgagaa cgaccttccc ttaatcgtct tcta                                34

<210> SEQ ID NO 17
<211> LENGTH: 10
<212> TYPE: DNA
<213> ORGANISM: Artificial Sequence
<220> FEATURE:
<223> OTHER INFORMATION: primer

<400> SEQUENCE: 17
ctgatccatg                                                           10

<210> SEQ ID NO 18
<211> LENGTH: 4
<212> TYPE: PRT
<213> ORGANISM: Artificial Sequence
<220> FEATURE:
<223> OTHER INFORMATION: exemplary motif

<400> SEQUENCE: 18

Ser Ser Arg Ile
  1
```